(12) United States Patent
Hufton et al.

(10) Patent No.: US 9,040,258 B2
(45) Date of Patent: *May 26, 2015

(54) MULTI-CHAIN EUKARYOTIC DISPLAY VECTORS AND USES THEREOF

(75) Inventors: Simon E. Hufton, Clitheroe Lanes (GB); Hendricus Renerus Jacobus Mattheus Hoogenboom, Maastricht (NL)

(73) Assignee: Dyax Corp., Burlington, MA (US)

( * ) Notice: Subject to any disclaimer, the term of this patent is extended or adjusted under 35 U.S.C. 154(b) by 126 days.

This patent is subject to a terminal disclaimer.

(21) Appl. No.: 13/170,362

(22) Filed: Jun. 28, 2011

(65) Prior Publication Data

US 2011/0287971 A1 Nov. 24, 2011

Related U.S. Application Data

(60) Division of application No. 12/625,337, filed on Nov. 24, 2009, which is a continuation of application No. 10/262,646, filed on Sep. 30, 2002, now abandoned.

(60) Provisional application No. 60/326,320, filed on Oct. 1, 2001.

(51) Int. Cl.
| | |
|---|---|
| *C12P 21/00* | (2006.01) |
| *C40B 30/04* | (2006.01) |
| *C40B 40/02* | (2006.01) |
| *G01N 33/554* | (2006.01) |
| *C12N 15/10* | (2006.01) |
| *C12N 15/85* | (2006.01) |

(52) U.S. Cl.
CPC .......... *G01N 33/554* (2013.01); *C12N 15/1037* (2013.01); *C12N 15/85* (2013.01); *C12N 2795/00043* (2013.01); *C12N 2800/108* (2013.01); *C12N 2830/002* (2013.01); *C12N 2840/20* (2013.01); *C40B 40/02* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 5,223,409 A | 6/1993 | Ladner et al. | |
| 5,354,847 A | 10/1994 | Liu et al. | |
| 5,643,745 A | 7/1997 | Stuart | |
| 5,658,727 A | 8/1997 | Barbas et al. | |
| 5,695,941 A | 12/1997 | Brent et al. | |
| 5,723,323 A | 3/1998 | Kauffman et al. | |
| 5,789,208 A | 8/1998 | Sharon | |
| 5,869,250 A | 2/1999 | Cheng et al. | |
| 5,888,732 A | 3/1999 | Harley et al. | |
| 6,074,853 A | 6/2000 | Pati et al. | |
| 6,132,970 A | 10/2000 | Stemmer | |
| 6,207,442 B1 | 3/2001 | Raymond | |
| 6,291,242 B1 | 9/2001 | Stemmer | |
| 6,297,053 B1 | 10/2001 | Stemmer | |
| 6,300,065 B1 | 10/2001 | Kieke et al. | |
| 6,406,863 B1 | 6/2002 | Zhu et al. | |
| 6,410,246 B1 | 6/2002 | Zhu et al. | |
| 6,410,271 B1 | 6/2002 | Zhu et al. | |
| 6,423,538 B1 | 7/2002 | Wittrup et al. | |
| 6,461,863 B1 | 10/2002 | Jarvis | |
| 6,610,472 B1 | 8/2003 | Zhu et al. | |
| 6,653,443 B2 | 11/2003 | Zhang et al. | |
| 6,696,251 B1 | 2/2004 | Wittrup et al. | |
| 6,699,658 B1 | 3/2004 | Wittrup et al. | |
| 7,465,787 B2 | 12/2008 | Wittrup et al. | |
| 7,700,302 B2 | 4/2010 | Hua et al. | |
| 2003/0165988 A1 | 9/2003 | Hua et al. | |
| 2003/0186374 A1 | 10/2003 | Hufton et al. | |
| 2007/0059308 A1 | 3/2007 | Hua et al. | |
| 2010/0124764 A1 | 5/2010 | Hufton et al. | |

(Continued)

FOREIGN PATENT DOCUMENTS

| | | |
|---|---|---|
| EP | 0120694 A2 | 10/1984 |
| WO | WO-9928502 A1 | 6/1999 |

(Continued)

OTHER PUBLICATIONS

Aslam et al., "Proteases from Schistosoma mansoni cercariae cleave IgE at solvent exposed interdomain regions", Mol. Immunol, 45:567-574 (2008).

Battersby et al., "Affinity-reversed-phase liquid chromatography assay to quantitate recombinant antibodies and antibody fragments in fermentation broth", J. Chromatogr A., 927:61-76 (2001).

Chang et al., "Novel arrangement of immunoglobulin variable domains: X-ray crystallographic analysis of the lambda-chain dimer Bence-Jones protein Loc.", Biochemistry, (24):4890-4897, (1985).

Cheetham et al., "Crystal structures of a rat anti-CD52 (CAMPATH-1) therapeutic antibody Fab fragment and its humanized counterpart", J Mol Biol, 284:85-99 (1998).

(Continued)

*Primary Examiner* — Michael Burkhart
(74) *Attorney, Agent, or Firm* — Wolf, Greenfield & Sacks, P.C.

(57) ABSTRACT

A eukaryotic expression vector capable of displaying a multi-chain polypeptide on the surface of a host cell is provided, such that the biological activity of the multi-chain polypeptide is exhibited at the surface of the host cell. Such a vector allows for the display of complex biologically active polypeptides, e.g., biologically active multi-chain polypeptides such as immunoglobulin Fab fragments. The present invention describes and enables the successful display of a multi-chain polypeptide on the surface of a eukaryotic host cell. Preferred vectors are described for expressing the chains of a multi-chain polypeptide in a host cell separately and independently (e.g., under separate vector control elements, and/or on separate expression vectors, thus forming a matched vector set). The use of such matched vector sets provides flexibility and versatility in the generation of eukaryotic display libraries, for example the ability to generate and to display multi-chain polypeptides by combining and recombining vectors that express variegations of the individual chains of a multi-chain polypeptide. Entire repertoires of novel chain combinations can be devised using such vector sets.

18 Claims, 22 Drawing Sheets

(56) References Cited

U.S. PATENT DOCUMENTS

| | | | |
|---|---|---|---|
| 2011/0009280 A1 | 1/2011 | Hufton et al. | |
| 2011/0190159 A1 | 8/2011 | Hufton et al. | |
| 2011/0281360 A1 | 11/2011 | Hufton et al. | |
| 2011/0281761 A1* | 11/2011 | Hufton et al. | 506/9 |

FOREIGN PATENT DOCUMENTS

| | | |
|---|---|---|
| WO | WO-9936569 A1 | 7/1999 |
| WO | WO-9950461 A1 | 10/1999 |
| WO | WO-0179229 A2 | 10/2001 |
| WO | WO 02/00729 A2 | 1/2002 |
| WO | WO 02/46400 A2 | 6/2002 |
| WO | WO 03/106639 A2 | 12/2003 |

OTHER PUBLICATIONS

Ely et al., "Three-dimensional structure of a hybrid light chain dimer: protein engineering of a binding cavity", Mol. Immunol., 27(2):101-114 1990).

Gollogly et al., "Fine structure of three different anti-fluorescein combining sites: induced circular dichroism of hapten bound to autologous and heterologous recombinants", J. Immunol., 117(1):180-6 (1976).

Hamers-et al, "Naturally occurring antibodies devoid of light chains", Nature, 363:446-8 (1993).

Hanson et al., "Mcg in 2030: new techniques for atomic position determination of immune complexes", J. Mol. Recognit., 15:297-305 (2002).

Jiang et al, "Interaction between glycosaminoglycans and immunoglobulin light chains", Biochemistry, 28;36(43):13187-13194 (1997).

Jokiranta et al., "Nephritogenic lambda light chain dimer: a unique human miniautoantibody against complement factor H[1]", J. Immunol., 15;163(8):4590-4596 (1999).

Kirkpatrick et al., "Heavy chain dimers as well as complete antibodies are efficiently formed and secreted from Drosophila via a BiP—mediated pathway", J. Biol Chem., 270(34):19800-19805 (1995).

Kohler et al., "Different ways to modify monoclonal antibodies", Med Oncol Tumor Pharmacother,1(4):227-233 (1984).

Lancet et al., "Hapten-induced allosteric transition in the light chain dimer of an immunoglobulin", Nature, 269(5631):827-829 (1977).

Ledbetter et al., "An immunoglobulin light chain dimer with CD4 antigen specificity", Mol. Immunol, 24(12):1255-1261(1987).

McColl et al., "Antibodies to synovial antigens in recent-onset rheumatoid arthritis", Arthritis Rheum., 38(10):1418-1428 (1995).

Nishimura et al., "Recombinant light chain of human monoclonal antibody HB4C5 as a potentially useful lung cancer-targeting vehicle", Hum Antibodies, 9:111-114 (1999).

Pavlinkova et al., "Site-specific photobiotinylation of immunoglobulins, fragments and light chain dimmers", J. Immunol Methods, 201(1):77-88 (1997).

Price et al., "Allergy to rabbits. I. Specificity and non-specificity of RAST and crossed-radioimmunoelectrophoresis due to the presence of light chains in rabbit allergenic extracts", Allergy, 41(8):603-612 (1986).

Ramsland et al., "Crystal structures of human antibodies: a detailed and unfinished tapestry of immunoglobulin gene products", J Mol Recognit., 15:248-259 (2002).

Schiffer et al., "Formation of an infinite beta-sheet arrangement dominates the crystallization behavior of lambda-type antibody light chains", J Mol Biol., 186(2):475-478 (1985).

Stevens et al., "Dual conformations of an immunoglobulin light-chain dimer: heterogeneity of antigen specificity and idiotope profile may result from multiple variable-domain interaction mechanisms", Proc Natl Acad Sci U S A., 8(18):6895-6899 (1988).

Szynol et al., "Bactericidal effects of a fusion protein of llama heavy-chain antibodies coupled to glucose oxidase on oral bacteria", Antimicrob Agents Chemother, 48(9):3390-3395 (2004).

Terada et al., "Fate of the mutated IgG2 heavy chain: lack of expression of mutated membrane-bound IgG2 on the B cell surface in selective IgG2 deficiency", International Immunology, 13(2):249-256 (2000).

Thiagarajan et al., "Monoclonal antibody light chain with prothrombinase activity", Biochemistry, 39(21):6459-6465 (2000).

Yuriev at al., "Mcg light chain dimer as a model system for ligand design: a docking study", J Mol Recognit, (5)331-340 (2002).

Zidovetski et al., "Effect of interchain disulfide bond on hapten binding properties of light chain dimer of protein 315", Proc Natl Acad Sci U S A., (11):5848-5852 (1979).

European Search Report dated Sep. 4, 2007 from European Application No. EP 02766425.9.

Chestnut et al., Journal of Immunological Methods 193 (1996) 17-27.

Grabherr et al., Trends in Biotechnology vol. 19 No. 6 Jun. 2001.

Supplemental European Search Report received in EP Application No. 02766425.9, mailed Nov. 22, 2005.

Oldenburg, K.R. et al. "Recombination-Mediated PCR-Directed Plasmid Construction In Vivo in Yest", Nucleic Acids Research vol. 25, No. 2, pp. 451-452, 1997.

Boder, E. and Wittrup, K., "Yeast Surface Display for Screening combinatiorial Polypeptide Libraries", Nature Biotechnology, vol. 15, pp. 553-557, 1997.

Boder, E. and Wittrup, K., "Yeast Surface Display for Directed Evolution of Protein Expression Affinity, and Stability", Methods in Enzymology., vol. 328, pp. 430-444, 2000.

Caren, R. et al., "Efficient Sampling of Protein Sequence Space for Multiple Mutants", Biotechnology, vol. 12, pp. 517-520, 1994.

Cherry, J.R. et al., "Directed Evolution of a Fungal Peroxidase", Nature Biotechnology, vol. 17, pp. 379-384, 1999.

Cho, B.K et al., "A Yeast Surface Display System for the Discovery of Ligands that Trigger Cell Activation", Journal of Immunological Methods, vol. 220, pp. 179-188, 1998.

Griffiths, et al., "Isolation of High Affinity Human Antibodies Directly from Large Synthetic Repertories", The EMBO Journal, vol. 13, No. 14, pp. 3245-3260, 1994.

Moerschell, R.P. et al., "Transformation of Yeast Directly with Synthetic Oligonucleotides", Methods Enzymol., pp. 362-369, 1991.

Sblattero, D. and Bradbury, A., "Exploiting Recombination in Single Bacteria to Make Large Phage Antibody Libraries", Nature Biotechnology, vol. 18, pp. 75-80, 2000.

Shusta, E.V. et al., "Directed Evolution of a Stable Scaffold for T-Cell Receptor Engineering", Nature Biotechnology, vol. 18, pp. 754-759, 2000.

Storici, F. and Lewis, K.L., "In Vivo Site-Directed Mutagenesis Using Oligonucleotides", Nature Biotechnology, vol. 19, pp. 773-776, 2001.

VanAntwerp, J. and Wittrup, K.D., "Fine Affinity Discrimination by Yeast Surface Display and Flow Cytometry", Biotechnol. Prog., vol. 16, pp. 31-37, 2000.

U.S. Appl. No. 10/462,518, filed Jun. 16, 2003.

Boder, et al., "Directed evolution of antibody fragments with monovalent femtomolar antigen-binding affinity," Proc. Natl. Acad. Sci. USA, vol. 97, No. 20, pp. 10701-10705 (2000).

Boeke et al., "A positive selection for mutants lacking orotidine-5'-phosphate decarboxylase activity in yeast: 5-fluoro-orotic acid resistance," Mol. Gen Genet., vol. 197 pp. 345-346, (1984).

Griffiths et al., "Isolation of high affinity human antibodies directly from large synthetic repertoires," EMBO J., vol. 13, No. 14, pp. 3245-3260, (1994).

Soderlind et al., "Recombining germline-derived CDR sequences for creating diverse single-framework antibody libraries," Nature Biotechnology, vol. 18, pp. 852-856, (2000).

Supplementary European Search Report received in application No. EP 03 73 4584, mailed on Jan. 2, 2006.

Abbas et al., Cellular and Molecular Immunology, 2nd Ed. W.B. Saunders Company. Philadelphia, PA. 1994:419-22.

Abbas et al., Cellular and Molecular Immunology, 4th Ed. W.B. Saunders Company. 2000:43. Dyax Exhibits 1025 and 1063.

Adimab Exhibit 2007. Smith, Homologous recombination near and far from DNA breaks: alternative roles and contrasting views. Annu Rev Genet. 2001;35:243-74.

Adimab Exhibit 2009. Sauer, Inducible gene targeting in mice using the Cre/lox system. Methods. Apr. 1998;14(4):381-92.

Adimab Exhibit 2010. WO 03/029456 A1 published Apr. 10, 2003.

(56) References Cited

OTHER PUBLICATIONS

Adimab Exhibit 2012. EP 1438400 B1 published Jun. 17, 2009.
Adimab Exhibit 2017. Swers et al., Shuffled antibody libraries created by in vivo homologous recombination and yeast surface display. Nucleic Acids Res. Feb. 20, 2004;32(3):e36. 8 pages.
Adimab Exhibit 2026. U.S. Appl. No. 09/703,399, filed Oct. 31, 2000. (See also Dyax Exhibit 1030.).
Adimab Exhibit 2028. Reissue U.S. Appl. No. 13/213,302, filed Aug. 19, 2011.
Adimab Exhibit 2030. U.S. Appl. No. 10/262,646, filed Sep. 30, 2002 (See also Dyax Exhibit 1067).
Adimab Exhibit 2031. U.S. Appl. No. 60/326,320, filed Oct. 1, 2001 (Also Dyax Exhibit 1068.).
Adimab Exhibit 2032. U.S. Appl. No. 11/593,957, filed Nov. 6, 2006.
Adimab Exhibit 2033. U.S. Appl. No. 10/360,828, filed Feb. 7, 2003.
Adimab Exhibit 2034. U.S. Appl. No. 10/133,978, filed Apr. 25, 2002.
Adimab Exhibit 2035. U.S. Appl. No. 10/072,301, filed Feb. 8, 2002.
Adimab Exhibit 2036. U.S. Appl. No. 10/071,866, filed Feb. 8, 2002.
Adimab Exhibit 2037. U.S. Appl. No. 12/625,337, filed Nov. 24, 2009, including Preliminary Amendment (See also Dyax Exhibit 1002).
Adimab Exhibit 2040. Hua et al., Minimum length of sequence homology required for in vivo cloning by homologous recombination in yeast. Plasmid. 1997;38(2):91-6.
Adimab Exhibit 2045. US 7,138,496 B2 issued Nov. 21, 2006.
Adimab Exhibit 2046. US 7,005,503 B2 issued Feb. 28, 2006.
Adimab Exhibit 2052. US 2003/0232395 A1 published Dec. 18, 2003 (U.S. Appl. No. 10/462,518).
Adimab Exhibit 2054. Raymond et al., General method for plasmid construction using homologous recombination. Biotechniques. Jan. 1999;26(1):134-41.
Adimab Exhibit 2056. US 6,027,910 published Feb. 22, 2000.
Adimab Exhibit 2058. WO 94/18330 A1 published Aug. 18, 1994.
Adimab Exhibit 2059. US 6,114,147 issued Sep. 5, 2000.
Adimab Exhibit 2060. Schreuder et al., Targeting of a heterologous protein to the cell wall of *Saccharomyces cerevisiae*. Yeast. Apr. 1993;9(4):399-409.
Adimab Exhibit 2061. Imai et al., The fission yeast mating pheromone P-factor: its molecular structure, gene structure, and ability to induce gene expression and G1 arrest in the mating partner. Genes Dev. Feb. 1, 1994;8(3):328-38.
Adimab Exhibit 2062. Cappellaro et al., Mating type-specific cell-cell recognition of *Saccharomyces cerevisiae*: cell wall attachment and active sites of a- and alpha-agglutinin. EMBO J. Oct. 17, 1994;13(20):4737-44.
Adimab Exhibit 2063. Van Der Vaart et al., Comparison of cell wall proteins of *Saccharomyces cerevisiae* as anchors for cell surface expression of heterologous proteins. Appl Environ Microbiol. Feb. 1997;63(2):615-20.
Adimab Exhibit 2064. Murai et al., Construction of a starch-utilizing yeast by cell surface engineering. Appl Environ Microbiol. Apr. 1997;63(4):1362-6.
Adimab Exhibit 2065. Ueda et al., Cell surface engineering of yeast: construction of arming yeast with biocatalyst. J Biosci Bioeng. 2000;90(2):125-36.
Adimab Exhibit 2067. Boder et al., Yeast surface display system for antibody engineering. Immunotechnology. 1996; 2: Abstract 283.
Adimab Exhibit 2071. US 7,208,293 B2 issued Apr. 24, 2007.
Adimab Exhibit 2072. WO 94/01567 A1 published Jan. 20, 1994.
Adimab Exhibit 2074. Hendershot et al., Chapter 17: Immunoglobulin assembly and secretion. Molecular Biology of B Cells. Elsevier Science 2004:261-273.
Adimab Exhibit 2079. Reissue U.S. Appl. No. 13/300,340, filed Nov. 18, 2011.
Adimab Exhibit 2080. Reissue U.S. Appl. No. 13/300,308, filed Nov. 18, 2011.
Adimab Exhibit 2085. Patel et al., Parallel selection of antibody libraries on phage and yeast surfaces via a cross-species display. Protein Eng Des Sel. Sep. 2011;24(9):711-9. Epub Jul. 12, 2011.
Adimab Exhibit 2086. Struhl et al., High-frequency transformation of yeast: autonomous replication of hybrid DNA molecules. Proc Natl Acad Sci U S A. Mar. 1979;76(3):1035-9.
Adimab Exhibit 2090. Schöndorf et al., Characterization of the complete genome of the Tupaia (tree shrew) adenovirus. J Virol. Apr. 2003;77(7):4345-56.
Adimab Exhibit 2093. Continuation of Reissue U.S. Appl. No. 13/213,302, filed Sep. 30, 2011.
Adimab Exhibit 2094. Davison et al., Genetic content and evolution of adenoviruses. J Gen Virol. Nov. 2003;84(Pt 11):2895-908.
Alberts et al., Molecular Biology of the Cell, 3rd Ed. Garland Publishing. New York, NY. 1994:441, 486, 1011-2, 1206-7, 1228, 1230-1.
Barbas et al., Molecular profile of an antibody response to HIV-1 as probed by combinatorial libraries. J Mol Biol. Apr. 5, 1993;230(3):812-23.
Boder et al., Optimal screening of surface-displayed polypeptide libraries. Biotechnol Prog. Jan.-Feb. 1998;14(1):55-62. Dyax Exhibit 1007.
Cattaneo et al., The selection of intracellular antibodies. Trends Biotechnol. Mar. 1999;17(3):115-21.
Chang et al. A general method for facilitating heterodimeric pairing between two proteins: application to expression of alpha and beta T-cell receptor extracellular segments. Proc Natl Acad Sci U S A. Nov. 22, 1994;91(24):11408-12.
Extended European Search Report dated Jul. 28, 2009 from European Application No. 09007767.8.
Crameri et al., Cloning *Aspergillus fumigatus* allergens by the pJuFo filamentous phage display system. Int Arch Allergy Immunol. May 1996;110(1):41-5.
Crameri et al., Display of biologically active proteins on the surface of filamentous phages: a cDNA cloning system for selection of functional gene products linked to the genetic information responsible for their production. Gene. Dec. 27, 1993;137(1):69-75.
De Haard et al., A large non-immunized human Fab fragment phage library that permits rapid isolation and kinetic analysis of high affinity antibodies. J Biol Chem. Jun. 25, 1999;274(26):18218-30.
De Kruif et al., Leucine zipper dimerized bivalent and bispecific scFv antibodies from a semi-synthetic antibody phage display library. J Biol Chem. Mar. 29, 1996;271(13):7630-4.
Den et al., A bidirectional phage display vector for the selection and mass transfer of polclonal antibody libraries. J Immunol Methods. Jan. 1, 1999;222(1-2):45-57.
Doupnik et al., The inward rectifier potassium channel family. Curr Opin Neurobiol. Jun. 1995;5(3):268-77.
Dyax Exhibit 1002: U.S. Appl. No. 12/625,337, filed Nov. 24, 2009 (See also Adimab Exhibit 2037).
Dyax Exhibit 1013: Yeung et al., *Biotechnol Prog.*, 18(2):212-220 (2002).
Dyax Exhibit 1014: Orr et al., *Biotechnol Prog.*, 19(2):631-8 (2003).
Dyax Exhibit 1015: Griffin et al., *J Immunol.*, 164(9):4433-42 (2000).
Dyax Exhibit 1017: Brophy et al., *J Immunol Methods*, 272(1-2):235-46 (2003).
Dyax Exhibit 1018: Starwalt et al., *Protein Eng.*, 16(2):147-56 (2003).
Dyax Exhibit 1019: Van den Beucken et al., *FEBS Lett.*, 546(2-3):288-94 (2003).
Dyax Exhibit 1023: Swers et al. *Nucleic Acids Research*, 32:e36 (2004).
Dyax Exhibit 1024: Swers et al. *Molecular Biotechnology*, 47:57-69 (2011).
Dyax Exhibit 1026: Lewin, *Genes V*, p. 99, Oxford University Press, 1994.
Dyax Exhibit 1027 and 1027A: Dranginis et al., *Microbiol Mol Biol Rev.*, 71(2):282-94 (2007).
Dyax Exhibit 1028: Sharifmoghadam et al., *FEBS Lett.*, 580:4457-4462 (2006).
Dyax Exhibit 1029: WO 2002/055718 A2 published Jul. 18, 2002.
Dyax Exhibit 1030: Specification of U.S. Appl. No. 09/703,399, filed Oct. 31, 2000. (See also Adimab Exhibit 2026.).
Dyax Exhibit 1031: Ma et al., *Gene*, 58(2-3):201-16 (1987).
Dyax Exhibit 1032: Wood et al., *Nature*, 314(6010):446-9 (1985).

(56) References Cited

OTHER PUBLICATIONS

Dyax Exhibit 1033: Weaver-Feldhaus et al., *FEBS Lett.*, 564(1-2):24-34 (2004).
Dyax Exhibit 1034: Shen et al., *J Biol Chem.*, 276(19):15768-75 (2001).
Dyax Exhibit 1035: Ma et al., *Mol. Immunol.*, 27(7):623-630 (1990).
Dyax Exhibit 1036: Colby et al., *J. Mol. Biol.*, 342:901-912 (2004).
Dyax Exhibit 1037: U.S. Patent No. 4,946,778 issued Aug. 7, 1990.
Dyax Exhibit 1038: Hamilton et al., *Current Opinion in Biotechnology*, 18:387-392 (2007).
Dyax Exhibit 1039: Bird et al., *Science*, 242:423-426 (1988). [Ex. 1039].
Dyax Exhibit 1049: Sambrook et al., "*Molecular Cloning: A Laboratory Manual*," at p. 17.4, $2^{nd}$ ed., Cold Spring Harbor Laboratory Press, 1989.
Dyax Exhibit 1057: Karu, et al., "*Recombinant Antibody Technology*," Figure 1, Institute for Laboratory Animal Research Journal (Online Issue) vol. 37(3), (1995).
Dyax Exhibit 1060: Souriau et al., *Expert Opin. Biol. Ther.*, 2001, 1(5):845-855.
Dyax Exhibit 1062: Hua et al., *Gene*, 1998, 215:143-152.
Dyax Exhibit 1064: Burke et al., Methods in Yeast Genetics, 2000 edition, Cold Spring Harbor Laboratory Press, pp. 40-41.
Dyax Exhibit 1066: Alberts et al., Molecular Biology of the Cell, 3th edition, Garland publishing, Inc. New York & London, p. 320.
Dyax Exhibit 1067: U.S. Appl. No. 10/262,646, filed Sep. 30, 2002. (See also Adimab Exhibit 2030).
Dyax Exhibit 1068: U.S. Appl. No. 60/326,320, filed Oct. 1, 2001 (Also Adimab Exhibit 2031).
Dyax Exhibit 1070: Marks et al., *J. Mol. Biol.*, 1991, 222:581-597.
Dyax Exhibit 1071: Abbas et al., Cellular and Molecular Immunology, 4th edition, W.B. Saunders Co., pp. 125-133.
Dyax Exhibit 1077: Woods and Gietz, High-Efficiency Transformation of Plasmid DNA into Yeast, Methods in Molecular Biology, vol. 177, Two-Hybrid Systems: Methods and Protocols, Humana Press, Inc. 2001: 85-97.
Dyax Exhibit 1079: US Patent Application Publication 2001/0037016 A1 published Nov. 1, 2001.
Dyax Exhibit 1080: US Patent Application Publication 2002/0026653 A1 published Feb. 28, 2002.
Dyax Exhibit 1081: US Patent Application Publication 2002/0037280 A1 published Mar. 28, 2002.
Dyax Exhibit 1082: Alberts et al., Molecular Biology of The Cell, Garland Science, 2002, pp. 293-294.
Dyax Exhibit 1083: Alberts et al., Molecular Biology of The Cell, Garland Science, 2002, pp. 540-541.
Dyax Exhibit 1087: In-Fusion SMARTer Directional cDNA Library Construction Kit User Manual, Clontech, Jun. 2011.
Dyax Exhibit 1088: US Patent Application Publication US 2003/0091995 published May 15, 2003.
Dyax Exhibit 1089: US Patent Application Publication US 2001/0041333 published Nov. 15, 2001.
Dyax Exhibit 1090: Sheets, et al., Efficient construction of a large nonimmune phage antibody library: The production of high-affinity human single-chain antibodies to protein antigens. *Proc Natl. Acad. Sci. USA*, vol. 95, pp. 6157-6162, May 1998.
Dyax Exhibit 1092: Shusta, et al., "Yeast Polypeptide Fusion Surface Display Levels Predict Thermal Stability and Soluble Secretion Efficiency," *J. Mol. Biol.* vol. 292, pp. 949-956, 1999.
Dyax Exhibit 1093: Boder et al., Yeast Surface Display of a Noncovalent MHC Class II Heterodimer Complexed with Antigenic Peptide. Biotechnol Bioeng. Nov. 20, 2005;92(4):485-91. Wiley Interscience, www.interscience.wiley.com., DOI 1002/bit.20616, Sep. 22, 2005.
Dyax Exhibit 1094: Pepper, et al., "A Decade of Yeast Surface Display Technology: Where Are We Now?" Combinatorial Chemistry & high Throughput Screening, vol. 11, pp. 127-134, 2008.
Dyax Exhibit 1095: Alberts et al., Molecular Biology of The Cell, Garland Science, 2002, pp. 275-277.

Dyax Exhibit 1096: Lin, et al., Display of a Functional Hetero-oligomeric Catalytic Antibody on the Yeast Cell Surface, Appl Microbiol Biotechnol, 2003, 62: 226-232.
Dyax Exhibit 1097: Hubberstey and Wildeman, Use of Interplasmid Recombination to Generate Stable Selectetable Markers for Yeast Transformation: application to Studies of Actin Gene Control. Genome. Oct. 1990;33(5):696-706.
Dyax Exhibit 1098: Dielbandhoesing et al., Specific Cell Wall Proteins Confer Resistance to Nisin upon Yeast Cells. Applied and Environmental Microbiology. Oct. 1998;64(10):4047-52.
Dyax Exhibit 1099: Sed1p [*Saccharomyces cerevisiae* S288c] Protein NCBI. Apr. 26, 2011.
Dyax Exhibit 1100: Tip1p [*Saccharomyces cerevisiae* S288c] Protein NCBI. Jul. 1, 2011.
Dyax Exhibit 1102: Tsubouchi and Roder, Budding yeast Hed1 down regulates the mitotic recombination machinery when meiotic recombination is impaired. Dept. of Molecular, Cellular and Developmental Biology, Hower Hughes Medical Institute, Yale University, 2006. Genes Dev. Jul. 1, 2006;20(13):1766-75.
Dyax Exhibit 1105: Manivasakam and Schiestl, "High Efficiency Transformation of *Saccharomyces cerevisea* by Electroporation," Nucleic Acids Research, vol. 21, No. 18 pp. 4414-4415, 1993.
Dyax Exhibit 1106: Kranz and Voss, "Restricted Reassociation of heavy and light chains from hapten-specific monoclonal antibodies," Proc. Natl. Acad. Sci. USA, vol. 78 No. 9, pp. 5807-5811, Sep. 1981.
Dyax Exhibit 1108: Stemmer, William P.C., "DNA Shuffling by Random Fragmentation and Reassembly: in vitro Recombination for Molecular Evolution," Proc. Nation. Acad. Sci. USA, vol. 91, pp. 10747-10751, Oct. 1994.
Falco et al., Homologous Recombination between Episomal Plasmids and Chromosomes in Yeast. Genetics. Dec. 1983;105(4):843-56.
Fields et al., The two-hybrid system: an assay for protein-protein interactions. Trends Genet. Aug. 1994;10(8):286-92.
Foote et al., Breaking the affinity ceiling for antibodies and T cell receptors. Proc Natl Acad Sci U S A. Sep. 26, 2000;97(20):10679-81.
Frazer et al., Immunoglobulins: structure and function. In Fundamental Immunology, 4th Ed. William E. Paul, Editor. Lippincot-Raven. 1999:41-3, 51-2.
Holler et al., In vitro evolution of a T cell receptor with high affinity for peptide/MHC. Proc Natl Acad Sci U S A. May 9, 2000;97(10):5387-92. Dyax Exhibit 1010.
Hoogenboom et al., Natural and designer binding sites made by phage display technology. Immunol Today. Aug. 2000;21(8):371-8. Adimab Exhibit 2075.
Hoogenboom, Designing and optimizing library selection strategies for generating high-affinity antibodies. Trends Biotechnol. Feb. 1997;15(2):62-70.
Horwitz et al., Secretion of functional antibody and Fab fragment from yeast cells. Proc Natl Acad Sci U S A. Nov. 1988;85(22):8678-82. Adimab Exhibit 2051.
Ibragimova et al., A strategy for construction of industrial strains of distiller's yeast. Biotechnol Bioeng. May 5, 1995;46(3):285-90.
Invitrogen 2000 Catalog, p. 140.
Janeway et al., Immunobiology: The Immune System in Health and Disease. 1994. Current Biology, Ltd. Pages excerpted from Chapters 3 and 6. 6 pages total.
Kieke et al., High affinity T cell receptors from yeast display libraries block T cell activation by superantigens. J Mol Biol. Apr. 13, 2001;307(5)1305-15. Dyax Exhibit 1016.
Kieke et al., Isolation of anti-T cell receptor scFv mutants by yeast surface display. Protein Eng. Nov. 1997;10(11):1303-10. Dyax Exhibit 1005.
Kieke et al., Selection of functional T cell receptor mutants from a yeast surface-display library. Proc Natl Acad Sci U S A. May 11, 1999;96(10):5651-6. Dyax Exhibit 1008.
Kolonin et al., Interaction mating methods in two-hybrid systems. Methods Enzymol. 2000;328:26-46.
Kozono et al., Production of soluble MHC class II proteins with covalently bound single peptides. Nature. May 12, 1994;369(6476):151-4.

(56) References Cited

OTHER PUBLICATIONS

Krapivinsky et al., The G-protein-gated atrial K+ channel IKACh is a heteromultimer of two inwardly rectifying K(+)—channel proteins. Nature. Mar. 9, 1995;374(6518):135-41.

Lederman et al., A single amino acid substitution in a common African allele of the CD4 molecule ablates binding of the monoclonal antibody, OKT4. Mol Immunol. Nov. 1991;28(11):1171-81.

Lee et al., Expression specificity of the mouse exonuclease 1 (mExo1) gene. Nucleic Acids Res. Oct. 15, 1999;27(20):4114-20.

Li et al., beta-Endorphin omission analogs: dissociation of immunoreactivity from other biological activities. Proc Natl Acad Sci U S A. Jun. 1980;77(6):3211-4.

Liu et al., Rapid construction of recombinant DNA by the univector plasmid-fusion system. Methods Enzymol. 2000;328:530-49. Adimab Exhibit 2005. Dyax Exhibit 1061.

Lundblad et al., Manipulation of Cloned Yeast DNA. Curr Protoc Mol Biol. 1997; Unit 13.10. 13.10.1-13.10.14. Published online May 1, 2001.

Lundblad et al., Manipulation of Plasmids from Yeast Cells. Curr Protoc Mol Biol. 1997; Unit 13.9. 13.9.1-13.9.6. Published online May 1, 2001.

Matsumura et al., In vitro peptide binding to soluble empty class I major histocompatibility complex molecules isolated from transfected *Drosophila melanogaster* cells. J Biol Chem. Nov. 25, 1992;267(33):23589-95.

McCafferty et al., Phage antibodies: filamentous phage displaying antibody variable domains. Nature. Dec. 6, 1990;348(6301):552-4.

Mercier et al., Rapid detection of the sacsin mutations causing autosomal recessive spastic ataxia of Charlevoix-Saguenay. Genet Test. 2001 Fall;5(3):255-9.

Moll eta l., Designed heterodimerizing leucine zippers with a ranger of pls and stabilities up to 10(-15) M. Protein Sci. Mar. 2001;10(3):649-55.

Norderhaug et al., Balanced expression of single subunits in a multisubunit protein, achieved by cell fusion of individual transfectants. Eur J Biochem. Jul. 2002;269(13):3205-10.

Ohara et al., Directional cDNA library construction assisted by the in vitro recombination reaction. Nucleic Acids Res. Feb. 15, 2001;29(4):E22.

Persic et al., An integrated vector system for the eukaryotic expression of antibodies or their fragments after selection from phage display libraries. Gene. Mar. 10, 1997;187(1):9-18.

Phizicky et al., Protein-protein interactions: methods for detection and analysis. Microbiol Rev. Mar. 1995;59(1):94-123.

Pogue et al., Gene dose-dependent maturation and receptor editing of B cells expressing immunoglobulin (Ig)G1 or IgM/IgG1 tail antigen receptors. J Exp Med. Mar. 20, 2000;191(6):1031-44. Adimab Exhibit 2014.

Proba et al., Antibody scFv fragments without disulfide bonds made by molecular evolution. J Mol Biol. Jan. 16, 1998;275(2):245-53.

Pu et al., Dimerization of leucine zippers analyzed by random selection. Nucleic Acids Res. Sep. 11, 1993;21(18):4348-55.

Pörtner-Taliana et al., In vivo selection of single-chain antibodies using a yeast two-hybrid system. J Immunol Methods. Apr. 21, 2000;238(1-2):161-72.

Rudikoff et al., Rudikoff S, Giusti AM, Cook WD, Scharff MD. Single amino acid substitution altering antigen-binding specificity. Proc Natl Acad Sci U S A. Mar. 1982;79(6):1979-83.

Sambrook et al., Molecular Cloning: A laboratory manual., 2nd Ed. 1989:1.19.

Santa Cruz Biotechnology catalog entry for antibodies sc-22104 and sc-33133. 2 pages. Printed Dec. 2007.

Schreuder et al., Immobilizing proteins on the surface of yeast cells. Trends Biotechnol. Apr. 1996;14(4):115-20. Adimab Exhibit 2004.

Silverman et al., Building larger YACs by recombination. Curr Protoc Hum Genet. 1995;Chapter 5:Unit 5.13. Published online May 1, 2001.

Tucker et al., Muscarine-gated K+ channel: subunit stoichiometry and structural domains essential for G protein stimulation. Am J Physiol. Jul. 1996;271(1 Pt 2):H379-85.

Ueda et al., Genetic immobilization of proteins on the yeast cell surface. Biotechnol Adv. Apr. 2000;18(2):121-40. Adimab Exhibit 2087.

Visintin et al., Selection of antibodies for intracellular function using a two-hybrid in vivo system. Proc Natl Acad Sci U S A. Oct. 12, 1999;96(21):11723-8.

Walhout et al., Gateway recombinational cloning: application to the cloning of large numbers of open reading frames or ORFeomes. Methods Enzymol. 2000;328:575-92. Adimab Exhibit 2006. Dyax Exhibit 1022.

Wang, Creating hybrid genes by homologous recombination. Dis Markers. 2000;16(1-2):3-13.

Willemsen et al., Grafting primary human T lymphocytes with cancer-specific chimeric single chain and two chain TCR. Gene Ther. Aug. 2000;7(16):1369-77.

Wojciechowicz et al., Cell surface anchorage and ligand-binding domains of the *Saccharomyces cerevisiae* cell adhesion protein alpha-agglutinin, a member of the immunoglobulin superfamily. Mol Cell Biol. Apr. 1993;13(4):2554-63.

Yang et al., CDR walking mutagenesis for the affinity maturation of a potent human anti-HIV-1 antibody into the picomolar range. J Mol Biol. Dec. 1, 1995;254(3):392-403.

Ye et al., Construction of an engineered yeast with glucose-inducible emission of green fluorescence from the cell surface. Appl Microbiol Biotechnol. Jul. 2000;54(1):90-6. Adimab Exhibit 2066.

Paper No. 528: Exhibit 2102: Stemmer, Rapid evolution of a protein in vitro by DNA shuffling. Nature. Aug. 4, 1994;370(6488):389-91.

Paper No. 530: Exhibit 2104: Van Den Beucken et al., Building novel binding ligands to B7.1 and B7.2 based on human antibody single variable light chain domains. J Mol Biol. Jul. 13, 2001;310(3): 591-601.

Paper No. 532: Exhibit 2106: De Haard et al.,. Creating and engineering human antibodies for immunotherapy. Adv Drug Deliv Rev. Apr. 6, 1998;31(1-2):5-31.

Paper No. 533: Exhibit: 2107: Hoogenboom et al., Antibody phage display technology and its applications. Immunotechnology. Jun. 1998;4(1):1-20.

Paper No. 534: Exhibit 2108: Joern et al., DNA shuffling. Methods Mol Biol. 2003;231:85-9.

Paper No. 544: Exhibit 1238: Crameri et al., Molecular evolution of an arsenate detoxification pathway by DNA shuffling. Nat Biotechnol. May 1997;15(5):436-8.

Paper No. 545: Exhibit 1239: Crameri et al., Improved green fluorescent protein by molecular evolution using DNA shuffling. Nat Biotechnol. Mar. 1996;14(3):315-9.

Paper No. 546: Exhibit 1240: Google Scholar Search: "molecular evolution of an arsenate detoxification pathway by dna shuffling". Dated Sep. 27, 2013.

Paper No. 547: Exhibit 1241: Kuchner et al., Directed evolution of enzyme catalysts. Trends Biotechnol. Dec. 1997;15(12):523-30.

Paper No. 548: Exhibit 1242: Arnold, Design by directed evolution. Accounts of Chemical Research. 1998;31(3):125-31.

Paper No. 557: Exhibit 2110: Oxford Dictionary of Biochemistry and Molecular Biology. Oxford University Press. 1997. p. 131.

Office Communication mailed Sep. 17, 2014 for U.S. Appl. No. 12/625,337.

* cited by examiner

MULTI-CHAIN EUKARYOTIC DISPLAY VECTORS AND USES THEREOF

RELATED APPLICATIONS

This application is a divisional of U.S. application Ser. No. 12/625,337, filed on Nov. 24, 2009, which is a continuation of U.S. application Ser. No. 10/262,646, filed on Sep. 30, 2002, now abandoned, which claims the benefit of U.S. Provisional Application No. 60/326,320, filed Oct. 1, 2001.

The entire teachings of the above applications are herein incorporated by reference.

BACKGROUND OF THE INVENTION

The development of phage display technology, whereby non-native (heterologous) polypeptides or proteins are expressed and anchored on the surface ("displayed") of a bacteriophage, is a powerful tool for identifying molecules possessing biological activities of interest, for example, peptide ligands that bind with high specificity and/or affinity to a given target molecule. Libraries of synthetic oligonucleotides can be cloned in frame into the coding sequence of genes encoding a phage surface protein, for example gene III or gene VIII of phage M13. These clones, when expressed, are "displayed" on the phage surface as a plurality, due to the variation in sequence of the oligonucleotides used, of peptide-capsid fusion proteins. These peptide display libraries are then screened for binding to target molecules, usually by affinity selection or "biopanning" (Ladner, R. et al., 1993; Kay et al., 1996; Hoogenboom, H. et al., 1997).

Phage display library screening is highly advantageous over other screening methods due to the vast number of different polypeptides (typically exceeding $1 \times 10^9$) that can be contained in a single phage display library. This allows for the screening of a highly diverse library in a single screening step. Display of small peptides or single chain proteins on phage is advantageous as long as intracellular processing or post-translational modification (of which phage or prokaryotic hosts are not capable) are not necessary or desired. For example, effective display of a heterologous polypeptide may require various post-translational modifications, intracellular structures, and a compliment of specialized enzymes and chaperone proteins that are necessary to transport, to glycosylate, to conform, to assemble, and to anchor the display polypeptide properly on the surface of the host cell; however, none of these processes can be accomplished by bacteriophage or prokaryotic cell processes.

For the display of more complex eukaryotic proteins, for example multi-chain polypeptides including immunoglobulins and functional fragments thereof (e.g., Fabs), or the extracellular domains of MHC molecules or T cell receptor molecules, there are additional problems to overcome: coordinated expression of the component chains at the levels of expression sufficient to produce multi-chain products, transport and secretion of each chain while still accomplishing association into a functional multi-chain polypeptide, and immobilization (anchoring) of at least one chain of the multi-chain polypeptide at the host cell surface (i.e., for display), while retaining the proper assembly and functionality outside the host cell of the multi-chain polypeptide product.

Display systems utilizing eukaryotic cells, such as yeast, have been reported for expressing and displaying single chain polypeptides (Boder, E. and Wittrup, K., 1998; Horwitz, A. et al., 1988; Kieke, M. et al., 1997; Kieke, M. et al., 1999; WO 94/18330; WO 99/36569), however the need exists for improved eukaryotic systems for the expression and functional display of multi-chain polypeptides, particularly immunoglobulins and fragments thereof. Moreover, there is a need in the art for polypeptide display in a system that harnesses the power of phage display and the processing advantages of eukaryotic host cells. For example, in contrast to phage display libraries, the maximum practical size, or "diversity", of a library that can be expressed in and displayed on the surface of a eukaryotic host cell is about $10^6$ to $10^7$.

These and other technical problems have obstructed the advance of biological tools and techniques useful for identifying novel molecules, which possess biological activities of interest. Because of these technical problems, there has been no report to date of materials or methods for the successful construction of a multi-chain eukaryotic display vector, of the successful display of a multi-chain polypeptide (such as an antibody or a Fab fragment) on the surface of a eukaryotic host cell (such as yeast), of the creation of a multi-chain polypeptide display library in eukaryotic host cells, or of the successful use of such libraries to detect and to isolate specific multi-chain polypeptides of interest (for example, on the basis of binding specificity or affinity for a target molecule).

SUMMARY OF THE INVENTION

These and other deficiencies in the art are overcome by the invention described herein, which provides improved display vectors, cells containing display libraries, and methods for the use of such libraries and vectors. Specifically, the present invention provides a eukaryotic expression vector capable of displaying a multi-chain polypeptide on the surface of a host cell such that a biological activity of the multi-chain polypeptide is exhibited at the surface of the host cell. Such a vector allows for the display of more complex biologically active polypeptides, e.g., biologically active multi-chain polypeptides, than can be obtained via conventional phage display technology.

The present invention relates to the display and isolation of biologically active polypeptides. Specifically, the present invention is directed to the design and use of novel multi-chain display vectors.

The present invention describes and enables the successful display of a multi-chain polypeptide on the surface of a eukaryotic host cell. Preferred vectors are described for expressing the chains of a multi-chain polypeptide in a host cell separately and independently (e.g., under separate vector control elements, and/or on, separate expression vectors, thus forming a matched vector set). The use of such matched vector sets provides a level of flexibility and versatility in the generation of display libraries, for example the ability to generate and to display multi-chain polypeptides by combining and recombining vectors that express a variety of the individual chains of a multi-chain polypeptide. Entire repertoires of novel chain combinations can be devised using such vector sets.

The invention further provides the ability to combine the power of phage display technology (with its ease of manipulation and magnitude of diversity) with the potential complexity and versatility of a multi-chain eukaryotic display vector (or vector set). The particular methods described herein permit a practitioner to efficiently transfer sequence information of a peptide library (or selected members of the library) between phage display and eukaryotic display systems, accomplished either through the physical transfer of the sequence information from one display vector to the other (using conventional genetic engineering techniques) or through the use of a novel dual display vector, operable in both eukaryotic display systems and phage display systems (which necessarily involve prokaryotic expression).

The present invention is directed to a novel vector, useful in a eukaryotic host cell to display a multi-chain polypeptide on the surface of the host cell such that a biological activity of the multi-chain polypeptide is exhibited at the surface of the host cell, e.g., the binding activity of a multi-chain polypeptide. Although one preferred embodiment of the vector of the present invention is that of a single replicable genetic package, the multi-chain eukaryotic display vector can exist as a single vector or as multiple independent vectors of a vector set. As used herein, "vector" refers to either a single vector molecule or a vector set. In one embodiment, the display vector is a shuttle vector, or more precisely a dual display vector, wherein the vector is capable of displaying a biologically active multi-chain polypeptide on the surface of a eukaryotic host cell transformed with that vector, or on the surface of a bacteriophage generated as a result of prokaryotic expression. In another aspect of the invention, the vector can exist as a vector set, wherein each chain of a multi-chain polypeptide is encoded on one of a matched pair of vectors such that when the vector pair is present in a single eukaryotic cell, the chains of the multi-chain polypeptide associate and the biological activity of the multi-chain polypeptide is exhibited at the surface of the eukaryotic cell.

The eukaryotic multi-chain display vector of the present invention comprises polynucleotides that encode polypeptide chains of the multi-chain polypeptide. A first polynucleotide encodes a first chain of the multi-chain polypeptide linked to an anchor protein. Other polynucleotides of the vector (or vector set) encode other chains of the multi-chain polypeptide. All of the polynucleotides of the display vector(s) are operably-situated in the display vector such that a host eukaryotic cell, transformed with the vector (or vector set), displays the multi-chain polypeptide on the surface of the host cell such that the biological activity of the multi-chain polypeptide is exhibited at the surface of the cell.

Preferably, the multi-chain polypeptide encoded by the multi-chain display vector(s) of the present invention exists as either a two-, three-, four-, or multi-chain polypeptide. More preferably, the multi-chain polypeptide is a two-chain or four-chain polypeptide comprised of two different chains. More preferably, the multi-chain polypeptide is selected from a group of multi-chain polypeptides consisting of T cell receptors, MHC class I molecules, MHC class II molecules, and immunoglobulin Fab fragments. More preferably, the multi-chain polypeptide is an IgA, IgD, IgE, IgG, IgM, or biologically active fragment thereof. Most preferably, the multi-chain polypeptide is a Fab fragment, wherein the first polynucleotide of the multi-chain display vector comprises a segment that encodes the $V_H$ and $C_H1$ domains of an Ig heavy chain, and a second polynucleotide comprises a segment that encodes an Ig light chain ($V_L$ and $C_L$ domains).

According to the present invention, a first polynucleotide encoding a first chain of the multi-chain polypeptide is linked to an anchor protein. Preferably, the anchor protein is a cell surface protein of a eukaryotic cell or a functional fragment thereof. More preferably, the anchor protein is α-agglutinin, a-agglutinin, Aga1p, Aga2p, or FLO1. As disclosed herein, linkage of the first chain polypeptide to an anchor protein can be achieved by a variety of molecular biology techniques. Preferably, the first polynucleotide encoding a first chain of the multi-chain polypeptide is expressed in a eukaryotic host cell as a first chain-anchor fusion protein; most preferably a first chain:Aga2p fusion protein.

In one embodiment, one or more of the chains of the multi-chain polypeptide expressed by the vector(s) in a host cell is linked to a reporter gene or tag. Preferably, the tag is an epitope tag selected from the group consisting of 6×His tag, HA tag, and myc tag. Most preferably, each chain of the multi-chain polypeptide is linked to a different tag.

Preferably, the multi-chain display vector(s) of the present invention provide cloning sites to facilitate transfer of the polynucleotide sequence(s) that encode the chains of the multi-chain polypeptide. Such cloning sites comprise restriction endonuclease recognition site (i.e., restriction sites) positioned to facilitate excision and insertion of polynucleotides that encode one or more chains of a multi-chain polypeptide. For example, restriction sites are preferably located at the 5' and 3' ends of the polynucleotide(s) that encode the chains of the multi-chain polypeptide. The vector of the present invention can contain only two restriction sites positioned at the ends of the polynucleotide segment that includes all segments encoding the chains of the multi-chain polypeptide, or, preferably, restriction sites occur at the ends of each polynucleotide segment encoding a chain of the multi-chain polypeptide (FIGS. 1 and 2). Preferably, each restriction endonuclease recognition site is a unique recognition site in the vector.

The vector (or vector set) of the present invention can be operable in a variety of eukaryotic host cells, and optionally can be operable in prokaryotic cells (e.g., bacteria). Preferably, the multi-chain display vector of the present invention is an animal cell display vector, a plant cell display vector, a fungus cell display vector, or a protist cell display vector. More preferably, the display vector is a yeast display vector. Most preferably, the yeast display vector is operable in *Saccharomyces cerevisiae*.

In another embodiment, the invention is directed to a method for using the vector (or vector set) described and taught herein for displaying a multi-chain polypeptide on the surface of a eukaryotic host cell, wherein the vector (or vector set) is introduced into the eukaryotic cell and the host cell is cultured under conditions suitable for expression, transportation, and association of the chains of the multi-chain polypeptide such that the biological activity of the multi-chain polypeptide is exhibited at the surface of the host cell. As described herein, the polynucleotides encoding the chains of the multi-chain polypeptide can be introduced into the host cell via one or more vectors. The mode of introducing the vector(s) into the host cell includes any of the methods for introducing genetic material into a cell known in the art. Preferred modes include such transformation techniques known in the art, including but not limited to electroporation, microinjection, viral transfer, ballistic insertion, and the like.

Another preferred mode for introducing eukaryotic multi-chain display vectors into a host cell includes the fusion of two haploid eukaryotic cells, each expressing at least one of the chains of the multi-chain polypeptide, to produce a diploid host cell expressing both (all) chains, such that the biological activity of the multi-chain polypeptide is exhibited at the surface of the resulting diploid host cell. For example, each of the two haploid cells can contain one (or more) of the vectors of a vector set (as described herein), such that the biological activity of the multi-chain polypeptide is exhibited at the surface of the diploid host cell resulting from the haploid/haploid fusion. Preferably, the haploid host cell pair is of opposite mating types, thus facilitating the fusion ("mating") of the two eukaryotic haploid cells.

Another object of the invention is directed to a eukaryotic host cell that exhibits at the surface of the cell the biological activity of a multi-chain polypeptide. As described herein, the eukaryotic host cell is preferably an animal cell, a plant cell, a fungus cell, or a protist cell. More preferably the eukaryotic host cell is a yeast cell. Preferably, the yeast host cell is selected from the genera *Saccharomyces, Pichia, Hansenula, Schizosaccharomyces, Kluyveromyces, Yarrowia*, and *Candida*. Most preferably, the eukaryotic host cell is *S. cerevisiae*. Eukaryotic host cells of the present invention can be of any genetic construct but are preferably haploid or diploid.

One embodiment of the present invention is directed to a eukaryotic haploid cell pair (preferably of opposite mating types) wherein the first haploid cell expresses at least a first polynucleotide encoding a first chain of a biologically active multi-chain polypeptide linked to an anchor protein, and the second haploid cell expresses at least a second polynucleotide encoding a second chain of the multi-chain polypeptide. As discussed above, fusion of this haploid cell pair results in a diploid cell that exhibits the biological activity of the multi-chain polypeptide at the surface of the cell.

The present invention is further directed to assemblages of the various embodiments described herein, which form novel libraries of multi-chain polypeptides or of the polynucleotides that encode them. Libraries of the present invention comprise a plurality of vectors that encode a multi-chain polypeptide such that the vector is operable in a eukaryotic host cell to direct expression and secretion of the chains of the multi-chain polypeptide, association of the chains such that the biological activity of the multi-chain polypeptide is constituted, and anchoring of at least one chain of the multi-chain polypeptide such that the biological activity of the multi-chain polypeptide is exhibited at the surface of the eukaryotic host cell. Preferably, the library of the present invention is comprised of library members that encode a multiplicity of different multi-chain polypeptides. Most preferably, the library is comprised of library members that encode a multiplicity of variant multi-chain polypeptides (designed and produced by the variegation of a multi-chain polypeptide template). Novel multi-chain library assemblages of the present invention include vector libraries, vector set libraries, host cell libraries, and host cell pair libraries as described and taught herein.

A related aspect of the present invention is directed to a method for transferring nucleic acid sequence information encoding a biologically active multi-chain polypeptide between a phage display vector and a eukaryotic display vector. One transfer method comprises inserting polynucleotide sequences encoding the chains of a multi-chain polypeptide obtained from a phage display vector into a eukaryotic multi-chain display vector as described and taught herein. Transfer of the nucleic acid sequence information encoding the chains of a multi-chain polypeptide can occur as a single transfer event, or can occur as separate and independent transfer events of nucleic acid sequence information encoding each of the chains of the multi-chain polypeptide. Similarly, the sequence information encoding each of the chains of a multi-chain polypeptide can be transferred from one display vector or from multiple different display vectors.

Another method for transferring nucleic acid sequence information encoding a biologically active multi-chain polypeptide between a phage display vector and a eukaryotic display vector (and converse to that just described) comprises inserting polynucleotide sequences encoding the chains of a multi-chain polypeptides obtained from a eukaryotic multi-chain display vector as described and taught herein into a phage display vector. The phage display-eukaryotic display transfer process of the present invention is bi-directional, i.e., it can occur from phage display vector to eukaryotic display vector or from eukaryotic display vector to phage display vector.

The transfer of nucleic acid sequence information between a phage display vector and the eukaryotic vector of the present invention can be achieved by a variety of genetic transfer methods known in the art (e.g., genetic engineering technology such as recombinant DNA technology). Preferred modes of transfer include techniques of restriction digestion, PCR amplification, or homologous recombination (e.g., see Liu, Q. et al., 2000; Walhout, A. et al., 2000).

The present invention is also directed to methods for detecting and isolating multi-chain polypeptides that exhibit a biological activity of interest to the practitioner. The methods of the present invention permit the detection of desirable interactions between multi-chain polypeptides and another molecular species, preferably protein-protein interactions, and more preferably interactions between multi-chain polypeptides and their ligands/substrates (i.e., target molecules). Preferably, the nature of this interaction comprises a non-covalent association (i.e., binding) between the molecular species, however the nature of the binding can be transient (e.g., enzyme-substrate binding) or of high affinity/avidity (e.g., as with affinity ligands useful in separations, diagnostics, and/or therapeutics).

In one embodiment, the method of the present invention is useful to screen a library of multi-chain polypeptides (displayed on the surface of a eukaryotic host cell) by detecting those members of the library that exhibit a biological activity of interest to the practitioner. In a particularly preferred embodiment, host cells, which display multi-chain polypeptides exhibiting the biological activity of interest, are isolated. Isolated host cells can then, optionally, undergo repeated rounds of screening, or otherwise be manipulated to characterize or to utilize the polypeptide sequence of the displayed multi-chain polypeptide. In addition, the screening method of the present invention can be combined with a (preliminary) phage display screen and transfer of the selected phage display isolates to the eukaryotic display system described herein for eukaryotic display screening.

In a further embodiment of the present invention, a library of multi-chain polypeptides displayed on the surface of a diploid eukaryotic host cell, wherein the diploid cell contains a multi-chain vector set as described and taught herein, can be screened to detect (and optionally to isolate) multi-chain polypeptides that exhibit a biological activity of interest to the practitioner. Preferably, the diploid eukaryotic host cell is the product of the fusion of a haploid eukaryotic host cell pair as described and taught herein. In one particularly preferred embodiment, screened diploid cells displaying a multi-chain polypeptide exhibiting a biological activity of interest can be isolated and then, optionally, undergo meiosis, whereby the daughter (haploid) cells express separate chains of the selected multi-chain polypeptide. Daughter cells can then, optionally, be fused with other haploid cells that express chains of a multi-chain polypeptide (e.g., other daughter cells from the same sub-population of isolated diploid cells), producing a recombination population of diploid eukaryotic host cells that display a multi-chain polypeptide on their surface. Additional rounds of screening and repeat recombination of the individual chains of the selected multi-chain polypeptide can be performed, and ultimately the polypeptide sequence of the displayed multi-chain polypeptide can be characterized or utilized as discussed above. Recombination of the selected haploid daughter cells can also be recombined (via cellular fusion) with other biased or non-biased eukaryotic display vectors to produce novel multi-chain display host cell libraries.

The eukaryotic display vector can be used to create a eukaryotic display library, such as a yeast display library, comprising a plurality of such eukaryotic display vectors. Preferably a plurality of eukaryotic display vectors will encode a heterogeneous population of multi-chain polypeptides, yielding a displayed repertoire of multi-chain polypeptides, e.g., at least $10^4$, preferably at least $10^5$, more preferably at least $10^6$, more preferably at least $10^7$, more preferably at least $10^8$, most preferably at least $10^9$ different polypeptides.

In particular embodiments of the invention, the anchor is a polypeptide operable as an anchor on the surface of a eukaryotic cell and operable as an anchor on the surface of a phage. In other embodiments, the anchor is a portion of a surface protein that anchors to the cell surface of a eukaryotic host cell and to the surface of a phage.

In preferred embodiments of the present invention, the anchor and one chain of the multi-chain polypeptide are expressed as a fusion protein. In other embodiments, the anchor and one chain of the multi-chain polypeptide become linked on expression via an indirect linkage, such as, preferably, a Jun/Fos linkage.

In another embodiment, the invention is directed to a method for displaying, on the surface of a eukaryotic host cell, a biologically active multi-chain polypeptide comprising at least two polypeptide chains, comprising the steps of introducing into a eukaryotic host cell a first eukaryotic vector comprising a first polynucleotide encoding a first polypeptide chain of a biologically active multi-chain polypeptide linked to a cell surface anchor, wherein said vector is operable in a eukaryotic host cell to direct expression and secretion of said first chain; and a second eukaryotic vector comprising a second polynucleotide encoding a second polypeptide chain of said multi-chain polypeptide, wherein said vector is operable in a eukaryotic host cell to direct expression and secretion of said second chain, wherein a eukaryotic host cell transformed with said first eukaryotic vector and said second eukaryotic vector exhibits, on expression of said first and second polynucleotides, the biological activity of said multi-chain polypeptide at the surface of the eukaryotic host cell; and culturing said host cell under conditions suitable for expression of said first and second polynucleotides.

In a further embodiment, the invention is directed to a method for displaying, on the surface of a eukaryotic host cell, a biologically active multi-chain polypeptide comprising at least two polypeptide chains, comprising the steps of introducing into a eukaryotic host cell a eukaryotic display vector, a eukaryotic display vector set, or a dual display vector as described above, and culturing said host cell under conditions suitable for expression of said polynucleotides.

The present invention further provides a eukaryotic host cell comprising a eukaryotic display vector, a eukaryotic display vector set, or a dual display vector as described herein. Suitable eukaryotic host cells can be animal cells, plant cells, or fungal cells. Preferably, the eukaryotic host cell will be a mammalian cell, an insect cell, and a yeast cell. Most preferably, the eukaryotic host cell will be a yeast cell, e.g., selected from the genus *Saccharomyces, Pichia, Hansenula, Schizosaccharomyces, Kluyveromyces, Yarrowia, Debaryomyces,* or *Candida*. Preferred yeast hosts include *Saccharomyces cerevisiae, Hansenula polymorpha, Kluyveromyces lactis, Pichia pastoris, Schizosaccharomyces pombe,* and *Yarrowia lipolytica*. The most preferred yeast host cell is *Saccharomyces cerevisiae*.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4A shows the expression of the 45 kD Aga2p-$V_H$-$C_H$1 fusion protein in yeast host cells EBY100 pTQ3-F2 and EBY100 pTQ3-PH1, and FIG. 4B shows the expression of the 30 kD $V_L$-$C_L$ chain in yeast host cells EBY100 pTQ3-F2 and EBY100 pTQ3-PH1. No fusion products were detected in either empty vector control. For each host cell, samples were prepared both before (−) and after (+) galactose induction of the GAL1 promoters operable in the yeast display vectors. FIG. 4C is a representation of immunofluorescence detection of assembled Fab antibodies on the yeast cell surface. (a) phase contrast (b) detection of HC (c) detection of LC.

FIG. 5A depicts yeast cells transformed with pTQ3-F2 (left panel) and pTQ3-PH1 (right panel) constructs were left untreated (dotted line) or induced for 48 hours at 20° C. (light grey line). Heavy chain (a), light chain display (b) and antigen binding (c) were analyzed using flow cytometry.

FIG. 8A shows a series of histograms of antigen binding and Fab display are shown for the unselected library (a) and polyclonal outputs of selection round 1, 2 and 3 (b, c, d). The diversified anti-streptavidin yeast repertoire was subjected to three rounds of FACS. The sorting gate used in each library selections is indicated. FIG. 8B shows polyclonal FACS analysis at different antigen concentrations of a FACS affinity selection campaign of a anti-streptavidin repertoire. A series of bivariant cytometric plots labeled for both antigen binding and Fab display show an increase in the population of yeast cells showing increased ratio of antigen binding to Fab display. FIG. 8C shows data obtained from yeast cells displaying the wild-type F2 (represented by "o") and mutants R2E10 (represented by triangles), R3B1 (represented by squares) and R3H3 (represented by diamonds) were labeled with anti-HA mAb and streptavidin-PE. The mean fluorescence for streptavidin binding was monitored over time. The dissociation rate constant is calculated from the slope of the line. FIG. 8D shows a series of cytometric plots of two selection campaigns using either Kingfisher in combination with FACS (Right column) or FACS alone (right column). The cytometric plots indicate the increasing percentage of antigen binding cells through unselected (a) round 1 (b) and round 2 (c) of selection.

DETAILED DESCRIPTION OF THE INVENTION

Figure 1:
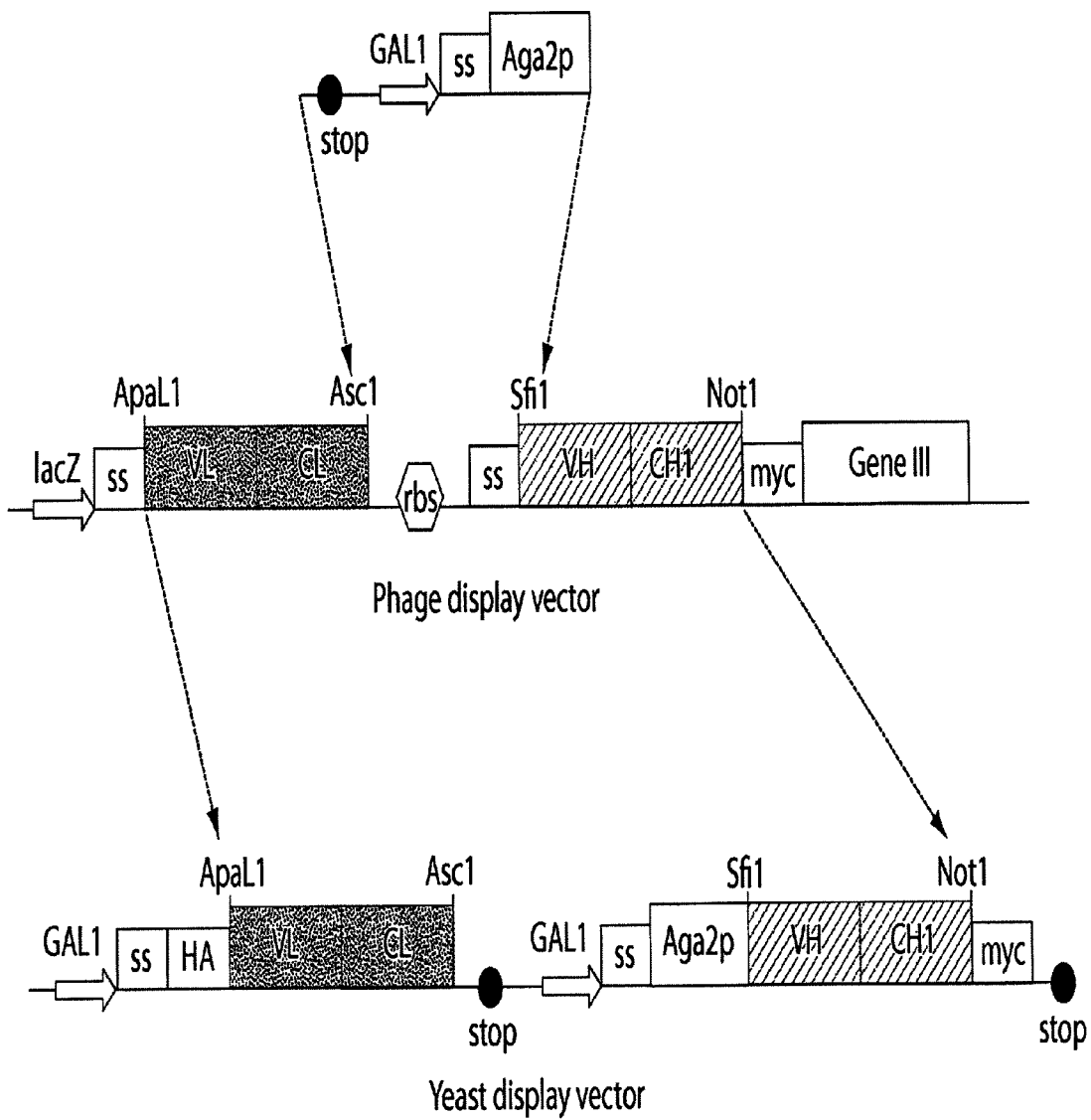
FIG. 1 is a schematic diagram that illustrates the phage display-eukaryotic display transfer system. The genetic information encoding the chains of a Fab polypeptide are transferred from a phage display vector to a multi-chain eukaryotic vector of the present invention as a single, excised nucleic acid. Unwanted intervening genetic elements (if any) are then replaced.

A description of preferred embodiments of the invention follows.

The invention disclosed in the present application describes the first demonstration of the successful expression, transport, assembly, and immobilization (or "display") of a functional heterologous multi-chain polypeptide (e.g., Fab antibody fragments) on the surface of a eukaryotic host cell (e.g., yeast). The present invention makes possible the construction of vector libraries and eukaryotic host cell libraries, wherein the cells display a highly variable repertoire of multi-chain polypeptides, which multi-chain polypeptides exhibit a high degree of sequence diversity within the repertoire and a consequently highly variable range of biological activities such as target (e.g., antigen) specificity. One skilled in the art will appreciate that, by following the teaching of the present invention, a vast array of multi-chain molecules can be stably expressed on the surface of eukaryotic host cells such as yeast.

DEFINITIONS

Unless otherwise defined herein, the language and terminology used in the description of the present invention is used in accordance with the plain meaning of such language and terminology as generally understood and accepted by those of ordinary skill in the art. In an attempt to avoid any latent confusion or ambiguity, particular elements or features as they relate to the present invention are set forth below.

As used herein, a "multi-chain polypeptide" refers to a functional polypeptide comprised of two or more discrete polypeptide elements (i.e., "chains"), covalently or non-covalently linked together by molecular association other than by peptide bonding. The chains of a multi-chain polypeptide can be the same or different. A prominent example of a multi-chain polypeptide is an immunoglobulin (e.g., IgA, IgD, IgE, IgG, and IgM), typically composed of four chains, two heavy chains and two light chains, which assemble into a multi-chain polypeptide in which the chains are linked via several disulfide (covalent) bonds. Active immunoglobulin Fab fragments, involving a combination of a light chain (LC) domain and a heavy chain (HC) domain, form a particularly important class of multi-chain polypeptides. As well as forming a disulfide bond, the LC and HC of a Fab are also known to effectively associate (non-covalently) in the absence of any disulfide bridge. Other examples of multi-chain polypeptides include, but are not limited to, the extracellular domains of T cell receptor (TCR) molecules (involving α and β chains, or γ and δ chains), MHC class I molecules (involving α1, α2, and α3 domains, non-covalently associated to β2 microglobulin), and MHC class II molecules (involving α and β chains). Expression of TCR and MHC binding domains in a eukaryotic host cell where at least one chain is anchored at the host cell surface with a non-naturally occurring (heterologous) anchor is specifically contemplated herein.

The term "biologically active" when referring, e.g., to a multi-chain polypeptide, means that the polypeptide exhibits a functionality or property that is useful as relating to some biological process, pathway or reaction. Biological activity can refer to, for example, an ability to interact or associate with (e.g., bind to) another polypeptide or molecule, or it can refer to an ability to catalyze or regulate the interaction of other proteins or molecules (e.g., enzymatic reactions). Biological activity can also refer to the ability to achieve a physical conformation characteristic of a naturally occurring structure, such as the four-chain conformation of naturally occurring immunoglobulin gamma (IgG) molecules, the α and β chains of a T cell receptor molecule, or the conformation of an antigen presenting structure of a major histocompatability complex (e.g., MHC peptide groove).

As used herein, "vector" refers to any element capable of serving as a vehicle of genetic transfer, gene expression, or replication or integration of a foreign polynucleotide in a host cell. A vector can be an artificial chromosome or plasmid, and can be integrated into the host cell genome or exist as an independent genetic element (e.g., episome, plasmid). A vector can exist as a single polynucleotide or as two or more separate polynucleotides. A "multi-chain display vector" of the present invention is capable, in an appropriate host, of directing expression of at least one chain of a multi-chain polypeptide and processing it for display on the surface of said host. Vectors according to the present invention can be single copy vectors or multicopy vectors (indicating the number of copies of the vector typically maintained in the host cell). Preferred vectors of the present invention include yeast expression vectors, particularly 2µ vectors and centromere vectors. A "shuttle vector" (or bi-functional vector) is known in the art as any vector that can replicate in more than one species of organism. For example, a shuttle vector that can replicate in both *Escherichia coli* (*E. coli*) and *Saccharomyces cerevisiae* (*S. cerevisiae*) can be constructed by linking sequences from an *E. coli* plasmid with sequences from the yeast 2µ plasmid. A particularly preferred embodiment of the present invention is a "dual display vector", which is a shuttle vector that is capable not only of replicating in two different species but is capable of expressing and displaying heterologous polypeptides in two or more host species.

As used herein, "secretion" refers to peptides having a secretion signal and are processed in the endoplasmic reticulum. If secreted peptides either contain anchor sequences or associate with the outside of the cell surface, the peptides are said to be "displayed". As used herein, "display" and "surface display" (used interchangeably herein) refer to the phenomenon wherein a heterologous polypeptide is attached, or "anchored", to the outer surface of a phage or host cell, whereby the anchored polypeptide is exposed to the extracellular environment. The present invention is particularly directed to the display of a multi-chain polypeptide on the surface of a eukaryotic host cell, by expression of each of the chains in the host cell and the anchoring of at least one chain of the multi-chain polypeptide to the surface of the host cell. A "display vector" refers to a vector that is capable of expressing a polypeptide in a host cell or phage such that the expressed polypeptide is displayed on the surface of said host cell or phage. Display vectors of the present invention direct expression of multi-chain polypeptides in a host cell or phage such that the biological activity of the displayed polypeptide is exhibited at the surface of the host cell or phage. Dual display vectors of this invention direct expression of multi-chain polypeptides in at least two different hosts (preferably, e.g., a prokaryotic host cell and a eukaryotic host cell) such that the biological activity of the polypeptide is exhibited at the surface of the respective hosts.

The term "repertoire" refers to a population of diverse molecules, e.g., nucleic acid molecules differing in nucleotide sequence, or polypeptides differing in amino aid sequence. According to the present invention, a repertoire of polypeptides is preferably designed to possess a diverse population of molecules that differ in their binding sites for a target molecule. The polypeptides of the repertoire are designed to have common structural elements, e.g., as with a repertoire of Fabs, having a well-recognized two-chain structure (Ig light chain associated with $V_H$ and $C_H1$ domains of an Ig heavy chain) but exhibiting different binding specificities, due to variation in the respective variable regions of the component chains.

The term "library" refers to a mixture of heterogeneous polypeptides or polynucleotides. A library is composed of members that have similar polypeptide or polynucleotide sequences. Where the library is a polynucleotide library, it encodes a repertoire of polypeptides (especially, e.g., with regard to the present invention, a repertoire of multi-chain polypeptides). Sequence differences between library members are responsible for the diversity present in the library. The library can take the form of a simple mixture of polypeptides or polynucleotides, or can be in the form organisms or cells, for example bacteria, viruses, animal or plant cells and the like, that are transformed with a library of polynucleotides. Where the heterogeneous polypeptides are expressed and exhibited at the surface of the cells or organisms forming the library, the library is a "display library". Advantageously, polynucleotides are incorporated into expression vectors, in order to allow expression of the polypeptides encoded by the polynucleotides. In a preferred aspect, therefore, a library can take the form of a population of host organisms, each organism containing one or more copies of an expression vector containing a single member of the library in polynucleotide from that can be expressed to produce its corresponding polypeptide member. Thus, the population of host organisms has the potential to encode a large repertoire of genetically diverse polypeptide variants.

The present invention is directed to novel multi-chain display vectors. In one embodiment of the present invention, the polynucleotides that encode the chains of the multi-chain polypeptide are present on separate (i.e., two or more) expression vectors, the compilation of which form a functional display "vector set" (the general term, "vector" encompasses vector sets). For example, if the multi-chain polypeptide were a two-chain polypeptide comprised of the light chain and the heavy chain of a biologically active Fab, the polynucleotide encoding the LC can be incorporated into one expression vector, and the polynucleotide encoding the HC can be incorporated into a second, separate, expression vector (most preferably expressed as a HC-anchor fusion protein). Individually, each vector is capable of expressing its respective polypeptide chain; the two vectors together form a matched vector set, which set encodes the chains of a biologically active multi-chain polypeptide. Similarly, separate host cells, each transformed with the different vectors of a vector set, collectively form a matched host cell set (or specifically in the case of a two-vector set, a matched "cell pair"). The vectors and vector sets will preferably also include one or more selectable markers (e.g., TRP, ampR, and the like) to facilitate selection and propagation of successfully transformed hosts.

A "host cell" refers to any cell (prokaryote or eukaryote) transformed to contain a vector. According to the present invention, preferred host cells are bacterial cells and eukaryotic cells, including, but not limited to, protist cells, fungus cells, plant cells, and animal cells. Host cells of the invention can be of any genetic construct, but are preferably haploid, diploid cells, or multiploid (e.g., as is typical of immortalized cell lines in culture). Preferred host cells include insect cells (e.g., Sf9), mammalian cells (e.g., CHO cells, COS cells, SP2/0 and NS/0 myeloma cells, human embryonic kidney (HEK 293) cells, baby hamster kidney (BHK) cell, human B cells, human cell line PER.C6™ (Crucell)), seed plant cells, and Ascomycete cells (e.g., *Neurospora* and yeast cells; particularly yeast of the genera *Saccharomyces, Pichia, Hansenula, Schizosaccharomyces, Kluyveromyces, Yarrowia*, and *Candida*). Preferred exemplar yeast species include *S. cerevisiae, Hansenula polymorpha, Kluyveromyces lactis, Pichia pastoris, Schizosaccharomyces pombe*, and *Yarrowia lipolytica*. A particularly preferred yeast host cell is *S. cerevisiae*.

The term "phage" refers to a "bacteriophage", which is a bacterial virus containing a nucleic acid core and a protective proteinaceous shell. The terms "bacteriophage" and "phage" are used herein interchangeably. Unless otherwise noted, the terms "bacteriophage" and "phage" also encompass "phagemids" (i.e., bacteriophage the genome of which includes a plasmid that can be packaged by coinfection of a host with a helper phage). In preferred embodiments of the present invention, the phage is an M13 phage.

The terms "anchor", "cell surface anchor" and "anchor polypeptide", refer to a polypeptide moiety that, on expression in a host cell, becomes attached or otherwise associated with the outer surface of the host cell or, in the case of a phage display system, on the surface of a phage particle (e.g., as part of the capsid or as part of a filament). An anchor polypeptide can be a coat protein moiety, a transmembrane protein moiety, or can be a polypeptide moiety otherwise linked to the cell surface (e.g., via post-translational modification, such as by a phosphatidyl-inositol or disulfide bridge). The term encompasses native proteins to the host cell or phage, or exogenous proteins introduced for the purpose of anchoring to a host cell wall or phage coat. Anchors include any synthetic modification or truncation of a naturally occurring anchor that still retains the ability to be attached to the surface of a host cell or phage particle. Preferred anchor protein moieties are contained in, for example, cell surface proteins of a eukaryotic cell. Effective anchors include portions of a cell surface protein sufficient to provide a surface anchor when fused to another polypeptide, such as a chain of a multi-chain polypeptide in accordance with this invention. The use of protein pairs that are separately encoded and expressed but associate at the surface of a cell by covalent (e.g., disulfide) or non-covalent bonds is also contemplated as a suitable anchor, and in this regard particular mention is made of the yeast α-agglutinin components, Aga1p and Aga2p, which form a glycan-immobilized, disulfide-linked complex on the surface of yeast cells. Another protein pair that can be employed as an anchor are proteins that form "leucine zipper" interactions and the like, such as the nuclear proteins Jun and Fos (which form a "jun/fos linkage"). For example, a display vector can be designed according to this invention to direct the expression in a host cell of a first chain of a multi-chain polypeptide fused to the leucine zipper moiety of Jun, and a second vector can be designed to direct independent expression of the leucine zipper moiety of Fos fused to a surface protein of the host. On expression of the vector structural genes, the first chain polypeptide will be associated (i.e., anchored) with the host cell surface via a jun/fos linkage, as the Jun and Fos leucine zipper forms a linkage between the first chain polypeptide and the host cell surface protein fused to the Fos part of the zipper. Any suitable protein binding pair of this sort can be used. Preferred examples of polypeptide anchors include the pIII coat protein of filamentous phage or fragments thereof (e.g., pIII anchor domain or "stump", see U.S. Pat. No. 5,658,727) for phage display systems, and for yeast display systems FLO1 (a protein associated with the flocculation phenotype in *S. cerevisiae*), α-agglutinin, and a-agglutinin (e.g., Aga1p and Aga2p subunits), and functional fragments thereof.

As used herein, the term "fusion protein" denotes a hybrid polypeptide comprised of amino acid sequences from more than one source, linked together to form a non-naturally occurring, unitary polypeptide. Fusion proteins are prepared, for example, by operably linking coding sequences for the component amino acid sequences in frame, such that, upon expression, they are produced as a single polypeptide. Alternatively, fusion proteins can be assembled synthetically, e.g., by creating a peptide bond between two or more separate polypeptides.

As used herein "linked" refers to a functional and structural connection between two or more elements. As used herein, the linked elements typically refer to an operable connection between two or more polynucleotide elements or polypeptide elements. For example, as discussed above, a polypeptide can be linked to an anchor protein (via a peptide bond or via peptide linker), thus forming a fusion protein. Similarly, the polynucleotides encoding the polypeptide and anchor protein can be linked such that the fusion protein is transcribed and translated as a unitary RNA message. Polypeptides can also be indirectly linked to an anchor via an intermediate association, one example of which is the use of the high-affinity interaction of the Jun and Fos leucine zippers (i.e., a "jun/fos linkage") to effectively link a polypeptide to the surface of a phage or host cell (Crameri, R. and Glaser, K., 1996). Any suitable heterodimeric or homodimeric pair of molecules can be used (Chang, H. et al., 1994; Moll, J. et al., 2001; Pu, W. and Struhl, K., 1993).

It is understood by persons of ordinary skill in the art that polynucleotides, which encode one or more chains of a multi-chain polypeptide to be expressed and displayed in a phage display or host cell display system, can be operably linked to a promoter (to facilitate transcription), or operably linked to a signal sequence or leader peptide (to facilitate cellular processing and transport to the surface). Such genetic control elements and functional linkages thereto are numerous and well known in the art, and the present invention is not limited by the use thereof. Preferred promoters, however, include inducible promoters. Particularly preferred promoters (for eukaryotic systems) include those useful in yeast vectors, such as pGAL1, pGAL1-10, pGal104, pGal10, pPGK, pCYC1, and pADH1. Other preferred promoters include the LacZ promoter (for non-eukaryotic systems). Particularly preferred signal sequences include the Aga2p signal sequence (for eukaryotic systems), and the pill signal sequence (for non-eukaryotic systems).

Another useful tool known to practitioners in the art, are molecular labels or "tags" (e.g., epitope tags, reporter genes, radioisotope, fluorescent or chemiluminescent moieties, etc.), which facilitate the practitioner's ability, for example, to detect the presence of a polypeptide linked thereto. Epitope tags (e.g., peptide segments known to be recognized by particular antibodies or binding moieties) are particularly useful herein, in that they can be co-expressed as a fusion partner with one or more chains of a multi-chain polypeptide in a vector or vectors according to the invention, to permit the detection of expression of one or more chains with which the tag is co-expressed. As known and used in the art, tags are typically placed under the same genetic controls as a gene of interest (preferably as a component of an expressed fusion protein). If and when the gene product of interest is not easily detectable, the tag provides an easily detectable, and often quantifiable, signal indicating the presence of the gene product of interest. By linking a tag to a polypeptide gene product of interest, the practitioner can monitor such processes as, for example, gene expression, polypeptide trafficking, extracellular display, and protein-protein interactions (Fields, S, and Sternglanz, R., 1994; Phizicky, E. and Fields, S., 1995).

Accordingly, the chains of a multi-chain polypeptide can be optionally linked to one or more tags, either individually or jointly. A variety of tags are known in the art and are commercially available (Amersham Pharmacia Biotech, Piscataway, N.J.; Applied Biosystems, Foster City, Calif.; Promega, Madison, Wis.; Roche Molecular Biochemicals, Indianapolis, Ind.; Stratagene, La Jolla, Calif.). Preferably, the linkage is achieved via a peptide bond (thus creating a fusion protein), wherein the polynucleotide encoding a chain of a multi-chain polypeptide is linked to a tag (e.g., an epitope tag). Preferred tags include polyHis tags, HA tags, and myc tags.

As used herein, the term "recombinant" is used to describe non-naturally altered or manipulated nucleic acids, host cells transfected with exogenous nucleic acids, or polypeptides expressed non-naturally, through manipulation of isolated DNA and transformation of host cells. "Recombinant" is a term that specifically encompasses DNA molecules that have been constructed in vitro using genetic engineering techniques, and use of the term "recombinant" as an adjective to describe a molecule, construct, vector, cell, polypeptide or polynucleotide specifically excludes naturally occurring molecules.

Similarly the term "transform" refers generally to any artificial (i.e., practitioner-controlled) method of introducing genetic material into a cell or phage without limitation to the method of insertion. Numerous methods are known in the art and described by the references cited and incorporated herein. Specifically as applied to the present invention, the term "transformant" refers to a host cell that has been transformed and encompasses, for example, diploid cells, which are the product of the controlled fusion of matched haploid cell pairs (as with the controlled mating of haploid yeast spores of opposite mating type).

Methods for "transferring" nucleic acid sequence information from one vector to another is not limiting in the present invention and includes any of a variety of genetic engineering or recombinant DNA techniques known in the art. Once again, a vast array of methods are known in the art and described in the references cited and incorporated herein. Particularly preferred transfer techniques include, but are not limited to, restriction digestion and ligation techniques (utilizing unique cloning sites), PCR amplification protocols (utilizing specific primer sequences), and homologous recombination techniques (utilizing polynucleotide regions of homology).

Employing genetic engineering technology necessarily requires growing recombinant host cells (transformants) under a variety of specified conditions as determined by the requirements of the organism and the particular cellular state desired by the practitioner. For example, the organism can possess (as determined by its genetic disposition) certain nutritional requirements, or particular resistance or sensitivity to physical (e.g., temperature) and/or chemical (e.g., antibiotic) conditions. In addition, specific culture conditions can be necessary to induce or repress the expression of a desired gene (e.g., the use of inducible promoters), or to initiate a particular cell state (e.g., yeast cell mating or sporulation). These varied conditions and the requirements to satisfy such conditions are understood and appreciated by practitioners in the art.

Accordingly, practice of various aspects of the present invention requires that host cells be cultured under "conditions suitable" or "conditions sufficient" to achieve or to induce particular cellular states. Such desirable cellular states include, but are not limited to: cellular growth and reproduction; the expression, secretion or transport, and association of the chains of a multi-chain polypeptide such that the biological activity of the multi-chain polypeptide is exhibited at the surface of the host cell (or phage particle); the fusion of haploid cells to form a diploid cell (e.g., fertilization, zygote formation, the mating of cells of opposite mating types); and meiosis of a diploid cell to form haploid daughter cells (e.g., gametogenesis, sporulation). The present invention is not limited by the physical and chemical parameters of such "suitable conditions", but such conditions are determined by the organisms and vectors used to practice the invention, and by practitioner preference.

Multi-Chain Polypeptide Eukaryotic Display Vectors

As outlined earlier, the present invention is directed to a novel genetic vector, useful in a eukaryotic cell to display a multi-chain polypeptide on the surface of the cell such that the biological activity of the multi-chain polypeptide is exhibited at the surface of the cell. According to the invention, the multi-chain polypeptide can be encoded in a single vector, or individual chains of the multi-chain polypeptide can be encoded in a vector set. For example, in one aspect of the invention, the vector can exist as a vector set, wherein each chain of a multi-chain polypeptide is encoded on one of a matched pair of vectors such that when the vector set is present in a single eukaryotic cell, the chains of the multi-chain polypeptide associate at the surface of the eukaryotic cell. In another aspect of the invention, the display vector can be a dual display vector, wherein the vector is capable of (i) expressing in a eukaryotic cell and displaying on the surface of a eukaryotic cell a biologically active multi-chain polypeptide, and (ii) expressing in a prokaryotic cell and displaying on the surface of a bacteriophage the biologically active multi-chain polypeptide.

The multi-chain polypeptide can be any polypeptide comprised of two or more discrete polypeptide elements, referred to as chains of the multi-chain polypeptide, which chains are covalently or non-covalently linked (other than by peptide bonding) to form a biologically active polypeptide. Preferably, the multi-chain polypeptide encoded by the multi-chain display vector(s) of the present invention exists as either a two-, three-, or four-chain polypeptide. The chains of the polypeptide can be the same (e.g., a homo-dimer, -trimer, or -tetramer) or different (e.g., a hetero-dimer, -trimer, or -tetramer). Preferably, the multi-chain polypeptide is a two-chain or four-chain polypeptide comprised of two different chains. More preferably, the multi-chain polypeptide is selected from a group of multi-chain polypeptides consisting of T cell receptors, MHC class I molecules, MHC class II molecules, immunoglobulins and biologically active immunoglobulin fragments (e.g., Fabs). More preferably, the multi-chain polypeptide is an IgA, IgD, IgE, IgG, IgM, or biologically active fragment thereof. Most preferably, the multi-chain polypeptide is a Fab fragment of an Ig, wherein the first polynucleotide of the multi-chain display vector comprises a segment that encodes the $V_H$ and $C_H1$ domains of an Ig heavy chain, and a second polynucleotide comprises a segment that encodes an Ig light chain (i.e., $V_L$ and $C_L$ domains).

The chains of the multi-chain polypeptide (e.g., first chain, second chain, third chain, etc.) are encoded as polynucleotides (e.g., first polynucleotide, second polynucleotide, third polynucleotide, etc., respectively) in an expression vector. It will be appreciated and understood by persons skilled in the art that the polynucleotide sequences encoding the chains do not necessarily have to be inserted into the identical plasmid, or under the same gene expression control, in order to produce a functional multi-chain polypeptide. For example, the polynucleotide encoding the light chain and heavy chain of an Ig Fab can be located on separate plasmids and transformed as such into an identical host cell for co-expression and co-processing into a functional multi-chain polypeptide.

It will also be appreciated by those skilled in the art, that the sequences of the polynucleotides that encode the chains of a multi-chain polypeptide need not originate from an identical, or same source. For instance, an Ig molecule can be produced having variable domains ($V_H$ and $V_L$) the same as those from a monoclonal antibody having a desired specificity, and constant domains ($C_H1$ and $C_L$) from a different monoclonal antibody having desired properties (e.g., to provide human compatibility or to provide a particular complement binding site).

Moreover, the heterologous polynucleotide encoding the chains of a multi-chain polypeptide (e.g., Ig domains) can be variegated, to produce a family of polynucleotide homologs, encoding polypeptide chains that vary slightly in amino acid sequence from one another while having the same overall structure. In this way, when the homologs are incorporated into different host cells and expressed, a library of multi-chain polypeptides of varied sequence are displayed, providing a peptide display library suitable for screening, e.g., to discover homologous multi-chain polypeptides having altered biological activity. Such alterations in amino acid sequence can be achieved by suitable mutation or partial synthesis and replacement or partial or complete substitution of appropriate regions of the corresponding polynucleotide coding sequences. Substitute constant domain portions can be obtained from compatible recombinant DNA sequences.

Given proper selection of expression vector components and compatible host cells, the chains of the multi-chain polypeptide will be displayed on the surface of a eukaryotic host cell. Persons skilled in the art will appreciate that this can be achieved using any of a number of variable expression vector constructs, and that the present invention is not limited thereby. The display vector itself can be constructed or modified from any of a number of genetic vectors and genetic control elements known in the art and commercially available (e.g., from InVitrogen (Carlsbad, Calif.); Stratagene (La Jolla, Calif.); American Type Culture Collection (Manassas, Va.)). Essentially, the vector construct of the present invention expresses the polypeptide chains for effective display of a fully assembled, multi-chain polypeptide on the surface of a eukaryotic cell transformed with the vector such that the biological activity of the multi-chain polypeptide is exhibited at the surface of the host cell.

To achieve effective cellular expression of the multi-chain polypeptide, the polynucleotides encoding each of the chains of the multi-chain polypeptide are, preferably, linked to a transcriptional promoter to regulate expression of the polypeptide chains. The effective promoter must be functional in a eukaryotic system, and optionally (particularly in the case of a dual display vector) effective as a prokaryotic promoter as well. In a particular dual display vector, the eukaryotic promoter(s) and the prokaryotic promoter(s) selected for regulating expression of the heterologous polypeptide chains of a multi-chain polypeptide can be the same or different promoters, as long as they are appropriately functional in the intended host organisms. Alternatively, they can be independently selected for the expression of each chain in a particular host. The eukaryotic promoter can be a constitutive promoter but is preferably an inducible promoter. In order to achieve balanced expression and to ensure simultaneous induction of expression, a vector construct that utilizes the same promoter for each chain is preferred.

A number of eukaryotic promoters useful in the present invention are known in the art. Particularly preferred promoters (for eukaryotic systems) include those useful in yeast expression vectors, such as galactose inducible promoters, pGAL1, pGAL1-10, pGal4, and pGal10; phosphoglycerate kinase promoter, pPGK; cytochrome c promoter, pCYC1; and alcohol dehydrogenase I promoter, pADH1.

Preferably, each of the polynucleotides encoding a chain of a multi-chain polypeptide is also linked to a signal sequence (or a leader peptide sequence). The signal sequence operates to direct transport (sometimes referred to as secretion) of a nascent polypeptide into or across a cellular membrane. Chains of a multi-chain polypeptide expressed in a eukaryotic cell from a vector of the present invention are transported to the endoplasmic reticulum (ER) for assembly and transport to the cell surface for extracellular display. An effective signal sequence should be functional in a eukaryotic system, and optionally (particularly in the case of a dual display vector) the signal sequence should be effective in a prokaryotic system as well. Polynucleotides encoding the chains of a multi-chain polypeptide are typically directly linked, in frame (either immediately adjacent to the polynucleotide or optionally linked via a linker or spacer sequence), to a signal sequence, thus generating a polypeptide chain-signal sequence peptide fusion protein. Preferably, each chain of a multi-chain polypeptide is fused to a separate signal peptide.

The signal sequence encoding the signal peptide can be the same or different for each chain of the multi-chain polypeptide. The signal sequence can be native to the host or heterologous, as long as it is operable to effect extracellular transport of the polypeptide to which it is fused. Several signal sequences operable in the present invention are known to persons skilled in the art (e.g., Mfα1 prepro, Mfα1 pre, acid phosphatase Pho5, Invertase SUC2 signal sequences operable in yeast; pIII, PelB, OmpA, PhoA signal sequences operable in E. coli; gp64 leader operable in insect cells; IgK leader, honeybee melittin secretion signal sequences operable in mammalian cells). The signal sequences are preferably derived from native secretory proteins of the host cell. Particularly preferred eukaryotic signal sequences include those of α-mating factor of yeast, α-agglutinin of yeast, invertase of Saccharomyces, inulinase of Kluyveromyces, and most preferably the signal peptide of the Aga2p subunit of a-agglutinin (especially in embodiments where the anchoring polypeptide to be used is the Aga2p polypeptide).

In the particularly preferred embodiment, wherein the multi-chain polypeptide is a Fab, the first polynucleotide comprises an Aga2p signal sequence in frame with a segment that encodes the $V_H$ and $C_H1$ regions of an Ig heavy chain, and the second polynucleotide comprises an Aga2p signal sequence in frame with a segment that encodes an Ig light chain.

The multi-chain eukaryotic display vector of the present invention operates in a eukaryotic host cell such that the multi-chain polypeptide encoded by the vector is displayed on the surface of the host cell. Anchorage ("tethering" or "display") on the surface of the host cell is achieved by linking at least one chain of the multi-chain polypeptide to a molecular moiety attached to the host cell wall. More than one chain of a multi-chain polypeptide can be linked to an anchor, but because the fully assembled multi-chain polypeptide requires (and preferably contains) only one point of attachment to the host cell surface, only one chain of the multi-chain polypeptide need be the point of cellular attachment. Display on the surface of the cell can be achieved by linking at least one of the polypeptide chains to an anchor protein or functional fragment (moiety) thereof. The effective anchor should be functional in a eukaryotic system, and optionally (particularly in the case of a dual display vector) the anchor should be effective as an anchor on the surface of a bacteriophage as well. Preferably, the anchor is a surface-expressed protein native to the host cell, e.g., either a transmembrane protein or a protein linked to the cell surface via a glycan bridge. Several anchor proteins operable in the present invention are known to persons skilled in the art (e.g., pIII, pVI, pVIII, LamB, PhoE, Lpp-OmpA, Flagellin (FliC), or at least the transmembrane portions thereof, operable in prokaryotes/phage; platelet-derived growth factor receptor (PDGFR) transmembrane domain, glycosylphosphatidylinositol (GPI) anchors, operable in mammalian cells; gp64 anchor in insect cells, and the like). Preferably, where yeast is the host, the anchor protein is α-agglutinin, a-agglutinin (having subcomponents Aga1p and Aga2p), or FLO1, which naturally form a linkage to the yeast cell surface.

Linkage of a polypeptide chain to an anchor can be achieved, directly or indirectly, by a variety of molecular biology techniques. The present invention is not limited by the method of chain-anchor linkage, only by the functional requirement that the linked polypeptide chain is immobilized on the surface of the host cell (or optionally bacteriophage) as a result of such linkage.

A preferred method of chain-anchor linkage is through the construction of a chain-anchor fusion protein. Similar to, and preferably in concert with, a chain-signal peptide fusion protein, a polynucleotide encoding a chain of a multi-chain polypeptide is directly linked, in frame (either immediately adjacent to the polynucleotide or optionally linked via a linker or spacer sequence), to an anchor, thus generating a signal peptide-polypeptide chain-anchor fusion protein.

Alternative modes of peptide-peptide linkage are know in the art and available to achieve the effective chain-anchor linkage of the present invention. For example, and as previously cited, a chain of the multi-chain polypeptide can be indirectly linked to an anchor via an intermediate association such as the high affinity interaction of the Jun and Fos leucine zippers (jun/fos linkage) to covalently link a polypeptide chain to an anchor of a phage or host cell (Crameri, R. and Suter, M., 1993; Crameri, R. and Blaser, K., 1996).

In the particularly preferred embodiment, wherein the multi-chain polypeptide is an Ig Fab fragment: the first polynucleotide comprises an Aga2p signal sequence in frame with a segment that encodes an Aga2p anchor, and in frame with a segment that encodes the $V_H$ and $C_H1$ domains of an Ig heavy chain; and the second polynucleotide comprises an Aga2p signal sequence in frame with a segment that encodes an Ig light chain.

Preferably, the multi-chain display vectors of the present invention provide cloning sites to facilitate transfer of the polynucleotide sequences that encode the chains of a multi-chain polypeptide. Such vector cloning sites comprise at least one restriction endonuclease recognition site positioned to facilitate excision and insertion, in reading frame, of polynucleotides segments. Any of the restriction sites known in the art can be utilized in the vector construct of the present invention. Most commercially available vectors already contain multiple cloning site (MCS) or polylinker regions. In addition, genetic engineering techniques useful to incorporate new and unique restriction sites into a vector are known and routinely practiced by persons of ordinary skill in the art. A cloning site can involve as few as one restriction endonuclease recognition site to allow for the insertion or excision of a single polynucleotide fragment. More typically, two or more restriction sites are employed to provide greater control of, for example, insertion (e.g., direction of insert), and greater flexibility of operation (e.g., the directed transfer of more than one polynucleotide fragment). Multiple restriction sites can be the same or different recognition sites.

The multi-chain eukaryotic display vector of the present invention preferably contains restriction sites positioned at the ends of the coding sequences for the chains of the multi-chain polypeptide. Restriction sites can be positioned at the extreme ends, 5' and 3' of the polynucleotide segment including all of the coding sequences for the chains of a multi-chain polypeptide (on a single vector); or, more preferably, restriction sites can be positioned at the 5' and 3' ends of each polynucleotide segment encoding a chain of the multi-chain polypeptide. Most preferably each of the restriction sites is unique in the vector and different from the other restriction sites. This particularly useful vector construct provides flexibility and control for the modular transfer of individual polynucleotide sequences encoding a chain of a multi-chain polypeptide.

In a particularly preferred vector construct, wherein the multi-chain polypeptide is a Fab, the first polynucleotide comprises an Aga2p signal sequence in frame with a segment that encodes an Aga2p anchor, and in frame with a segment that encodes the $V_H$ and $C_H1$ regions of an Ig heavy chain, wherein the Ig heavy chain region is bordered by unique restriction sites (e.g., SfiI and NotI); and the second polynucleotide comprises an Aga2p signal sequence in frame with a segment that encodes an Ig light chain, wherein the Ig light chain region is bordered by unique restriction sites (e.g., ApaLI, and AscI).

In a preferred embodiment of the multi-chain eukaryotic display vector, one or more of the chains of the multi-chain polypeptide expressed by the vector in a host cell is linked to a molecular tag or reporter gene. Preferably, the linkage is a peptide bond that links a polypeptide tag to a chain of the multi-chain polypeptide. One or more chains of the multi-chain polypeptide can be tagged using identical, similar or different tags. Preferred tags include epitope tags (Munro, S, and Pelham, H., 1987). Preferred epitope tags include poly-His tags, HA tags, and myc tags, and preferably each chain is fused to a different tag.

Building upon the particularly preferred vector construct exemplified herein, wherein the multi-chain polypeptide is a Fab fragment of an immunoglobulin, the first polynucleotide comprises an Aga2p signal sequence in frame with a segment that encodes an Aga2p anchor, in frame with a segment that encodes the $V_H$ and $C_H1$ regions of an Ig heavy chain, and in frame with a segment that encodes a myc tag, wherein the Ig heavy chain region is bordered by unique restriction sites (e.g., SfiI and NotI); and the second polynucleotide comprises an Aga2p signal sequence in frame with a segment that encodes a HA tag, and in frame with a segment that encodes an Ig light chain, wherein the Ig light chain region is bordered by unique restriction sites (e.g., ApaLI, and AscI).

Eukaryotic Cell Display of a Multi-Chain Polypeptide

Utilizing the vector described and taught herein, a process for displaying a biologically active multi-chain polypeptide on the surface of a eukaryotic host cell is demonstrated herein for the first time. The process for displaying a multi-chain polypeptide on the surface of a eukaryotic host cell comprises introducing the vector (possibly as a vector set) into a eukaryotic cell (i.e., a host cell), and culturing the host cell under conditions suitable for expression, transport, and association of the chains of the multi-chain polypeptide with the host cell surface such that the biological activity of the multi-chain polypeptide is exhibited at the surface of the host cell.

The mode of introduction of the vector of the present invention into a host cell is not limiting to the present invention and includes any method for introducing genetic material into a cell known in the art. Such methods include but are not limited to methods known and referred to in the art as transfection, transformation, electroporation, liposome mediated transfer, biolistic transfer, conjugation, cellular fusion, and nuclear microinjection. Transformation techniques known in the art are the preferred methods of genetic transfer.

Multi-Chain Polypeptide Display Host Cells (and Host Cell Pairs)

Vectors of the present invention are operable in a eukaryotic host cell to effect expression and to display a multi-chain polypeptide on the surface of the eukaryotic host cell. Optionally, particularly in the case of dual display vectors, the vectors of the present invention are operable in a prokaryotic host cell as well, to effect expression in a bacterial host cell and to display a multi-chain polypeptide on the surface of a bacteriophage. The eukaryotic host cell can be any eukaryotic cell, of any genotype, differentiated or undifferentiated, unicellular or multi-cellular, depending on the practitioner's particular interest and requirements. Particularly useful eukaryotic cells include mammalian cells, plant cells, fungus cells, and protist cells. Preferably, the host cell is an undifferentiated, unicellular, haploid or diploid cellular organism. Fungi are preferred host cells, particularly species of the phylum *Ascomycota* (sac fungi), because of their ease and diversity of culture conditions, the variety of biochemical and cellular mutants available, their short generation time, and their life cycle (see below). Preferred fungal host cells include those of the genera *Neurospora* and the various yeasts, such as *Saccharomyces, Pichia, Hansenula, Schizosaccharomyces, Kluyveromyces, Yarrowia, Debaryomyces,* and *Candida*. Most preferred species is *Saccharomyces cerevisiae* (baker's yeast), perhaps the most well known, characterized, and utilized eukaryotic cell system in molecular biology research.

In particular embodiments, the eukaryotic host cells are suitable for cell fusion (see below). For example, yeast cells of opposite mating type can be "mated" to produce fused diploid cells. In addition, yeast protoplasts or spheroplasts suitable for cell fusion are also suitable eukaryotic host cells for the purposes of the invention. Alternatively, cells grown in culture (e.g., mammalian cells, insect cells, etc.), can be fused by methods known in the art (e.g., using Sendai virus or electric current).

Phage Display-Eukaryotic Display Transfer System

The technical advancement of the present invention to display complex multi-chain polypeptides on the surface of a eukaryotic host cell can be coupled with the power of phage display technology. For example, by employing a phage display-eukaryotic display transfer system as described herein, practitioners can, for the first time, combine the immense diversity provided by phage display libraries and phage display technology with the cellular expression, processing, assembly, and display provided by the aforementioned multi-chain eukaryotic display technology. The transfer of nucleic acid sequence information between a phage display vector and the eukaryotic vector of the present invention can be achieved by a variety of genetic transfer methods known in the art (e.g., genetic engineering technology such as recombinant DNA technology). Preferred modes of transfer include techniques of restriction digestion, PCR amplification, or homologous recombination.

In one embodiment, a eukaryotic/prokaryotic multi-chain display shuttle vector as described and taught herein is employed. The genetic control elements of the dual display vector of the present invention provide, within a eukaryotic host cell, for the expression, processing, assembly, and display of a biologically active multi-chain polypeptide on the surface of the eukaryotic host cell transformed with the dual display vector, as well as provide, within a prokaryotic host cell, for the expression, processing, assembly, and display of a biologically active multi-chain polypeptide on the surface of a bacteriophage infected in the prokaryotic host cell.

In another embodiment, the phage display-eukaryotic display transfer system is performed by inserting chain-encoding polynucleotide segments excised from a conventional phage display vector (i.e., a bacteriophage engineered to display an exogenous polypeptide on the surface of the phage particle) known in the art, into the multi-chain eukaryotic display vector of the present invention, thereby enabling expression of the chain-encoding segments, and eukaryotic processing, assembly, and display of a biologically active multi-chain polypeptide on the surface of a eukaryotic host cell transformed with the eukaryotic display vector. As described above, transfer of the polynucleotide sequences from a phage display vector to a multi-chain eukaryotic display vector can be achieved by any genetic engineering technique known in the art. Two particularly preferred methods include a single excision/insertion transfer method and a multiple (or modular) excision/insertion transfer method.

In a single excision/insertion transfer process, the polynucleotide segments that encode the chains of a multi-chain polypeptide are excised (e.g., via restriction digestion) from the phage display vector as a single, unitary nucleic acid, and subsequently inserted into the multi-chain display vector. Once inserted into the eukaryotic display vector, unwanted prokaryotic genetic control elements (if any) positioned between the chain encoding polynucleotides are replaced with eukaryotic genetic control elements. This process is diagramed for an Ig Fab multi-chain polypeptide, transferred from a phage display vector to a particularly preferred multi-chain yeast display vector of the present invention in FIG. 1.

Figure 2:
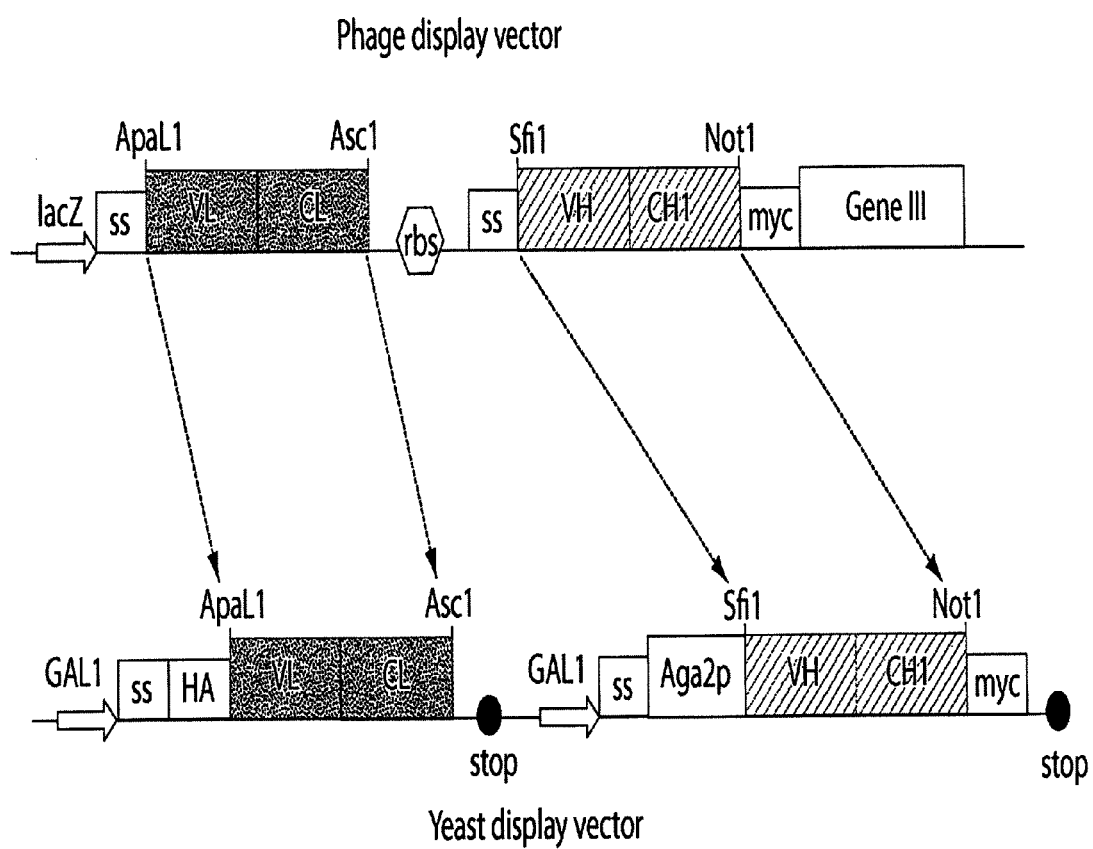
FIG. 2 is a schematic diagram that illustrates the phage display/eukaryotic display transfer system wherein the genetic information encoding the chains of a Fab polypeptide are independently and separately transferred from a phage display vector to a multi-chain eukaryotic vector of the present invention.

Alternatively, polynucleotide segments encoding chains of a multi-chain polypeptide are excised from the phage display vector individually, and subsequently inserted into the multi-chain display vector in a separate and independent manner. This approach provides greater control and flexibility over the transfer of individual chains of a multi-chain polypeptide separately or en masse. Indeed, depending upon the practitioner's interests and needs, only select chains of the multi-chain polypeptide need to be transferred. This process is diagramed for an Ig Fab multi-chain polypeptide in FIG. 2.

Practitioners skilled in the art will appreciate that the phage display-eukaryotic display transfer system described and taught herein is equally functional whether transferring sequence information from a phage display vector to a multi-chain eukaryotic display vector, or from a multi-chain eukaryotic display vector to a phage display vector; i.e., the phage display-eukaryotic display transfer system of the present invention is effectively bi-directional. A particularly preferred phage display library for use in the phage display-eukaryotic display transfer system according to the invention is a large human Fab fragment library (de Haard, H. et al., 1999).

Multi-Chain Eukaryotic Display Libraries and Screening Protocols Thereof

Multi-chain eukaryotic display vectors of the present invention, and host cells transformed with these vectors such that a biologically active multi-chain polypeptide in displayed on the host cell surface, are useful for the production of display libraries. Such display libraries are, in turn, useful to screen for a variety of biological activities of interest to the practitioner; e.g., to screen against any of a variety of target molecules to identify binding polypeptides specific for that target.

Several methods exist for expressing a variable array of molecules on the surface of a host cell or phage. Phage display libraries, and the screening of the same, represent a powerful research and development tool. Methods for producing and screening phage display libraries are well known and used in the art (Hoogenboom, H. et al., 1997; Kay et al., 1996; Ladner, R et al., 1993).

The multi-chain eukaryotic display vectors of the present invention can be used to generate novel peptide libraries de novo, similar to known phage display libraries. However, the vectors described herein provide allow for more efficient expression of properly folded, assembled, glycosylated, and displayed multi-chain polypeptides, as can only be achieved in a eukaryotic system. These multi-chain eukaryotic display libraries can then be used in screening assays. Persons of ordinary skill in the art will appreciate and easily adapt display library screening protocols known in the art (e.g., phage display screen assays) to the multi-chain eukaryotic display libraries of the present invention.

In addition to generating novel multi-chain eukaryotic display libraries de novo, the present invention further enables the practitioner to transfer existing phage display libraries to the multi-chain eukaryotic display system disclosed and taught herein. In particular, the phage display-eukaryotic display transfer system allows a phage display library to be constructed for the display of a very large repertoire of multi-chain polypeptides; for example Fabs, which have light chain and heavy chain components. The phage display library, which can have a diversity of $>1\times10^8$ (preferably $>1\times10^8$, more preferably $>1\times10^{10}$) different multi-chain polypeptides in a library, can undergo an initial screen, producing a sub-population of less than about $1\times10^7$ (preferably between $1\times10^5$ to $1\times10^6$) phage display isolates. The polynucleotides encoding the chains of the multi-chain polypeptide isolates can then be "batch transferred" to a multi-chain eukaryotic display vector of the present invention for transformation into a eukaryotic host. The multi-chain polypeptides displayed on eukaryotic host cells can be further screened and manipulated, taking advantage of the culture conditions and expression qualities of the eukaryotic host system as discussed earlier (e.g., protein folding, proper association of separate chains in the multi-chain protein, glycosylation, secretion, and post-translational modifications such as phosphtidyl inositol linkages to the cell membrane). In addition, once inserted into the multi-chain eukaryotic display vector, the multi-chain polypeptide library (or pre-selected isolates therefrom) can be further diversified (e.g., polypeptide chain recombination, re-shuffling, or re-mixing) for additional rounds of screening.

In a particularly preferred embodiment, a M13 phage expression vector is provided having:
  an Ig light chain cloning site defined by an ApaLI restriction site and an AscI restriction site, and which is oriented 3' to a signal sequence (e.g., a pIII signal sequence) and under the transcriptional control of a LacZ promoter; and
  an Ig heavy chain fragment cloning site defined by a SfiI restriction site and a NotI restriction site, and which is oriented 3' to a signal sequence (e.g., a pIII signal sequence), under the transcriptional control of a LacZ promoter, and 5' to a sequence encoding mature pIII or an anchoring portion of pIII (stump).

The multi-chain eukaryotic display vector in this preferred embodiment is a yeast vector having:
  an Ig light chain cloning site defined by an ApaLI restriction site and an AscI restriction site, and which is oriented 3' to an Aga2p secretion signal and under the transcriptional control of a GAL promoter (preferably GAL1 or GAL1-10); and
  an Ig heavy chain fragment cloning site defined by a SfiI restriction site and a NotI restriction site, and which is oriented 3' to an Aga2p secretion signal, under the transcriptional control of a GAL promoter (preferably GAL1 or GAL1-10), and 3' to a sequence encoding mature Aga2p.

The yeast expression vector is used to transform a yeast host cell for expression of antibodies or Fab fragments displayed on the yeast cell surface. Light and heavy chain coding sequences are excised individually (by ApaLI/AscI digestion and SfiI/NotI digestion respectively), or together (by ApaLI/NotI digestion) from the phage display vector, and inserted into the multi-chain yeast display vector by batch transfer, yielding a multiplicity of LC/HC chain pairings for expression and display in yeast. A particularly preferred yeast display vector for yeast display of Fabs is pTQ3 (described below). A particularly preferred phage display is a large human Fab fragment library (de Haard, H. et al., 1999).

It will be appreciated by one skilled in the art that the above methods are useful for identifying and isolating multi-chain polypeptides possessing a variety of detectable characteristics (e.g., catalytic activity, peptide interactions, thermal stability, desirable expression levels) or any other improvement that is selectable via surface expression of a displayed multi-chain polypeptide.

It will be further appreciated that the present invention can be used for the production of antibodies or antibody fragments useful for immunopurification, immunoassays, cytochemical labeling and targeting methods, and methods of diagnosis or therapy. For example, the antibody or fragment can bind to a therapeutically active protein such as interferon or a blood clotting factor such as, for example, Factor VIII, and can therefore be used to produce an affinity chromatography medium for use in the immunopurification or assay of the protein.

Multi-Chain Polypeptide Display as a Product of Cellular Fusion

The basic life cycle of eukaryotic cells involves an alternation between diploid (two copies of an organism's chromosomes or genome per cell) and haploid (one copy of an organism's chromosomes or genome per cell) states. The alternation between these two states is achieved by the fusion of two haploid cells (typically, although not necessarily, the fertilization of opposite mating types) to form a single diploid cell, and meiotic division of a diploid cell to form multiple haploid (daughter) cells. Biologists appreciate that this basic life cycle (i.e., the alternation of haploid and diploid generations) provides an important natural mechanism for the biological recombination genetic information (i.e., sexual reproduction).

In most animals, the diploid state is the dominant stage of the life cycle, generated by the fusion of two haploid cells (commonly referred to as gametes) of opposite mating type; a sperm and an egg. Meiotic cell division of diploid cells (gametogenesis) produces the haploid cell state for sexual reproduction.

The life cycle pattern of the plant kingdom provides a more general alternation of generation wherein the haploid and diploid state can exist as more distinct generations, depending on the particular plant species. In "lower" (i.e., more primitive) plants, the generation of the haploid cell (the "gametophyte") predominates (e.g., mosses, liverworts, and hornworts); whereas in "higher" (i.e., more advanced) plants, the generation of the diploid cell (the "sporophyte") predominates (e.g., ferns, conifers, and flowering plants).

For many fungi and protists, the haploid stage of the life cycle predominates. Fertilization produces a diploid stage, which often almost immediately (depending upon environmental conditions) undergoes meiosis to form haploid cells. Importantly, and regardless of which genera of organism is being discussed or which stage dominates the organism's life cycle, the natural recombination and re-mixing of genetic material that results from meiosis of diploid cells to produce haploid cells, and the cellular fusion of separate haploid cells to produce diploid cell (of a new genetic admixture) is a powerful process that can be utilized in biological research. Described and taught herein for the first time, this powerful mechanism is utilized in combinatorial protein research for the generation of unique multi-chain peptide display libraries.

In a further aspect of the present invention, the mode for introducing eukaryotic multi-chain display vectors into a host cell includes the fusion of two eukaryotic cells, preferably haploid, each expressing at least one of the chains of the multi-chain polypeptide, such that the biological activity of the multi-chain polypeptide is exhibited at the surface of the resulting host cell, preferably diploid. For example, each of the two haploid cells can contain one of the vectors of a vector set (as described herein), such that once combined (e.g., via cellular fusion of host cells) and co-expressed in the resulting diploid host cell, the biological activity of the multi-chain polypeptide is exhibited at the surface of the host cell. Such methods can be used to prepare novel multi-chain polypeptide libraries as described above (for example, antibody or Fab display libraries, including diploid host cells displaying multi-chain polypeptides having a greater diversity than the source repertoire).

Alternatively, populations of a matched vector set can be constructed such that one eukaryotic expression vector population expresses multiple (e.g., a repertoire or library) forms of an Ig Fab light chain (comprising $V_L$ and $C_L$ domains) and a second eukaryotic expression vector population expresses multiple forms of an Ig Fab heavy chain (comprising $V_H$ and $C_H1$ domains) fused to a yeast anchor protein (e.g., Aga2p). Each of the vector populations are used to transform haploid yeast cells of opposite mating type; one vector construct in one mating type, the second vector construct in the opposite mating type. The two haploid yeast populations are co-cultured under conditions sufficient to induce yeast mating (i.e. cellular fusion) of the two mating types. The resulting diploid yeast host cells of the population possess both vector constructs and expresses and displays the fully formed and assembled Ig Fab.

Although, as discussed above, any eukaryotic cell capable of cell fusion can be used in the present invention. Cell fusion can occur sexually by mating, or artificially, e.g., in tissue culture or other artificial conditions. In the case of sexual cell fusion, any eukaryotic cell is suitable as long as it is capable of existing (no matter how briefly) in both a haploid and a diploid state. For artificial cell fusion, cells are not limited by ploidy as they would be in the case of sexual fusion. For example, diploid mammalian cells maintained in tissue culture can be induced to fuse, thereby resulting in a tetraploid host cell. For the present invention, the actual ploidy of the host cells to be fused does not pose a limitation so long as the cells can be fused. The important features of the cells are that one cell partner contains a vector or vector set comprising a particular chain of a multi-chain polypeptide and a specific selectable marker, and the partner host cell contains a vector or a vector set comprising a second chain of a multi-chain polypeptide and a selectable marker. When the cells are fused, therefore, the resultant fused cell contains vectors encoding two or more chains of a multi-chain polypeptide in a cell that is readily identified by the selectable markers.

Fungi, especially sac fungi (ascomycetes; e.g., *Neurospora* and yeasts), are particularly preferred eukaryotic host cells. Sac fungi are so named because they produce the haploid spore products of meiosis in microscopic sacs, which render them easily collected, segregated, analyzed, and manipulated (*Neurospora* are particularly noted because the size and shape of their ascus maintains the order of the haploid cell products of meiosis). Also, these fungi, especially *S. cerevisiae*, exist stably in both haploid and diploid form, either of which are easily induced and maintained (e.g., the yeast haploid state is typically induced and maintained under some form of nutritional stress, i.e., starvation). Finally, in many fungi (again especially preferred yeast) haploid cells exist as two sexes (the α and α mating types), from which only opposite mating types fuse (mate) to form the diploid state. Under conditions manipulable in the lab by one of skill in the art, an α cell will fuse to an α cell, thereby creating a fused diploid cell.

As noted above, artificial methods of fusing cells are known in the art. Therefore the present invention is suitable for eukaryotic cells such as, for example, mammalian, insect or plant cells that are grown in culture. Additionally, yeast protoplasts or spheroplasts can be manipulated to undergo cell fusion even if they are of the same mating type. Such artificial methods for cell fusion are known in the art and would be suitable for the purposes of the present invention.

Finally, practitioners skilled in the art will recognize and appreciate that the products and methods described and demonstrated herein are not limited by a eukaryotic host cell of a particular ploidy. Indeed, other polyploid organisms (e.g., rarer triploid and tetraploid forms) can be used especially as hosts for matched vector sets expressing higher order multi-chain polypeptides (e.g., three-chain and four-chain polypeptides respectively).

Multi-Chain Polypeptide Screening Using a Eukaryotic Cellular Fusion

Multi-chain polypeptides libraries displayed on eukaryotic host cells can be screened and manipulated similar to procedures and techniques known in the art, e.g., phage display library screening, but also allow the practitioner to take advantage of culture conditions and expression qualities of a eukaryotic host system. As discussed above, eukaryotic display screening can be prefaced with an initial round of phage display screening before transferring the display library from the phage display vector to a multi-chain eukaryotic display vector. Once inserted into the multi-chain eukaryotic display vector, the multi-chain polypeptide library (or pre-selected isolates) can be subjected to one or more additional rounds of screening under the eukaryotic display system.

As a further embodiment of the screening methods of the present invention, and unique to the methods of the present invention, multi-chain eukaryotic display libraries can undergo further (biased or unbiased) diversification subsequent to any screen assay utilizing the alternation of generations characteristic of eukaryotic systems as discussed above. Populations of diploid eukaryotic host cells containing a multi-chain eukaryotic display vector, wherein different chains of the multi-chain are expressed from different vectors (e.g., where the diploid host cell is the product of haploid mating or cell fusions as described above), can be induced to undergo meiosis (e.g., sporulation in yeast). The haploid yeast cells (spores) can be segregated and/or selected depending on screening conditions in order to isolate different eukaryotic expression vectors with a preferred property of interest in separate haploid daughter cells. The daughter cells can then be optionally:

mutagenized (variegated) in vitro (e.g., isolated DNA manipulation) or in vivo (e.g., UV light) to provide a multiplicity of homologs of the pre-selected chains. When these homologous chains are co-expressed and displayed, homologous multi-chain polypeptides having greater affinities for the same target molecule can be selected; or fused back together with other daughter host cells, thus recombining individual pre-selected chains of the multi-chain polypeptide isolates among themselves; or fused with the initial multi-chain library host cell population, thus recombining pre-selected chains of the multi-chain polypeptide isolates with the original source of multi-chain variation; or fused with a new multi-chain library host cell population; thus combining the pre-selected chains of the multi-chain polypeptide isolates with a new source of multi-chain variability; or any combination of any of the above steps as appropriate.

Once this recombination, re-shuffling, or re-mixing of pre-selected chains of a multi-chain polypeptide screen among themselves or with another source of multi-chain diversity is complete, the new admixture library population can undergo further rounds of new or repeat screening.

The present invention incorporates by reference in their entirety techniques well known in the field of molecular biology. These techniques include, but are not limited to, techniques described in the following publications:

Ausubel, F. et al., eds., *Short Protocols In Molecular Biology* (4th Ed. 1999) John Wiley & Sons, NY, N.Y. (ISBN 0-471-32938-X).

Fink and Guthrie, eds., *Guide to Yeast Genetics and Molecular Biology* (1991) Academic Press, Boston, Mass. (ISBN 0-12-182095-5).

Kay et al., *Phage Display of Peptides and Proteins: A Laboratory Manual* (1996) Academic Press, San Diego, Calif.

Kabat, E. et al., *Sequences of Proteins of Immunological Interest* (5th Ed. 1991) U.S. Dept. of Health and Human Services, Bethesda, Md.

Lu and Weiner, eds., *Cloning and Expression Vectors for Gene Function Analysis* (2001) BioTechniques Press. Westborough, Mass. (ISBN 1-881299-21-X).

Old, R. and Primrose, S., *Principles of Gene Manipulation: An Introduction To Genetic Engineering* (3d Ed. 1985) Blackwell Scientific Publications, Boston, Mass. Studies in Microbiology; V.2:409 (ISBN 0-632-01318-4).

Sambrook, J. et al., eds., *Molecular Cloning: A Laboratory Manual* (2d Ed. 1989) Cold Spring Harbor Laboratory Press, NY, N.Y. Vols. 1-3 (ISBN 0-87969-309-6).

Winnacker, E., *From Genes To Clones: Introduction To Gene Technology* (1987) VCH Publishers, NY, N.Y. (translated by Horst Ibelgaufts). (ISBN 0-89573-614-4).

REFERENCES

Boder, E. and Wittrup, K. 1998. *Biotechnol. Prog.*, 14:55-62.
Chang, H. et al., 1994. *Proc. Natl. Acad. Sci. USA*, 91:11408-12.
Crameri, R. and Blaser, K., 1996. *Int. Arch. Allergy Immunol.*, 110:41-45.
Crameri, R. and Suter, M., 1993. *Gene*, 137:69-75.
de Haard, H. et al., 1999. *J. Biol. Chem.*, 274:18218-18230.
Fields, S, and Sternglanz, R., 1994, *Trends Genet.*, 10:286-292.
Gietz, D. et al., 1992. *Nucleic Acids Res.*, 20:1425.
Hoogenboom, H. et al., 1997. *Trends Biotechnol.*, 15:62-70.
Horwitz, A. et al., 1988. *Proc. Natl. Acad. Sci. USA*, 85:8678-8682.
Kieke, M. et al., 1997. *Protein Eng.*, 10:1303-1310.
Kieke, M. et al., 1999. *Proc. Natl. Acad. Sci. USA*, 96:5651-5656.
Ladner, R. et al., 1993, U.S. Pat. No. 5,223,409.
Liu, Q. et al., 2000. *Methods Enzymol.*, 328:530-549.
Moll, J. et al., 2001. *Protein Sci.*, 10:649-55.
Munro, S, and Pelham, H., 1987. *Cell*, 48:899.
Phizicky, E. and Fields, S., 1995. *Microbiol. Rev.*, 59:94-123.
Pu, W. and Struhl, K., 1993. *Nucleic Acids Res.*, 21:4348-55.
Walhout, A. et al., 2000. *Methods Enzymol.*, 328:575-593.
Wittrup et al., WO 99/36569.

This invention is illustrated further by the following examples, which are not to be construed as limiting in any way.

EXAMPLES

Example 1

Construction of a Multi-Chain Eukaryotic Display Vector: pTQ3

The materials and techniques described above and incorporated by reference were used to construct a multi-chain eukaryotic display vector; specifically a yeast display vector effective in a host yeast cell transformed with the vector. The vector is useful for expressing, transporting, assembling and displaying a biologically active multi-chain polypeptide (e.g., an Ig Fab) on the surface of the host yeast cell.

In this example, a commercially available vector, pYD1 (InVitrogen, Carlsbad, Calif.), a 5.0 kb expression vector designed for expression, secretion, and display of a single chain protein on the surface of S. cerevisiae cells, was used as the starting eukaryotic expression vector template. pYD1 includes: an aga2 gene encoding one of the subunits of the α-agglutinin receptor; a GAL1 promoter for regulated expression of an Aga2/polypeptide fusion; an HA epitope tag for detection of the displayed protein; a polyhistidine (6×His) tag for purification on metal chelating resin; a CEN6/ARS4 for stable, episomal replication in yeast; and a TrpI gene for S. cerevisiae transformant selection, an ampicillin resistance gene (ampR) and the pMB1 origin for selection and replication in E. coli.

The pYD1 plasmid was modified for expression of an Ig light chain and a heavy chain fragment from two tandem galactose inducible promoters, for the display of an intact Fab antibody fragment. One GAL1 promoter directs expression of the light chain and the other GAL1 promoter directs expression of the heavy chain fragment fused to the C-terminus of the Aga2p yeast anchor protein.

In order to effectively transfer the chains of a multi-chain polypeptide into the display vector, unique restriction sites were generated as part of the vector construct. The restriction endonuclease recognition sequences (i.e., restriction sites) chosen for this vector construct included ApaLI, AscI, SfiI, and NotI as the unique cloning sites for the chains of a two-chain polypeptide (in this case an Ig Fab), and NheI to facilitate phage display-eukaryotic display transfers with existing phage display libraries.

Several vector sequence modifications were made to ensure effective use of ApaLI as a unique restriction site. The ApaLI sites located on the pYD1 plasmid (as supplied by InVitrogen) starting at positions 1393, 3047, and 4293 were removed by site-directed mutagenesis (using QUICKCHANGE, Stratagene, La Jolla, Calif.) as indicated below:

| pYD1 position | ApaLI nucleotide change |
|---|---|
| 1393 | GTGCAC to GTGCAG |
| 3047 | GTGCAC to GTGCTC |
| 4293 | GTGCAC to GAGCAC |

The ApaLI site beginning at position 3047 lies within the ampR, requiring a silent mutation so as not to change the amino acid coding sequence of this gene.

In order to render the multi-chain yeast display vector construct compatible with other pre-existing phage display vectors known in the art (Dyax Corp., Cambridge, Mass.), a unique restriction site was introduced into the pYD1 vector aga2p signal sequence without altering the coding sequence, using PCR site directed mutagenesis techniques known in the art. Specifically, a NheI site was created across the terminal serine codon of the aga2p signal sequence by replacing codon TCA with codon AGC.

The vector thus modified having a unique ApaLI site immediately 3' to the pre-existing GAL1 promoter-aga2p signal sequence-HA tag segments, followed by a AscI site, and a NheI site incorporated in the aga2p signal sequence was designated pTQ2.

Assembly PCR techniques known in the art were used to construct a polylinker compatible with existing phage display libraries for excision/insertion of structural genes for the light chain component of a Fab into the multi-chain yeast display vector. The resulting intermediate multi-chain eukaryotic display vector segment spanning the apa2p signal sequence through the designed polylinker site is as follows (* indicates stop codons):

```
                                                        NheI
ATG CAG TTA CTT CGC TGT TTT TCA ATA TTT TCT GTT ATT GCT AGC GTT
 M   Q   L   L   R   C   F   S   I   F   S   V   I   A   S   V
                          Aga2p signal sequence ApaLI
TTA GCA TAC CCA TAC GAC GTT CCA GAC TAC GCT AGT GCA CAG GAT
 L   A   Y   P   Y   D   V   P   D   Y   A   S   A   Q   D
                    HA epitope tag AscI              BamHI                   PstI
TTC GTG CAA TGC GGC GCG CCA GGA TCC GCC TGA ATG GTC TGC AGA
 F   V   Q   C   G   A   P   G   S   A   *   M   V   C   R EcoRI                         PacI
CCG TAC CGA CCG AAT TCG AGT TAC CTG AGG TTA ATT AAC ACT GTT
 P   Y   R   P   N   S   S   Y   L   R   L   I   N   T   V PmeI
ATC GTT TAA ACG TTC AGG TGC AA (SEQ ID NO: 1)
 I   V   *   T   F   R   C     (SEQ ID NO: 2)
```

A MATα transcriptional terminator sequence was amplified by PCR from the pYD1 plasmid, and BamHI and PstI restriction sites were appended to facilitate cloning into plasmid pTQ2 above. The MATα terminator was then digested with BamHI and PstI and inserted into the BamHI/PstI site on plasmid pTQ2.

A DNA construct including (5'-3'); the GAL1 promoter, the aga2p signal sequence, the Aga2p protein coding sequence, and a glycine/serine linker, was amplified from plasmid pYD1. A DNA linker segment containing SfiI and NotI restriction sites and a segment coding for a myc tag were added at the 3' end of the amplified pYD1 segment. The myc tag was included to allow detection of the anchored chain (of the multi-chain polypeptide) on the yeast cell surface. The linker-myc segment sequences is as follows:

```
GGA GGC GGA GGT TCT GGG GGC GGA GGA TCT GGT GGC GGA GGT TCT
 G   G   G   G   S   G   G   G   G   S   G   G   G   G   S

SfiI                                NotI
GCG GCC CAG CCG GCC AGT CCT GAT GCG GCC GCA GAA CAA AAA CTC
 G   G   Q   P   G   S   P   D   A   A   A   E   Q   K   L

PacI
ATC TCA GAA GAG GAT CTG AAT TTA ATTAA  (SEQ ID NO: 3)
 I   S   E   E   D   L   N            (SEQ ID NO: 4)
```

Figure 3:
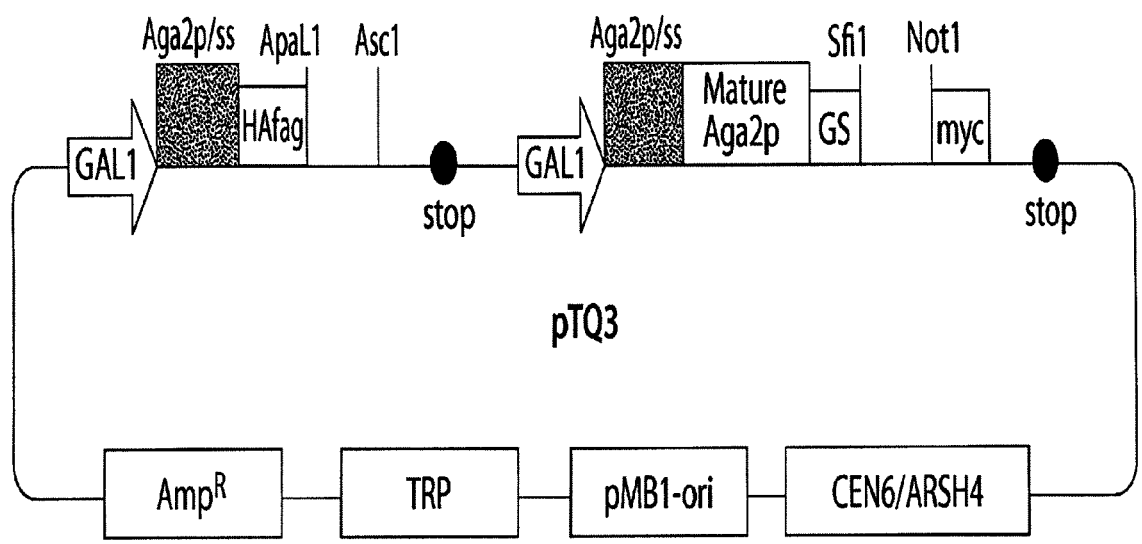
FIG. 3 is a schematic diagram of the multi-chain yeast display vector, pTQ3, according to the invention, having unique cloning sites for insertion of at least two chains of a multi-chain polypeptide (e.g., Fab light and heavy chain components), with additional elements arranged so that the two chains are independently expressed by induction of tandem GAL1 promoters. In this vector, a first chain (e.g., an Ig light chain), inserted as an ApaLI/AscI fragment, is expressed as a soluble secretory protein using the Aga2p signal sequence (Aga2p/ss) and fused with an HA epitope tag. A second chain (e.g., an Ig heavy chain fragment), inserted as an SfiI/NotI fragment, is expressed as a cell surface bound fusion protein using the Aga2p/ss and anchoring protein subunit (mature Aga2p). The second chain is similarly fused with a myc epitope tag. Other elements useful for plasmid replication (e.g., pMB1-ori and Cen6/ARSH4) and useful as selective markers (i.e., ampR and TRP) are also indicated.

This linker-myc segment was inserted into an EcoRI and PacI digested pTQ2. The resulting plasmid, with unique cloning sites for insertion/excision of the chains of a multi-chain polypeptide (specifically light chain and heavy chain fragments of a Fab), was designated pTQ3 (FIG. 3). Plasmid pTQ3 is a 5810 bp multi-chain yeast display plasmid comprising, in pertinent part, the following vector sequence:

```
     <----------------------Aga2p signal sequence---------
     ATG CAG TTA CTT CGC TGT TTT TCA ATA TTT TCT GTT ATT GCT
      M   Q   L   L   R   C   F   S   I   F   S   V   I   A ---------------> <-------------HA tag--------------->
     AGC GTT TTA GCA TAC CCA TAC GAC GTT CCA GAC TAC GCT
      S   V   L   A   Y   P   Y   D   V   P   D   Y   A ApaLI                          AscI       BamHI
     AGT GCA CAG GAT TTC GTG CAA TGC GGC GCG CCA GGA TCC
      S   A   Q   D   F   V   Q   C   G   A   P   G   S

ATG TAA
      M        (SEQ ID NO: 6)

<--------------------Mat α terminator-------------------->
     661 CAAAATCGACTTTGTTCCCACTGTACTTTTAGCTCGTACAAAATACAATATACTTTTCAT

721 TTCTCCGTAAACAACATGTTTTCCCATGTAATATCCTTTTCTATTTTTCGTTCCGTTACC

781 AACTTTACACATACTTTATATAGCTATTCACTTCTATACACTAAAAAACTAAGACAATTT

841 TAATTTTGCTGCCTGCCATATTTCAATTTGTTATAAATTCCTATAATTTATCCTATTAGT

EcoRI
     901 AGCTAAAAAAAGATGAATGTGAATCGAATCCTAAGAGAATTCACGGATTAGAAGCCGCCG

<---------------------GAL1 promotor--------------------->
     961 AGCGGGTGACAGCCCTCCGAAGGAAGACTCTCCTCCGTGCGTCCTCGTCTTCACCGGTCG

1021 CGTTCCTGAAACGCAGATGTGCCTCGCGCCGCACTGCTCCGAACAATAAAGATTCTACAA

1081 TACTAGCTTTTATGGTTATGAAGAGGAAAAATTGGCAGTAACCTGGCCCCACAAACCTTC

1141 AAATGAACGAATCAAATTAACAACCATAGGATGATAATGCGATTAGTTTTTTAGCCTTAT

1201 TTCTGGGGTAATTAATCAGCGAAGCGATGATTTTTGATCTATTAACAGATATATAAATGC

1261 AAAAACTGCATTAACCACTTTAACTAATACTTTCAACATTTTCGGTTTGTATTACTTCTT

1321 ATTCAAATGTAATAAAAGTATCAACAAAAAATTGTTAATATACCTCTATACTTTAACGTC

1381 AAGGAGAAAAAACCCGGATCGGACTACTAGCAGCTGTAATACGACTCACTATAGGGAATA

1441 TTAAGCTAATTCTACTTCATACATTTTCAATTAAG

<--------------------------Aga2p signal sequence-----------------------
    1476 ATG CAG TTA CTT CGC TGT TTT TCA ATA TTT TCT GTT ATT GCT TCA GTT TTA GCA
          M   Q   L   L   R   C   F   S   I   F   S   V   I   A   S   V   L   A
```

-continued

```
                         ------->  <------------------Mature Aga2 protein-------------------
1530 CAG GAA CTG ACA ACT ATA TGC GAG CAA ATC CCC TCA CCA ACT TTA GAA TCG ACG
      Q   E   L   T   T   I   C   E   Q   I   P   S   P   T   L   E   S   T 1584 CCG TAC TCT TTG TCA ACG ACT ACT ATT TTG GCC AAC GGG AAG GCA ATG CAA GGA
      P   Y   S   L   S   T   T   T   I   L   A   N   G   K   A   M   Q   G 1638 GTT TTT GAA TAT TAC AAA TCA GTA ACG TTT GTC AGT AAT TGC GGT TCT CAC CCC
      V   F   E   Y   Y   K   S   V   T   F   V   S   N   C   G   S   H   P ------->
1692 TCA ACG ACT AGC AAA GGC AGC CCC ATA AAC ACA CAG TAT GTT TTT
      S   T   T   S   K   G   S   P   I   N   T   Q   Y   V   F <----------Glycine-Serine linker-------------------------->
1736 GGA GGC GGA GGT TCT GGG GGC GGA GGA TCT GGT GGC GGA GGT TCT
      G   G   G   G   S   G   G   G   G   S   G   G   G   G   S SfiI                      NotI      <----------myc tag---------
1782 GCG GCC CAG CCG GCC AGT CCT GAT GCG GCC GCA GAA CAA AAA CTC ATC TCA GAA
      A   A   Q   P   A   S   P   D   A   A   A   E   Q   K   L   I   S   E -------------->   PacI                 PmeI
1836 GAG GAT CTG AAT TTA ATT AAC ACT GTT ATC GTT TAAAC  (SEQ ID NO: 5)
      E   D   L   N   L   I   N   T   V   I   V         (SEQ ID NO: 7)
```

Later modifications were made to the above vector by inserting a 6×His tag for purification of soluble Fab antibodies and by repositioning the stop codon (TAA) at the end of the myc tag, before the PacI site, to eliminate superfluous amino acids. Other modifications have included the removal of an endogenous XbaI restriction site within the Trp selective marker by site directed mutagenesis. This was done to facilitate cloning and manipulation of lead antibodies from the CJ library set (Dyax Corporation, Cambridge, Mass.).

Example 2

Phage Display-Eukaryotic Transfer and Eukaryotic Host Cell Expression of Multi-Chain Fab Polypeptides Specific for Streptavidin, Mucin-1 and Cytotoxic T-Lymphocyte Associated Antigen 4

Different phage display Fabs were transferred from the phage display vector to a multi-chain eukaryotic display vector to demonstrate of the utility of the phage display-eukaryotic display transfer system, and the ability of the multi-chain eukaryotic vector of the present invention to express a multi-chain polypeptide. The vector was then inserted into a eukaryotic host cell, and the transformed host cell grown under conditions suitable for expression of the Fabs.

Anti-streptavidin Fab antibodies, F2, A12, and 4C8 were each cloned from a large naive human Fab library (de Haard, H. et al., 1999) into the multi-chain yeast display vector pTQ3 constructed in Example 1 as a paired light chain ($V_L C_L$) and heavy chain ($V_H C_H 1$). Additionally, an anti-mucin Fab antibody, PH1, was cloned from the same Fab library into the multi-chain yeast display vector pTQ3 constructed in Example 1 as a paired light chain ($V_L C_L$) and heavy chain ($V_H C_H 1$). Additionally, four antibodies, E7, E8, A9, A11, specific for cytotoxic T-lymphocyte associated antigen 4 (CTLA-4) were cloned from the same Fab library into the multi-chain yeast display vector pTQ3 constructed in Example 1 as a paired light chain ($V_L C_L$) and heavy chain ($V_H C_H 1$).

The chains of the Fabs were cloned into the multi-chain yeast display vector using the single excision/insertion transfer process described earlier and illustrated in FIG. 1. The LC-HC polynucleotide from the Fab library was inserted as a single ApaLI/NotI fragment. The unwanted prokaryotic genetic control elements intervening the coding regions of the LC and HC fragment and defined by the AscI/SfiI restriction fragment from the Fab library was replaced with the AscI/SfiI fragment derived from pTQ3.

The resulting plasmids, designated pTQ3-F2, pTQ3-A12, pTQ3-4C8, pTQ3-PH1, pTQ3-E7, pTQ3-E8, pTQ3-A9 and pTQ3-A11, were separately transformed into S. cerevisiae strain EBY100 (InVitrogen, Carlsbad, Calif.) following the method of Gietz, D. et al., 1992. EBY100 was also transformed pTQ3 containing no multi-chain insert as a control. Transformant selection was performed selecting for the vector tryptophan auxotrophic marker (synthetic defined medium minus tryptophan, 2% (w/v) glucose, 2% agar (SD-CAA+GA)).

Successful transformants (correspondingly designated "EBY100 pTQ3-F2", "EBY100 pTQ3-A12", "EBY100 pTQ3-4C8", "EBY100 pTQ3-PH1", "EBY100pTQ3-E7", "EBY100pTQ3-E8", "EBY100pTQ3-A9", "EBYpTQ3-A11", and the control "EBY100 pTQ3") were grown overnight at 30° C. with shaking in 10 mL SDCAA+G. Two samples of cells were immediately removed when the $OD_{600}$ reached 1.0 (e.g., 2 mL of a culture of $OD_{600}$ of 1.0) for protein lysate preparation as the time equals zero induction point ($T_0$). The following day, cultures were centrifuged and the pelletted yeast cells were resuspended in 10 mL SDCAA, 2% (w/v) galactose to an $OD_{600}$ of 1. Cells were grown at 20° C. to induce vector expression of the light and heavy chains for 48 hours. Cultured cells were then centrifuged and washed twice in 1 mL sterile water, and transferred to an eppendorf tube for centrifugation.

Cell pellets were resuspended in 250 mL of SDS-PAGE buffer plus dithiothreitol (DTT). 425-600 micron glass beads (Sigma, St. Louis, Mo.) were added to just below the meniscus, and the suspension was vortexed 4 times for 1 minute. The suspension was kept on ice between vortexing. The supernatant was transferred to a fresh tube and heated to 100° C. for 5 minutes.

Figure 4A:
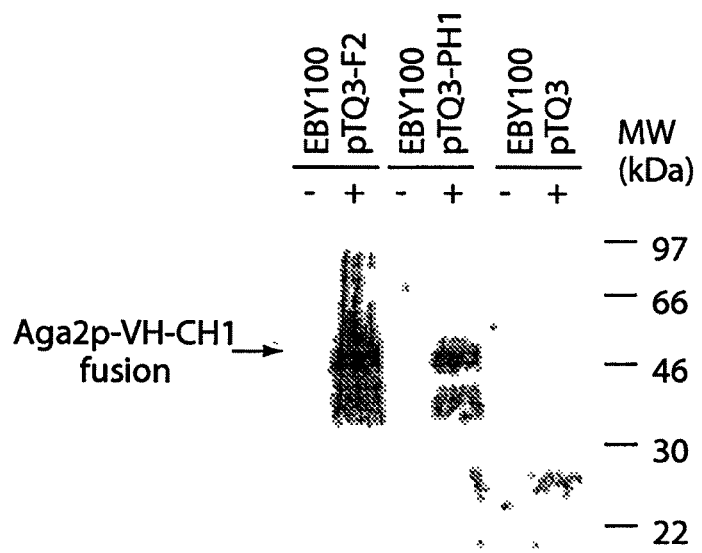
FIGS. 4A-4C are representations of data demonstrating independent expression of fusion proteins.
Figure 4B:
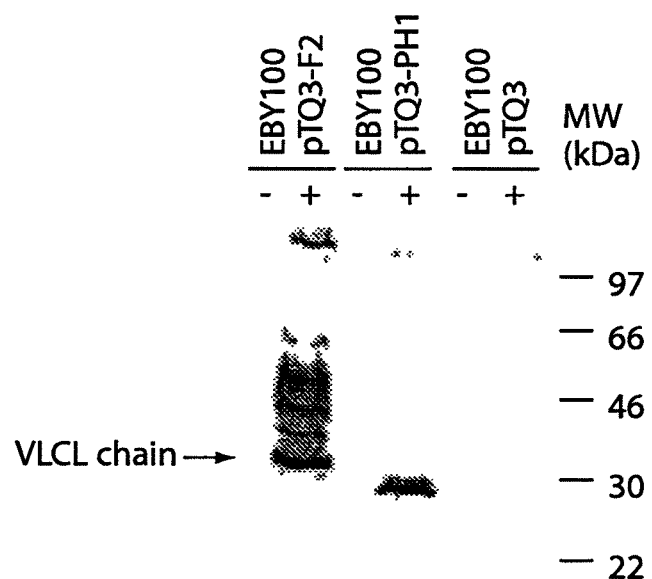

Protein samples were separated on a SOS-PAGE gel and transferred to a nitrocellulose membrane for western blotting. Detection of the light chain polypeptide was performed using an anti-HA antibody (1 µg/mL) (Dako, Carpinteria, Calif.). Detection of the heavy chain-Aga2p fusion polypeptide was performed using an anti-c-Myc antibody (1 µg/mL) in conjunction with a secondary rabbit anti-mouse HRP antibody (Dako, Carpinteria, Calif.). Immunodetection was by enhanced chemiluminescence (Amersham-Pharmacia, Piscataway, N.J.). The LC product of approximately 30 kD and the HC-Aga2p fusion product of approximately 45 kD of the displayed Fabs (F2 and PH1; FIGS. 4A and 4B) were detected. No detectable LC or HC-Aga2p fusion product was detected prior to induction with galactose (see FIGS. 4A and 4B).

Example 3

Functional Surface Display of a Multi-Chain Polypeptide on a Eukaryotic Host Cell As a demonstration of the ability of the multi-chain eukaryotic vector of the present invention to express, assemble and properly display a biologically active multi-chain polypeptide on the surface of a eukaryotic host cell, a multi-chain eukaryotic display vector was inserted into a eukaryotic host cell and the transformed host cell was grown under conditions suitable for expression and display of the Fab on the surface of the host cell.

Yeast clones EBY100 pTQ3-F2, EBY100 pTQ3-PH1, EBY100 pTQ3-E7, EBY100 pTQ3-E8, EBY100 pTQ3-A9 and EBY100 pTQ3-A11 were prepared, cultured, and induced for antibody expression as described in Example 2 above. Three 0.2 mL aliquots of yeast cells having an $OD_{600}$ of 1.0 were removed prior to induction with galactose, as the $T_0$ point.

After inducing expression with galactose (Example 2), three additional 0.2 mL aliquots of cells having an $OD_{600}$ of 1.0 were removed. Yeast samples were centrifuged and the cell pellet resuspended in PBS containing 1 mg/mL BSA.

Two samples were again centrifuged and the cell pellets resuspended in either 100 mL of anti c-Myc antibody (2.5 µg per sample), or 100 mL of anti-HA antibody (2.0 µg antibody per sample). The samples were then incubated for one hour at room temperature, and the cells pelleted and washed once with 0.5 mL of PBS/BSA. The samples were then incubated with FITC-conjugated rabbit anti-mouse antibody (1:40 dilution) for 1 hour in the dark.

Cell samples were labeled with streptavidin-FITC (1:20 dilution) in PBS/1% (w/v) BSA and incubated overnight in the dark at room temperature. All samples were centrifuged and the cell pellets washed once with 0.5 mL PBS and then resuspended in 500 mL of PBS.

Figure 4C:
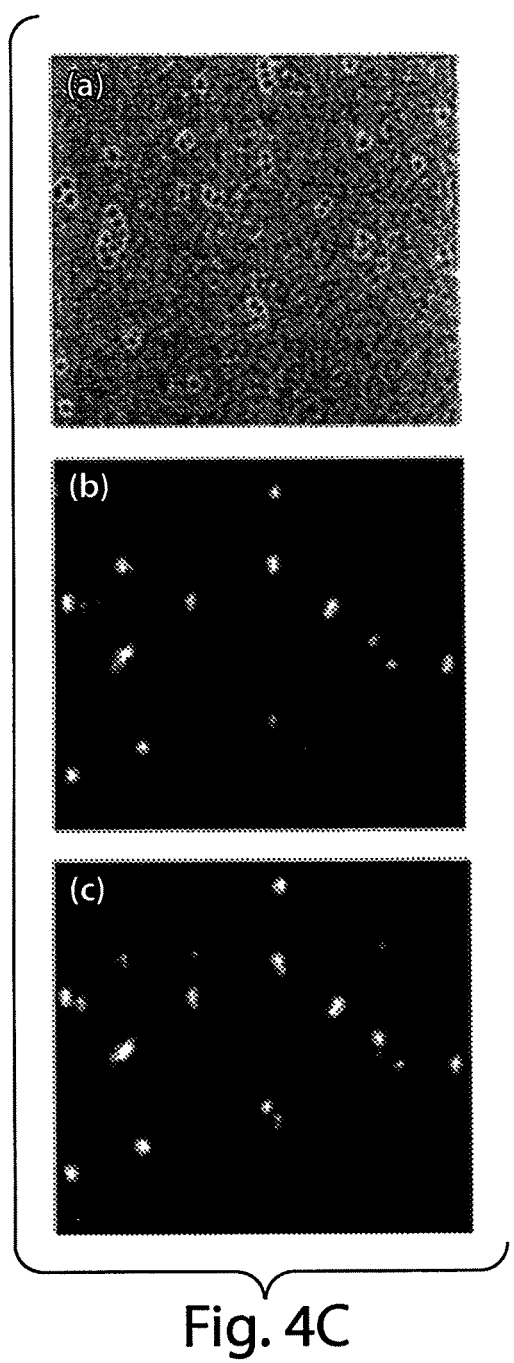
Figure 5A:
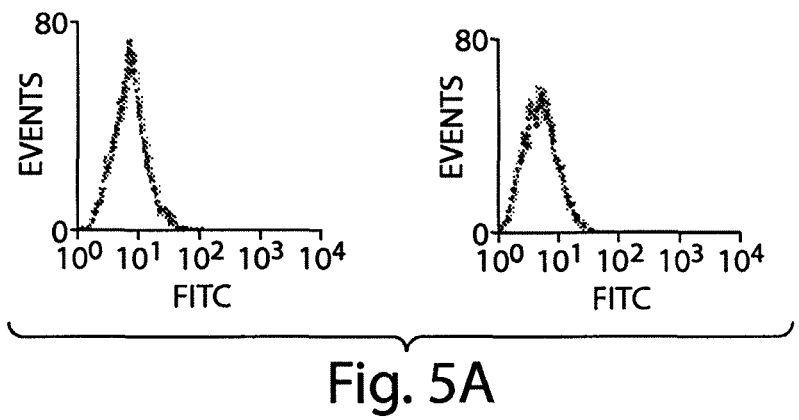
FIGS. 5A-C represent a series of cytometric plots.
Figure 5B:
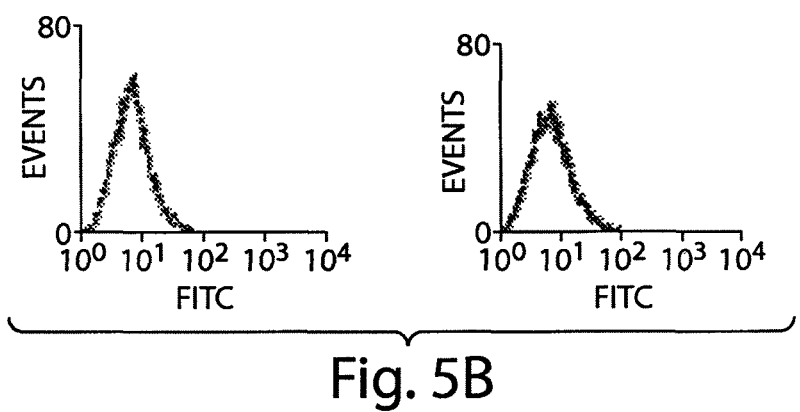
Figure 5C:
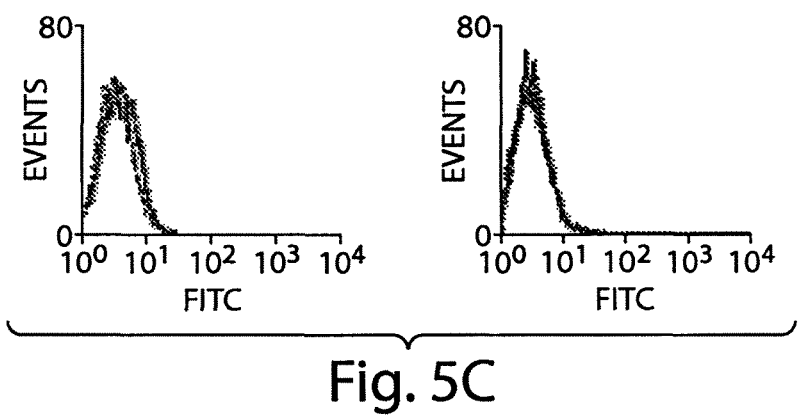
Figure 6:
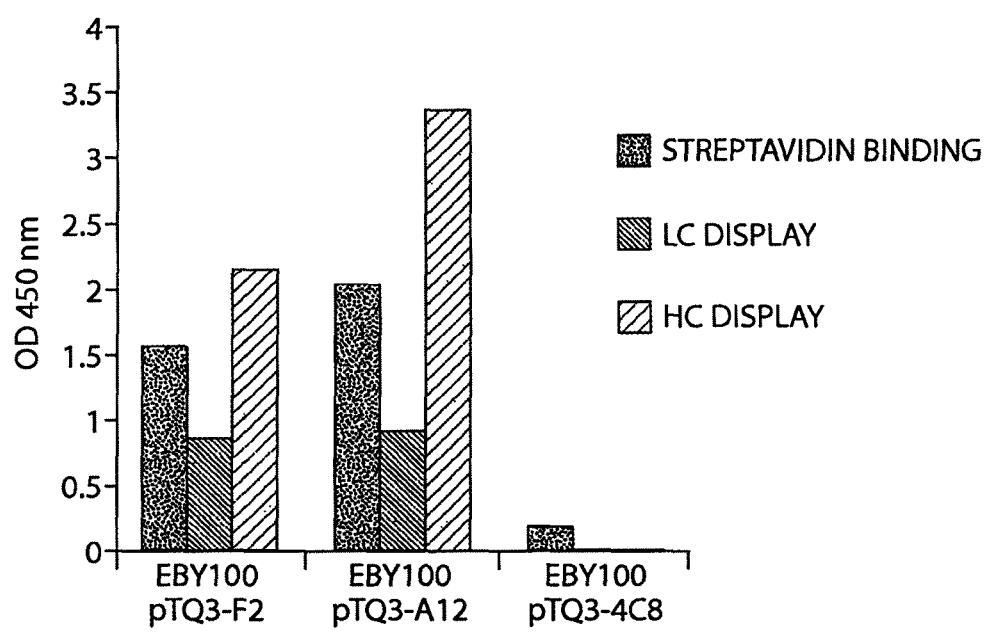
FIG. 6 is a histogram plot illustrating whole cell ELISA of three different anti-streptavidin Fabs displayed on the surface of yeast host cells EBY100 pTQ3-F2, EBY100 pTQ3-A12, and EBY100 pTQ3-4C8. Antigen binding, LC display and HC display are indicated respectively.

The presence of cell surface bound Fab-antigen binding was detected by flow cytometry. Cells prior to induction showed no display of light chain, heavy chain or functional streptavidin binding Fab antibody. After induction of Fab expression, yeast cells could be detected displaying LC, HC and also functional streptavidin binding Fab antibody by immunofluorescence (FIG. 4C), by FACS (FIG. 5A-C) and yeast whole cell ELISA (FIG. 6, see Example 7). Functional display of the anti-CTLA-4 Fab antibodies was also demonstrated (data not shown).

In the case of EBY100 pTQ3-F2 and EBY100 pTQ3-PH1 antigen binding as detected by FACS could be competed with unlabeled soluble antigen. Competitive binding showed the absolute specificity of the combinatorially assembled Fab antibody displayed on the yeast cell surface (FIG. 5C).

Example 4

Preferential Enrichment of Fab-Displaying Yeast Cells: Detection by Magnetic Bead Selection To demonstrate that yeast cells displaying an antigen-specific Fab antibody can be enriched over an excess of non relevant yeast cells, model selection experiments were performed using an automated magnetic bead selection device.

The Fab-displaying yeast cell EBY100 pTQ3-F2 (with a tryptophan auxotrophic selectable marker) were mixed with nonspecific yeast cells at various ratios. The non specific yeast cells consisted of EBY100 pUR3867 (Unilever Research, $V_L$aardingen, Netherlands), and encoding a scFv antibody specific for mucin-1 (PH1), and carrying a leucine auxotrophic selectable marker. The ratio of $Leu^+/Trp^+$ cells before and after selection was used to calculate the enrichment factor after 1 round of selection.

Yeast clones were grown and antibody expression induced with galactose as described in Example 2. The two yeast clones were mixed in the ratio indicated above, and incubated for 1 hour with 100 µL streptavidin paramagnetic beads (Dynal M280, Dynal Biotech, Oslo, Norway) in an end volume of 1 mL 2% a phosphate-buffered saline solution (e.g., 2% MARVEL-PBS or "MPBS", Premier Brands Ltd., U.K.).

After incubation of the yeast-bead mixture, the cell-bead complexes were washed for 11 cycles in 2% MPBS by transferring the complexes from one well to the next well in an automated magnetic bead selection device. After the 2% MPBS washing, two more washing steps were performed with PBS. In the last well of the automated magnetic bead selection device, the cell-beads complexes were resuspended in 1 mL PBS and the titres determined by plating on SDCAA+G agar plates or with synthetic defined medium containing 2% (w/v) glucose containing leucine drop out media plus 2% agar (SD-Leu+G agar plates). For selection by magnetic activated cell sorting (MACS) yeast cells were incubated for one hour at room temperature with 500 streptavidin microbeads (Miltenyi Biotec, Cologne, Germany) in 6 mL PBS+2 mM EDTA. The cell/bead mixture was loaded onto a pre-washed LS column (Miltenyi Biotec, Cologne, Germany) in the presence of a magnet, and the column was washed twice with PBS+2 mM EDTA. After the magnet was removed the bound yeast cells were eluted with 6 mL PBS buffer.

For yeast selections using the capillary washing device (CWD) the yeast cell mixture and 100 µl streptavidin coated paramagnetic beads (Dynal M280) were blocked in 1 mL 2% MPBS for 1 hour. The paramagnetic beads were resuspended in 1 mL of yeast cells suspension and gently rotated for 1 hour at room temperature in an eppendorf tube. After incubation of the yeast cells with the streptavidin coated paramagnetic beads the mixture was introduced into the capillary (1 mL was used to load one capillary in five 200 µL steps) of the CWD. After automated washing and resuspension of the yeast bead mixture, a final wash with PBS was performed and the yeast/beads complex was collected by adjusting the magnet.

Use of the two selectable markers allowed discrimination of the specific yeast (which are able to grow on minus tryptophan selective agar plates) from the none specific yeast cells (which are able to grow on minus leucine selective agar plates). The number of colony forming units (CFUs) for each titre was tallied.

The enrichment factor was calculated as the ratio of specific yeast cells before and after selection divided by the ratio of the non specific yeast before and after selection.

TABLE 1

Model enrichment of Fab displaying yeast cells:
Detection by magnetic bead selection.

| Ratio[a] | Total cells[b] | Enrichment[c] | Recovery (%)[d] |
|---|---|---|---|
| Kingfisher | | | |
| 1/100 | ~$10^7$ | 288,000 | 12.8 |
| 1/1000 | ~$10^8$ | 1,100,000 | 6 |
| 1/10000 | ~$10^9$ | 400,000 | 10.7 |
| Capillary Washing Device (CWD) | | | |
| 1/100 | ~$10^7$ | 76,000 | 4.7 |
| 1/1000 | ~$10^8$ | 41,000 | 6 |
| 1/10000 | ~$10^9$ | 10,000 | 5.3 |
| MACS | | | |
| 1/1000 | $10^7$ | 100 | 12 |

[a]ratio of positive cells, EBY100 pTQ3-F2 to negative yeast cells, EBY100 pUR3867 - PH1
[b]the total number of yeast cells selected
[c]the enrichment factor as the ratio of the number of positive to negative cells before and after selection
[d]The percentage of positive input cells retained after selection As shown in Table 1 specific yeast cells displaying a Fab antibody to streptavidin can be enriched by between 2 and 6 orders of magnitude over non relevant yeast cells by one round of selection in an automated magnetic bead selection device such as Kingfisher, capillary washing device or magnetic activated cell sorting (MACS).

Example 5

Preferential Enrichment of Fab-Displaying Yeast Cells: Detection by Flow Cytometry As an alternative to the magnetic bead detection method of Example 4 above, enrichment of an antigen-specific Fab antibody over an excess of non relevant yeast cells was demonstrated using fluorescence-activated cell sorting (FACS) techniques.

The Fab-displaying yeast cells, EBY100 pTQ3-F2 (with a tryptophan auxotrophic selectable marker), were mixed with the nonspecific yeast cells, EBY100 (pUR3867-PH1) carrying a Leu auxotrophic marker, at ratios of 1:100, 1:1000 and 1:10,000. The yeast cell mixture was incubated with 1 µM streptavidin-FITC (Dako, Carpinteria, Calif.) and allowed to equilibrate for 30 minutes at room temperature.

Three thousand cells were sorted by flow cytometry, and 6.5% of cells were collected with the highest fluorescent signal. Yeast cells before and after selection were plated on SDCAA+G agar plates and SD-Leu+G agar plates and the number of CFUs determined. The enrichment factor was calculated as the ratio of the output ratio divided by the input ratio of EBY100 pTQ3-F2 and EBY100 pUR3867-PH1.

After one round of FACS, EBY100 pTQ3-F2 was enriched over EBY100 pUR3867-PH1 ten-fold (data not shown).

TABLE 2

Enrichment factors determined using FACS.

| Initial purity[a] (%) | Sorted purity[b] (%) | Enrichment factor[c] |
|---|---|---|
| 1.6 | 85 | 52 |
| 0.79 | 29 | 36 |
| 0.02 | 5.2 | 212 |

[a]percentage of positive cells (EBY100pTQ3-F2) to negative cells (EBY100pUR3867-PH1) before selection
[b]percentage of positive cells (EBY100pTQ3-F2) to negative cells (EBY100pUR3867-PH1) after selection
[c]ratio of initial purity to sorted purity Example 6

Batch Transfer of a Phage Display Antibody Library to a Multi-Chain Eukaryotic Display Vector As a demonstration of the utility of the phage display/eukaryotic display transfer system to transfer a phage display peptide library en masse to a multi-chain eukaryotic display vector of the present invention, a phage display Fab library prepared using techniques known in the art was transferred to the multi-chain yeast display vector pTQ3 produced as described in Example 1 above.

To transfer the phage display repertoire into the multi-chain yeast display vector the single excision/insertion transfer process described earlier and illustrated in FIG. 1 was used (see also Example 1).

A 50 mL culture of TYAG (TY, ampicillin 100 µg/mL, glucose 2%) was inoculated with 10 µL of a glycerol stock from one round of selection on streptavidin of a naive Fab library cloned into phage (de Haard, H. et al., 1999). The culture was grown overnight at 37° C. and plasmid DNA was prepared (QIAGEN plasmid purification system, Qiagen, Valencia, Calif.).

The Fab antibody repertoire was digested with ApaLI and NotI and Fab antibody fragments of approximately 1.5 kb were recovered and purified by extraction from a 1.0% TBE ethidium bromide agarose gel (QIAEX gel extraction kit, Qiagen, Valencia, Calif.).

Similarly, the multi-chain yeast display vector pTQ3 was digested with ApaLI and NotI and a fragment of approximately 4.6 kb was purified by extraction from a 1.0% TBE ethidium bromide agarose gel.

Ligation of the Fab antibody inserts recovered from the Fab library into the pTQ3 plasmid digested with ApaLI and NotI was performed at a ratio of 4:1 (insert-vector) using 1 µg Fab fragments and 0.7 µg pTQ3 vector in a 100 µL reaction overnight at 16° C. The ligation mix was purified by phenol, chloroform and isoamyl alcohol (PCI) extractions and subsequently precipitated with 100% ethanol.

The purified ligation mix was transformed into *E. coli* strain TG1 (Netherlands Culture Collection of Bacteria, PC 4028, Utrecht, NL) by electroporation using a BioRad Pulser (BioRad, CA) at 2.5 kV, 25 mF and 200 W. The library was plated on 2xTY agar plates (16 g/L bacto-tryptone, 10 g/L yeast extract, 5 g/L NaCl, 15 g/L bacto-agar) containing ampicillin at 100 µg/mL and 2% w/v glucose (TYAG plates). After overnight growth at 37° C. the repertoire was recovered in 2xTY medium plus ampicillin at 100 µg/mL by flooding the plates, and frozen in aliquots in 15% (w/v) glycerol.

The library contained $5.6 \times 10^6$ independent clones. 15 µL of a library suspension of $5.4 \times 10^{10}$ cells/mL was used to inoculate 100 mL of TYAG, and the culture was grown overnight at 37° C. Plasmid DNA recovered as described above.

The intermediate pTQ3-Fab repertoire was then digested with AscI and with SfiI. A fragment of approximately 6.1 kb was purified as described above. Source vector pTQ3 was similarly digested with AscI and SfiI and a fragment of approximately 1150 bp was purified.

The purified 1150 bp fragment above was ligated with the pTQ3-Fab repertoire digested with AscI and SfiI in a ratio of 6:1 (insert-vector) using 1.6 µg insert and 1 µg vector. The ligation mix was purified and transformed into *E. coli* strain TG1 as described above to give a final pTQ3-Fab library of $1 \times 10^6$ independent clones.

The library was recovered from plates as described above, and 10 mL was inoculated in 50 mL TYAG and grown overnight at 37° C. Plasmid DNA was prepared from pTQ3-Fab library and transformed into yeast strain EBY100 by the method of Gietz, D. et al., (1992) to give a final library size in yeast of $2\times10^6$ independent yeast clones.

Example 7

Selection of Batch Transferred Eukaryotic Display Fab Library: Detection by Magnetic Bead Selection To demonstrate that a yeast display Fab library can undergo selection from a population of yeast cells displaying a diverse repertoire of Fab antibodies, multiple selection experiments were performed using an automated magnetic bead selection device.

The yeast repertoire prepared in Example 6 was grown at 30° C. in SDCAA+G, and antibody expression was induced with galactose (as in Example 4). The pool of yeast cells was incubated for 1 hour with 100 μL streptavidin paramagnetic beads (Dynal M280, Dynal Biotech, Oslo, Norway) in an end volume of one mL 2% MPBS.

After incubation of the yeast-bead mixture, the cell-bead complexes were washed for 11 cycles in 2% MPBS by transferring the complexes from one well to the next well in the automated magnetic bead selection device. After the 2% MPBS washing, two more washing steps were performed with PBS. In the last well of the automated magnetic bead selection device, the cell-bead complexes were resuspended in 1 mL PBS and the yeast colony titres before and after selection were determined by plating on SDCAA+G agar plates. The selected yeast cells were then used to inoculate a fresh culture of 10 mL SDCAA+G and a second round of selection was performed as above.

The percentage of positive and negative clones was determined by yeast whole cell ELISA after the first round of selection and after the second round of selection. Cells were grown and induced in a 96 well plate (Corning Costar, Cambridge, Mass.) in 100 mL SDCAA plus 2% (w/v) galactose.

After induction, cells were washed one cycle with PBS and divided equally onto two plates for detection of antigen binding and heavy chain display. In one plate the cells were resuspended in 100 μL 2% MPBS containing anti-streptavidin-HRP (0.87 μg/mL) for detecting antigen binding. The cells of the second plate were resuspended in 100 μL 2% MPBS containing anti-c-Myc (1 μg/mL) for detecting heavy chain display.

After one hour incubation the cells were washed two cycles with PBS and determination of specific binding occurred by resuspending the cells in 100 μL TMB solution. After color development, the reaction was stopped by adding 50 μL 2N sulfuric acid. Cells were pelleted by centrifugation, and 100 μl of supernatant was transferred to a flexible 96 well plate (Falcon, BD Biosciences, Bedford, Mass.) and the absorbance at 450 nm recorded. For heavy chain detection, 100 μL 2% MPBS containing rabbit anti-mouse-HRP (1:1000) was added to each well. After a one hour incubation, the cells were washed for two cycles and heavy chain display was detected as described above. The results are presented in Table 3.

TABLE 3

Yeast Fab library selection.

| Round | Input | Output | Ratio | % Binders |
|---|---|---|---|---|
| 1 | $4.9 \times 10^9$ | $1.1 \times 10^5$ | $2.7 \times 10^{-5}$ | 20 |
| 2 | $3.0 \times 10^9$ | $3.3 \times 10^5$ | $1.1 \times 10^{-4}$ | 100 |

After one round of selection 20% of the yeast clones screened for antigen binding were found to be positive, after the second round of selection the number of antigen reactive yeast clones was 100%.

Example 8

Figure 7:
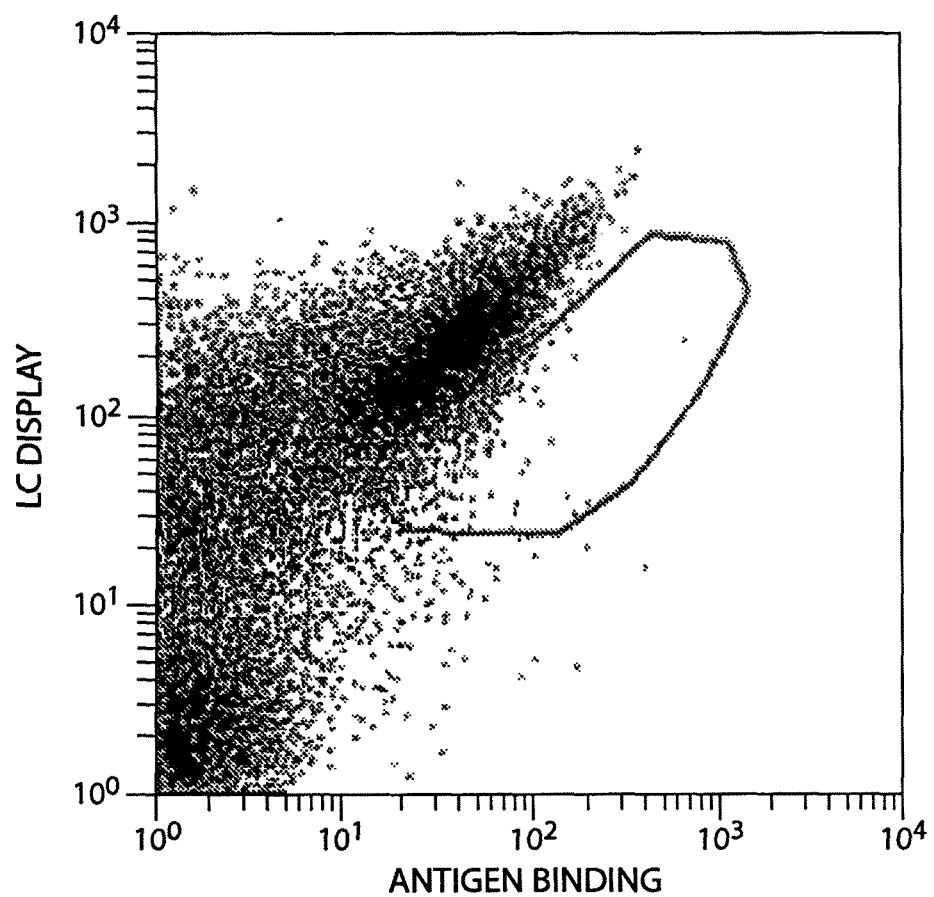
FIG. 7 is a cytometric plot of yeast cell mix. EBY100 pTQ3-F2, EBY100 pTQ3-A12, and EBY100 pTQ3-A12/pESC were double-labeled for both antigen binding and LC display. A plot of LC display against antigen binding and a gating for normalized antigen binding are indicated.

Affinity Selection of Anti-Streptavidin Displaying Yeast Cells: Detection by Flow Cytometry In another affinity discrimination experiment, clones EBY100 pTQ3-F2 and EBY100 pTQ3-A12/pESC contain an empty vector pESC (Stratagene, La Jolla, Calif.) carrying the Leu auxotrophic marker. The anti-streptavidin antibody F2 has an affinity of 54 nM as determined by plasmon resonance (BIAcore) and the anti-streptavidin antibody A12 has an affinity of approximately 500 nM. These two clones were grown overnight and diluted to $OD_{600}$ of 1.0 in SDCAA plus 2% (w/v) galactose and grown for 48 hours at 20° C. The high affinity antibody containing clone (EBY100 pTQ3-F2) and the low affinity antibody containing clone (EBY100 pTQ3-A12/pESC clones were mixed at a ratio of approximately 1:100. Using the different selectable markers present in each clone allowed discrimination of EBY100 pTQ3-A12/pESC (which are able to grow on minus tryptophan, minus leucine selective agar plates) from EBY100 pTQ3-F2 (which can only grow on minus tryptophan selective agar plates). The cell mixture was labeled as previously except with a serial dilution of streptavidin-FITC of 500 nM, 100 nM, 50 nM, 25 nM and 10 nM. Cells were sorted by flow cytometry in an EPIC ALTRA (Beckman Coulter, Fullerton, Calif.) on the basis of both LC display and antigen binding. The sorting rate was set at 2000 cells/sec and the sorting gate was set to collect 1% of the cell population with the highest ratio of FITC to PE 9 typical FACS histogram is shown in FIG. 7). The input and output cells after selection at different antigen concentrations were titrated on selective plates and the number of colonies were tallied to calculate the enrichment factor and percentage recovery of the higher affinity clone (Table 4). These results demonstrate that the higher affinity clone can be preferentially recovered by flow cytometric sorting and that the optimum antigen concentration is between 100 nM and 25 nM for a mixture of two antibodies of $K_d$=54 nM and $K_d$ of approximately 500 nM.

TABLE 4

Affinity discrimination of two yeast displayed Fab antibodies of different affinities.

| Antigen (nM)[a] | Titre (-Trp)[b] | Titre (-Trp/-Leu) Fab A12[c] | Titre (-Trp) -(-Trp/-Leu) Fab-F2[d] | Percentage Fab-F2[e] | Enrichment[f] |
|---|---|---|---|---|---|
| Input | $3.2 \times 10^7$ | $3.7 \times 10^7$ | $4.7 \times 10^5$ | 1.3 | |
| Output | | | | | |
| 500 nM | $9 \times 10^3$ | $8.9 \times 10^3$ | 100 | 1.1 | 0.9 |
| 100 nM | $1.3 \times 10^3$ | $7.9 \times 10^2$ | $5.6 \times 10^2$ | 71 | 56 |
| 50 nM | $2.4 \times 10^3$ | $1.2 \times 10^3$ | $1.2 \times 10^3$ | 102 | 80 |
| 25 nM | $1.2 \times 10^3$ | $9.1 \times 10^2$ | $3.2 \times 10^2$ | 35 | 27 |
| 10 nM | $1.53 \times 10^3$ | $1.49 \times 10^3$ | 45 | 3 | 2.3 |

[a] Antigen concentration used for labelling yeast cells prior to FACS.
[b] Titre on -Trp selective plates.
[c] Titre on -Trp/-Leu selective plates representative of the number of yeast colonies containing antibody construct pTQ3-Al2.
[d] Titre on -Trp plates minus titre on -Trp/-Leu selective plates representative of the number of yeast colonies containing antibody construct pTQ3-F2.
[e] The percentage of yeast cells containing the higher affinity antibody pTQ3-F2
[f] The ratio of positive to negative yeast cells before and after selection.

Example 9

Construction of Yeast-Displayed Libraries Diversified by Error-Prone PCR

To demonstrate the ability to generate novel multi-chain display vector libraries the Fab antibody F2, specific for streptavidin, was subjected to error prone PCR. Separate LC, HC and total Fab antibody were cloned into the yeast display vector. Error-prone PCR was performed in the presence of 2.25 mM $MgCl_2$ and 0.375 mM $MnCl_2$ for 30 cycles. Purified products were cloned into pTQ3 yeast display vectors as a ApaL1/Asc1 fragment, Sfi1/Not1 fragment or ApaL1/Not1 fragment corresponding to the LC, a HC and a whole Fab fragment as in Example 2. The ligation mix was transformed into *E. coli* and grown on selective agar plates containing 100 μg/mL ampicillin to give a LC repertoire of $5\times10^6$ designated pTQ3F2-LC$^{ep}$, a HC repertoire of $5.6\times10^8$ designated pTQ3F2-HC$^{ep}$ and a whole Fab repertoire of pTQ3F2-Fab$^{ep}$. The repertoires were harvested and an inoculated of 200 mL (sufficient to encompass at least 10 times the library diversity) was made. Plasmid DNA was isolated from a 200 mL culture and transformed into the yeast strain EBY100 as described in Example 2. The resulting repertoires were designated EBY100-pTQ3F2-LC$^{ep}$ (size=$5\times10^6$): EBY100-pTQ3F2-HC$^{ep}$ (size=$1.7\times10^6$); EBY100-pTQ3F2-Fab$^{ep}$ (size=$10^6$). The mutation frequency at the nucleotide level was 1.5% for the LC and 0.8% for the HC. The mutation frequency at the amino acid level was 3% for the LC and 1.3% for the HC.

Example 10

Figure 8A:
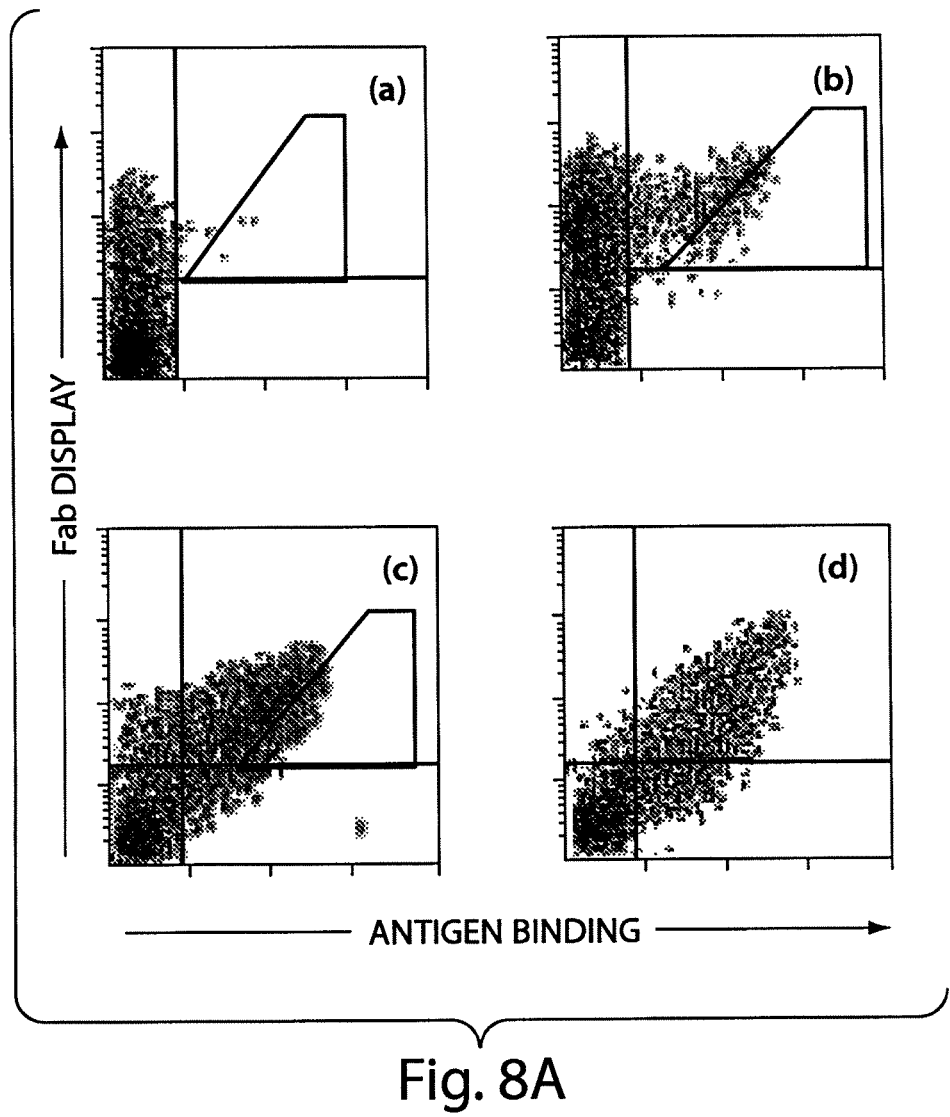
FIGS. 8A-8D are representations of data showing binding to yeast repertoires and individually selected yeast clones at different antigen concentrations.
Figure 8B:
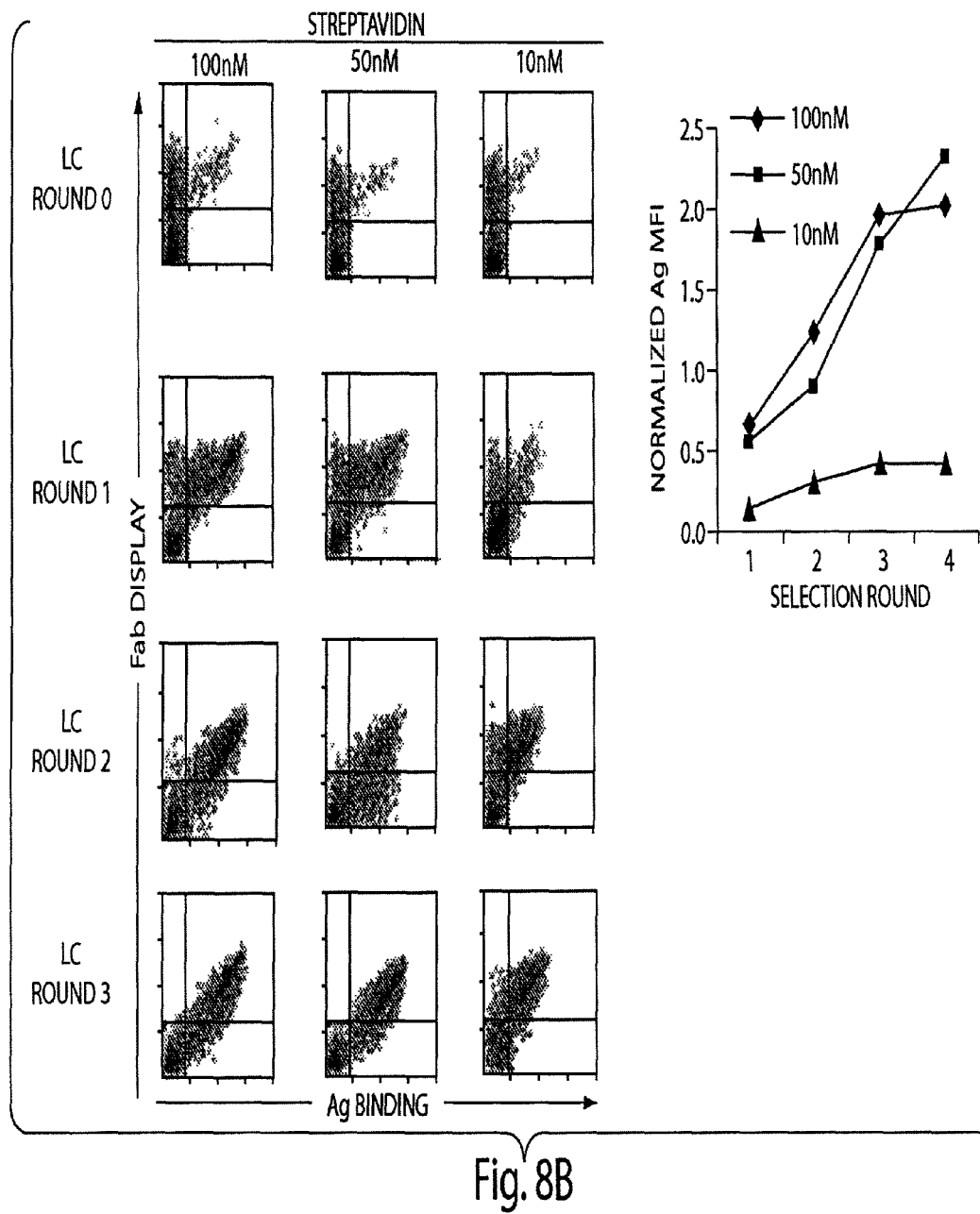
Figure 8C:
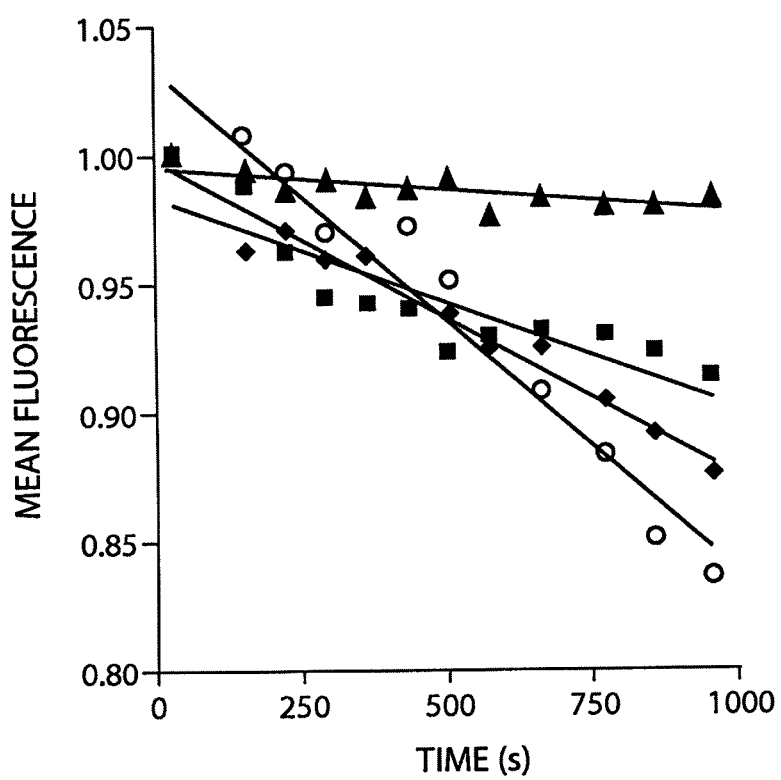

Affinity Selection of Anti-Streptavidin Displaying Yeast Cell Library: Detection by Flow Cytometry To demonstrate affinity selection of a multi-chain yeast display library overnight cultures the libraries EBY100-pTQ3F2-LC$^{ep}$: EBY100-pTQ3F2-HC$^{ep}$ and EBY100-pTQ3F2-Fab$^{ep}$ were prepared as in Example 2 and diluted to $OD_{600}$ of 1.0 in selective media containing SDCAA plus 2% (w/v) galactose and grown for 48 hours at 20° C. The repertoire was labeled with anti-HA mAb (25 μg/mL) for 1 hour at room temperature followed by a second incubation step with rabbit anti-mouse Ig-FITC (1:40 dilution) and 6 nM streptavidin PE for 1 hour at room temperature. Cells were washed once with 0.5 mL PBS following each incubation step and after the final wash cells were kept on ice to prevent antigen dissociation. Samples were sorted in an EPIC ALTRA flow cytometer with a sorting rate of 2000 cells/sec. The first sorting round was done in enrichment mode and the sorting gate was set to collect a population of cells gated on the basis of both LC display and antigen binding. The percentage of cells collected was decreased with successive rounds of selection to account for the decreasing diversity of the repertoire (FIG. 8A). The collected cells were then grown up to an $OD_{600}$ of 1.0 at 30° C. in SDCAA plus (w/v) glucose followed by induction with galactose as in Example 2. Selection was repeated for rounds 2 and 3 which were performed in purity mode with decreasing sorting gates (Table 5). Polyclonal FACS analysis was also performed at different antigen concentrations, and FACS histograms of both LC display and antigen binding activity are shown in FIG. 8B.

TABLE 5

Selection of error-prone repertoires.

| Round | Repertoire | Size | Total Sampled | Ag (nM) | Strategy | FACS mode | % Cells collected | % Ag Binding |
|---|---|---|---|---|---|---|---|---|
| R1 | pTQ3F2LC$^{ep}$ | $5\times10^6$ | $6\times10^6$ | 6 | FACS | Enrichment | 6.0 | 40 |
| R2 | " | " | $4\times10^6$ | 6 | FACS | Purity | 1.4 | 70 |
| R3 | " | " | $4\times10^6$ | 6 | FACS | Purity | 0.2 | 75 |
| R1 | pTQ3F2HC$^{ep}$ | $1.7\times10^6$ | $3\times10^8$ | — | Kingfisher | — | — | 23 |
| R2 | " | " | $2\times10^6$ | 6 | FACS | Purity | 1.4 | 72 |
| R3 | " | " | $4\times10^6$ | 6 | FACS | Purity | 0.5 | 62 |
| R1 | pTQ3F2Fab$^{ep}$ | $10^6$ | $5\times10^6$ | 6 | FACS | Enrichment | 5.0 | 18 |
| R2 | " | " | $4\times10^6$ | 6 | FACS | Purity | 1.4 | 60 |
| R3 | " | " | $5\times10^6$ | 6 | FACS | Purity | 0.2 | 73 |

Example 11

Analysis of Selected Fab Antibodies

The yeast clones retrieved from the affinity selection of the repertoires EBY100-pTQ3F2-LC$^{ep}$; EBY100-pTQ3F2-HC$^{ep}$; EBY100-pTQ3F2-Fab$^{ep}$ were affinity screened to quantitate the improvement in affinity over the starting wild-type antibody. The selected antibodies were also sequenced to determine the mutations that correlate with improved affinity.

Yeast colonies were picked and resuspended in 25 μL of lyticase solution (2.5 mg/mL; Sigma, St. Louis, Mo.) for 1 hour at 37° C. after which 2 μL was taken and used in a PCR reaction. Separate LC and HC were amplified and sequenced using and ABI-PRISM sequencer. Mutations from wild-type were determined using sequence alignment and are shown in Table 6.

TABLE 6

Overview of mutated Fab antibodies selected from error prone repertoires by FACS.

| Repertoire | Round | Clone | Sequence $V_L$ | Sequence $V_H$ | Normalized FACS signal[1] |
|---|---|---|---|---|---|
| wt-F2 | | | | | 1.00 |
| F2 LC$^{ep}$ | R1 | R1C9 | F62I | / | |
| " | R1 | R1H8 | S2P, D85V | / | 1.42 |
| " | R1 | R1H10 | H34R,Y96H | / | 1.15 |
| " | R2 | R2H8 | S2P, D85V | / | 1.23 |
| " | R2 | R2H10 | H34R',Y96H | / | 1.23 |
| " | R2 | R2A7 | no a.a. mut. | / | 0.95 |
| " | R3 | R2H8 | S2P, D85V | / | 1.9 |
| F2 HC$^{ep}$ | R3 | R3H4 | / | H53R | |
| " | | R3D2 | / | H53R; S62A | |
| F2 Fab$^{ep}$ | R2 | R2D3 | H34R | no a.a. mut. | 1.65 |
| " | R2 | R2G4 | V11A, H34N, V58A, S67P, L95I | P40L | 0 |
| " | R3 | R3B1 | Y96F | P40L | 1.78 |
| " | R3 | R3H1 | " | A23V, S65R | 1.50 |
| " | R3 | R3E1 | S2P, D85V | K14E | 1.56 |

TABLE 6-continued

Overview of mutated Fab antibodies selected from error prone repertoires by FACS.

| Repertoire | Round | Clone | Sequence $V_L$ | Sequence $V_H$ | Normalized FACS signal[1] |
|---|---|---|---|---|---|
| " | R3 | R3G4 | " | H53R, A84T | 1.70 |
| " | R3 | R3F1 | Q1L, K45R, L95V | no a.a. mut. | 1.60 |
| " | R3 | R3A3 | H34R | no a.a. mut. | 1.65 |
| " | R3 | R3H3 | H34R, Q79R | Q3R | 1.62 |

Mutations underlined are positioned in the CDR loops of the antibody
Ratio of mean fluorescence intensity Ag binding/mean fluorescence intensity LC display of test clone to wild-type starting antibody The off rate of the selected Fabs was determined by measuring the dissociation rate in FACS as the decrease in fluorescence signal over time; the clone, R2H10 gave the greatest improvement in affinity (10.7 fold, 3.2 nM). This dissociation rate was fit to a exponential decay model and the $k_d$ calculated. Yeast cells were labeled with both anti-HA to detect the LC and also for antigen with streptavidin PE. Yeast cultures were grown an induced as described Example 2 and approximately $2 \times 10^7$ cells were collected and washed with PBS. The cells were then incubated with 100 μL anti-HA Mab (20 μg/mL) for 1 hour and then washed with 0.5 mL of PBS. The cells were then incubated with rabbit anti-mouse FITC (1:40) and streptavidin PE (1:40 dilution of 1 μg/mL stock) for 1 hour on ice. The cell pellet was then resuspended in an excess of non-fluorescent ligand at room temperature. The concentration of non-fluorescent label was taken so that it was 10-100 fold in excess of the molar concentration of yeast displayed Fab antibody assuming there are approximately 100,000 copies of a Fab antibody per yeast cell. The decrease in fluorescence intensity was monitored for 1.5 mins. to 30 mins. by flow cytometry. Unlabeled yeast cells were used to set the background fluorescence. The $k_d$ was then calculated by fitting the dissociation rate to a model of exponential decay from which the $k_d$ was calculated. FIG. 10c shows the off rate determination by FACS for clones wild-type F2, and mutants R2E10, R3B1 and R3H3.

The affinity of soluble Fabs was determined by subcloning the selected Fab antibodies into the *E. coli* expression vector pCES1 as in Example 2. Soluble Fabs were purified and affinity tested via BIAcore (de Haard, H. et al.). The affinity of selected Fabs is shown in Table 7.

Example 12

Figure 8D:
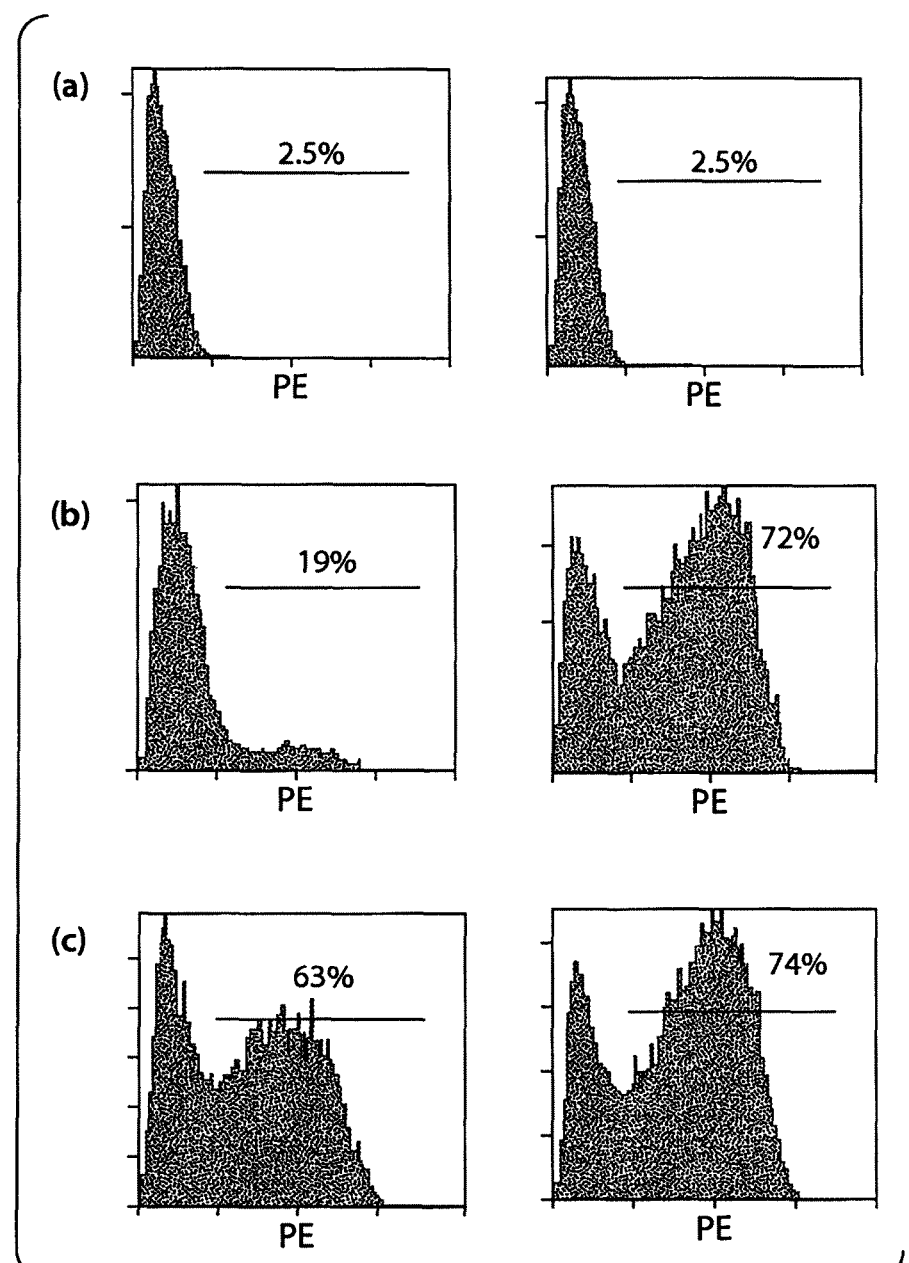

Rapid Selection of Yeast Displayed Fab Repertoire Using a Combination of Kingfisher and FACS Selection In order to speed up the affinity selection of yeast displayed repertoires and also to develop methodologies which allow for the selection of larger repertoires in excess of $10^8$, a combination of both Kingfisher as the first round of selection (as in Example 4) and FACS for the latter rounds of selection (as in Example 5) was used. The LC repertoire constructed in Example 9 was grown overnight and antibody expression was induced as in Example 2. The yeast cell population was incubated with streptavidin coated magnetic particles and selected with Kingfisher as in Example 4. In parallel, the same repertoire was selected by FACS as in Example 5. The pool of yeast cells from the round 1 selection campaigns using Kingfisher and FACS was grown overnight and antibody expression induced as in Example 5. Yeast cells were labeled as in Example 2 and selected by FACS as the second round. Analysis of the selected pools of yeast displaying Fabs was performed using polyclonal FACS (see Example 10). The percentage of antigen binding cells can be seen to increase faster when Kingfisher is used as the first round of selection in preference to FACS (FIG. 8d).

Example 13

Construction of an Ig Heavy Chain Eukaryotic Display Vector: pTQ5-HC

As a demonstration of an alternate embodiment of the multi-chain eukaryotic display vector of the present invention (specifically a multi-chain eukaryotic display vector wherein the chains of the multi-chain are encoded on separate vectors, thus forming separate components of a vector set), a yeast display vector effective in a host yeast cell transformed with the vector of expressing, transporting, and displaying an Ig heavy chain fragment was constructed as one vector of a matched vector set.

An HC fragment display vector was constructed by further altering the vector pTQ3 produced according to Example 1. Display vector TQ3 was digested with BseRI, thus identifying a designed restriction site of the vector positioned in each of the two tandem GAL1 promoters (see Example 1, SEQ ID

TABLE 7

Characterization of affinity improved Fab fragments.

| | | | | FACS[c] | Biacore[c] | | | |
|---|---|---|---|---|---|---|---|---|
| Clone | Library | Mutations Variable LC[a,b] | Mutations Variable HC[a,b] | $k_d$ ($10^{-4}$ s$^{-1}$) | $k_d$ ($10^{-3}$ s$^{-1}$) | $k_a$ ($10^4$ M$^{-1}$s) | $k_D$ nM | factor |
| wt-F2 | / | none | none | 2.2 ± 1.0 | 1.52 ± 0.15 | 4.51 ± 0.01 | 34 | / |
| R2H10 | LC e.p. | H34R, Y96H | none | 0.5 ± 0.1 | 0.18 ± 0.01 | 5.69 ± 0.02 | 3.2 | 10.7 |
| R3A9 | " | S2P, D85V | none | 1.3 ± 0.1 | 1.53 ± 0.57 | 7.84 ± 0.08 | 19.5 | 1.7 |
| R3H4 | HC e.p. | none | H53R | 1.9 ± 0.7 | N.D. | N.D. | N.D. | N.D. |
| R3D2 | " | none | H53R, S62A | 1.6 ± 0.6 | N.D. | N.D. | N.D. | N.D. |
| R2D3 | fab e.p. | H34R | 1 silent mut. | 2.1 ± 0.3 | 1.04 ± 0.10 | 5.76 ± 0.08 | 18.1 | 1.9 |
| R3H1 | " | Y96F | A23V, S65R | 1.0 ± 0.4 | 0.28 ± 0.04 | 3.25 ± 1.14 | 8.7 | 3.9 |
| R3G4 | " | S2P, D85V | H53R, A84T | 3.5 ± 1.1 | 2.37 ± 0.25 | 10.9 ± 1.13 | 21.7 | 1.6 |
| R3B1 | " | Y96F | P40L | 0.9 ± 0.2 | 0.22 ± 0.05 | 4.00 ± 1.30 | 5.5 | 6.3 |
| R3E1 | " | S2P, D85V | K14E | 2.1 ± 1.2 | 1.03 ± 0.10 | 7.64 ± 0.95 | 13.5 | 2.5 |
| R3H3 | " | Q79R | Q3R | 2.0 ± 1.0 | 1.04 ± 0.04 | 11.3 ± 2.64 | 9.2 | 3.7 |

[a]antibody residue numbering according to Kabat et al.
[b]underlined mutation are in the CDR loops
[c]Reported values are the means of three independent experiments NO: 5 designated bases 990-995). A 942 bp fragment, which spans one of the cloning sites of the multi-chain display vector (FIG. 3), was removed and the remaining 4,868 bp vector backbone was gel purified using techniques known in the art (specifically via GFX PCR and Gel Band Purification Kit, Amersham-Pharmacia, Piscataway, N.J.). The vector backbone was re-ligated and transformed into *E. coli*. The resultant vector, designated "pTQ5", was verified using by restriction analysis.

Figure 9:
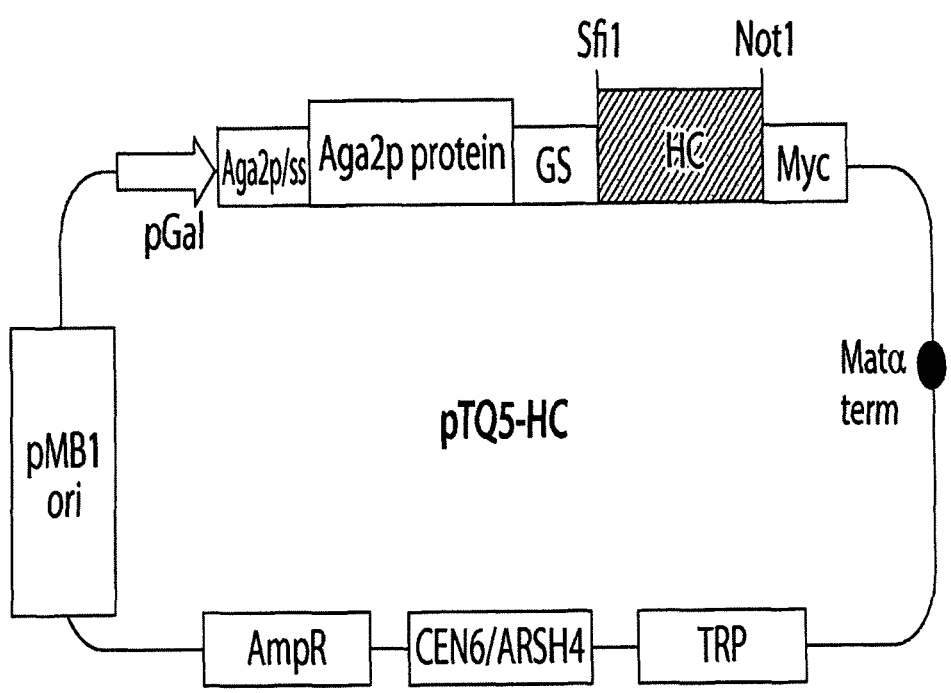
FIG. 9 is a schematic diagram of the heavy chain yeast display vector, pTQ5-HC, according to the invention, having a heavy chain fragment insert under the control of an inducible GAL1 promoter. The Ig heavy chain fragment is positioned as a SfiI/NotI insert fragment, and is expressed as a cell surface bound fusion protein using the Aga2p signal sequence (Aga2p/ss) and anchoring protein subunit (Aga2p protein). The heavy chain fragment (HC) is fused to a myc epitope tag. Other elements necessary for plasmid replication (i.e., pMB1-ori and Cen6/ARSH4), yeast mating (i.e., Matα terminator) and useful as selective markers (i.e., ampR and TRP) are also indicated.

The HC for the anti-streptavidin Fab antibody F2 was restriction digested from pTQ3-F2 as a 709 bp SfiI/NotI fragment, purified, and cloned into SfiI/NotI digested vector pTQ5. The resultant HC display vector was designated "pTQ5-HC" (FIG. 9).

Later modifications were made to this vector by inserting a 6×His tag for purification of soluble Fab antibodies and by repositioning the stop codon (TAA) at the end of the myc tag, before the PacI site, to eliminate superfluous amino acids. Other modifications have included the removal of an endogenous XbaI restriction site within the Trp selective marker by site directed mutagenesis. This was done to facilitate cloning and manipulation of lead antibodies from the CJ library set (Dyax Corporation, Cambridge, Mass.).

Example 14

Eukaryotic Host Cell Expression of an Ig Heavy Chain Eukaryotic Display Vector: HC Expression in a Haploid Yeast Cell To demonstrate the utility of independent vectors of a multi-chain eukaryotic display vector set, a yeast display vector (of a vector set) encoding an Ig heavy chain fragment was inserted into a eukaryotic host cell, and the transformed host cell grown under conditions suitable for expression of the heavy chain component of an Ig Fab.

The yeast strain EBY100 (InVitrogen, Carlsbad, Calif.) was transformed with vector pTQ5-HC (of Example 13), and separately with pTQ5 as a control, following transformation procedures previously described. The successful transformants, designated EBY100 pTQ5-HC and EBY100 pTQ5 respectively, were cultured overnight at 30° C. in 10 mL SDCAA+G.

The next day cultures were centrifuged and the pelleted yeast cells were resuspended in 10 mL SDCAA plus 2% (w/v) galactose to an $OD_{600}$ of 1. Cell cultures were then grown for 24 hours at 20° C. to induce expression of the Aga2p heavy chain fusion product. Cells were centrifuged and washed twice in 1 mL sterile water and transferred to an eppendorf tube.

Cell pellets were resuspended in 200 mL of SDS-PAGE sample buffer plus DTT, and glass beads (425-600 micron) were applied to just below the meniscus. The cell and bead suspension was vortexed 4 times for 1 minute keeping the suspension on ice between vortexing. The supernatant was transferred to a fresh tube and heated to 100° C. for 5 minutes.

Figure 10:
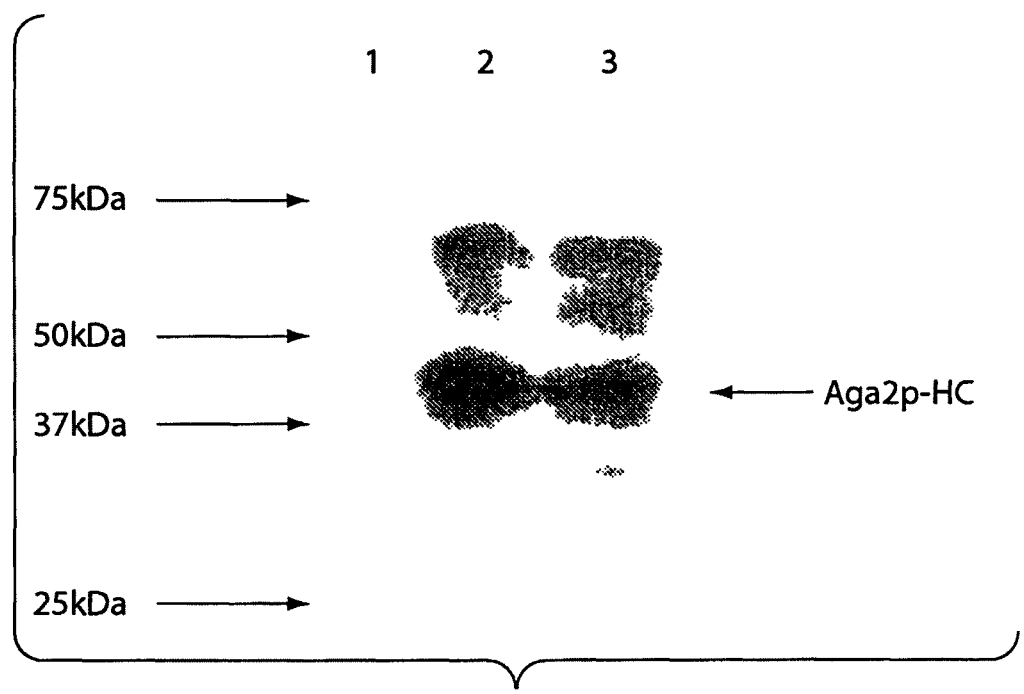
FIG. 10 is a representation of a western blot demonstrating expression of the 45 kD Aga2p-HC fusion product as detected with an anti c-Myc antibody in the haploid parent yeast cell EBY100 pTQ5-HC (lane 2) compared to the (control) empty vector yeast host cell EBY100 pTQ5 (lane 1) and the (standard) Fab display vector yeast host cell EBY100 pTQF2 (lane 3).

Protein samples were separated on a SDS-PAGE gel and transferred to a nitrocellulose membrane for western blotting. Detection of the Aga2p-HC fusion polypeptide was performed using an anti-c-Myc monoclonal antibody conjugated to HRP (1 μg/mL, Roche Molecular Biochemicals, Indianapolis, Ind.). Immunodetection was by enhanced chemilluminescence (Amersham-Pharmacia, Piscataway, N.J.). The 45 kD Aga2p-HC fusion polypeptide approximately was detected. No detectable Aga2p-HC fusion product was detected in the (empty) control vector clone EBY100 pTQ5 (FIG. 10).

Example 15

Eukaryotic Host Cell Display of an Ig Heavy Chain Eukaryotic Display Vector: HC Display on the Surface of a Haploid Yeast Cell To demonstrate the ability of a vector from a multi-chain eukaryotic display vector set to display the anchored chain of a multi-chain polypeptide on the surface of a haploid eukaryotic cell, a yeast display vector (of a vector set) encoding an Ig heavy chain fragment was inserted into a eukaryotic host cell, and the transformed host cell was grown under conditions suitable for expression and display of the heavy chain component of an Ig Fab.

EBY100 pTQ5-HC (from Example 14) was grown, and antibody expression was induced as above. HC expression was induced by 48 hours of growth with shaking at 20° C. Yeast samples were centrifuged and the cell pellet resuspended in PBS containing 1 mg/mL BSA. Two of the samples were again centrifuged and the cell pellets separately resuspended in either 100 μL of anti-human $C_H1$ (25 μg/mL; Zymed, San Francisco, Calif.) followed by incubation for 1 hour at room temperature. The cells were pelleted and washed once with 0.5 mL of PBS/1% (w/v) BSA. Cell samples were then incubated with rabbit anti-mouse FITC (1:50 dilution; Dako, Carpinteria, Calif.) for 1 hour in the dark.

To detect antigen binding, cells were labeled with streptavidin-FITC (1:25 dilution; Dako, Carpinteria, Calif.) in PBS/ 1% (w/v) BSA and incubated in the dark at room temperature for 1 hour. All samples were centrifuged and the cell pellets washed once with 0.5 mL PBS and then resuspended in 500 mL of PBS.

Figure 11:
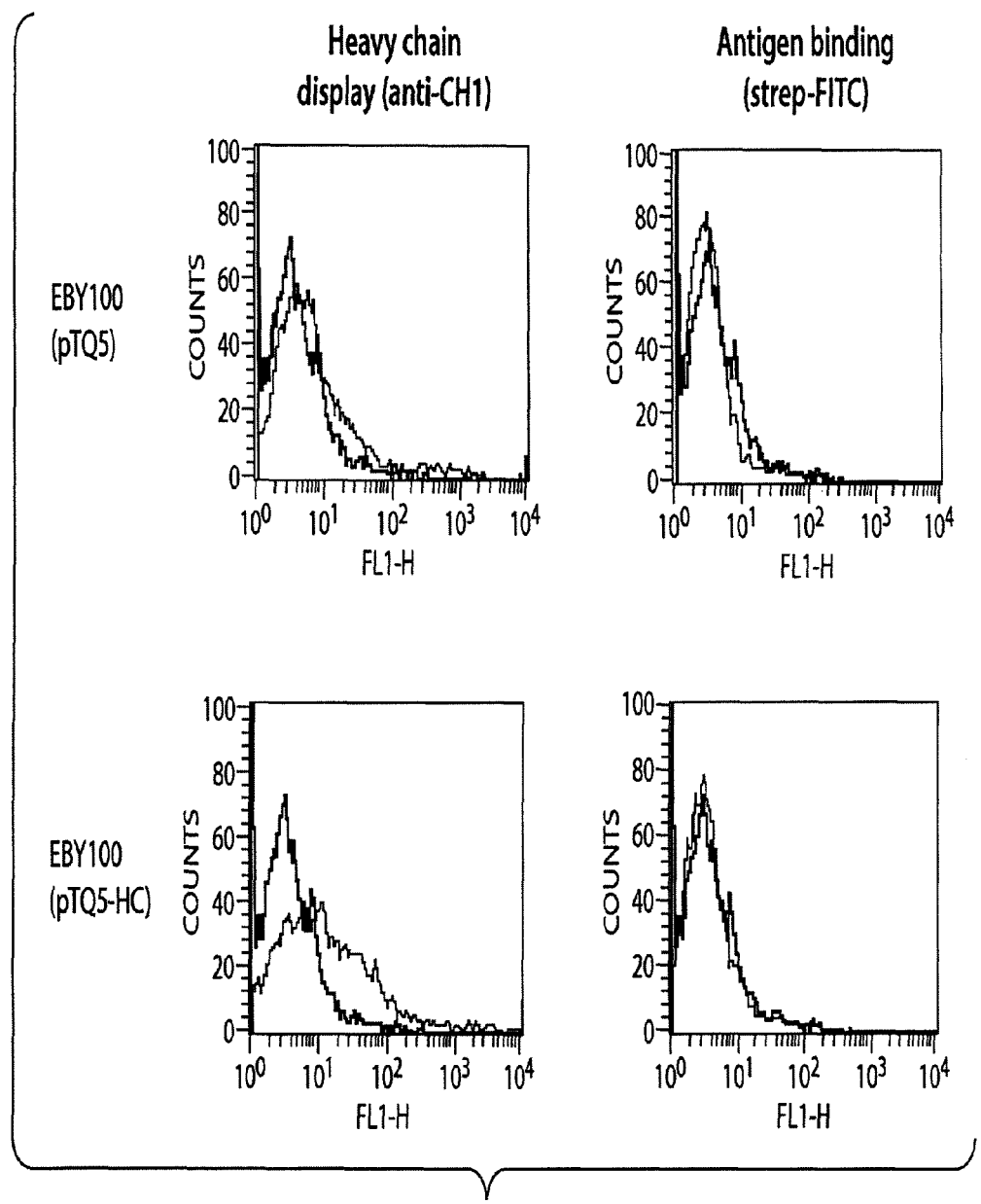
FIG. 11 is a series of cytometric plots showing HC display on the surface of yeast cells without the presence of a light chain at time equal to zero (i.e., background; solid black lines) and 48 hours after induction (dotted lines). Yeast cells EBY100 pTQ5-HC, and control yeast cells EBY100 pTQ5, were labeled with anti-$C_H1$ and rabbit anti-mouse IgG FITC to detect the presence of the HC, and also with streptavidin FITC (strep-FITC) to detect antigen binding activity on the yeast surface. HC only can be seen displayed on the yeast cell surface but does not have any antigen binding activity in the absence of a paired LC.

The presence of cell surface bound HC-antigen binding was detected by flow cytometry. Cells prior to induction showed no display of heavy chain or functional streptavidin binding. After induction of HC expression, yeast cells could be detected displaying heavy chain only but no functional streptavidin binding could be detected as expected (FIG. 11).

Example 16

Construction of an Ig Light Chain Eukaryotic Display Vector: pTQ6-LC

A light chain yeast display vector was constructed to provide a multi-chain eukaryotic display vector set, i.e., when used in conjunction with the heavy chain yeast display vector described above (see Example 13, supra).

Figure 12:
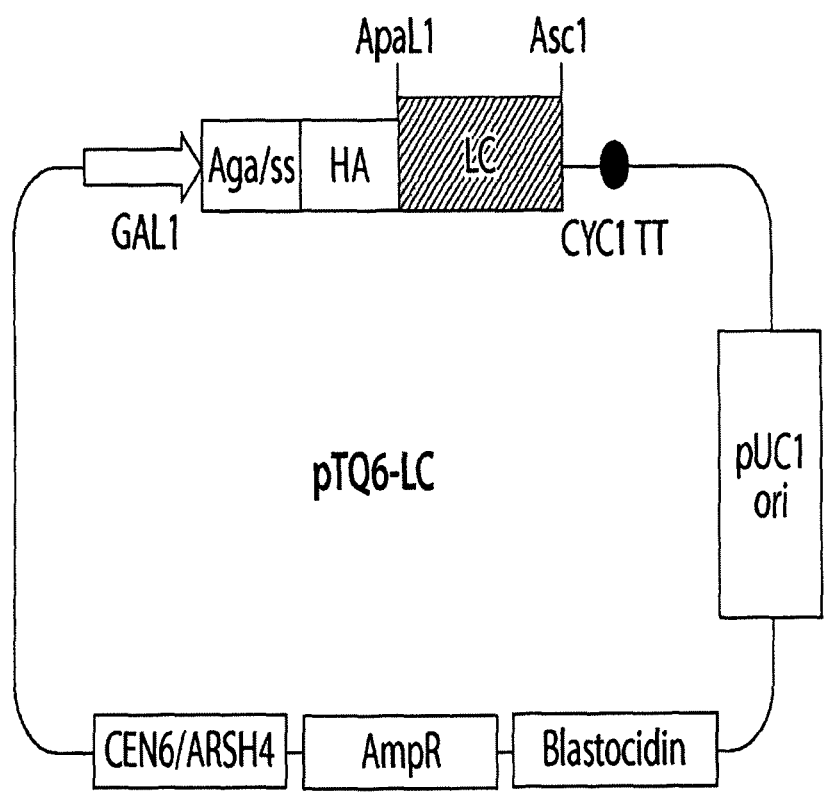
FIG. 12 is a schematic diagram of the light chain yeast expression vector, pTQ6-LC, according to the invention, having a light chain insert under the control of an inducible GAL1 promoter. The Ig light chain is positioned as an ApaLI/AscI insert fragment, is expressed as a soluble protein using the Aga2p/ss. The light chain fragment (LC) is also fused with a HA epitope tag. Other elements useful for plasmid replication (e.g., pUC1-ori and Cen6/ARSH4) and useful as selection markers (i.e., ampR and Blastocidin®) are also indicated.

A LC yeast expression vector was constructed by amplifying a fragment containing the anti-streptavidin LC fused to the HA epitope tag and Aga2p signal sequence. The amplification product was gel purified using a GFX PCR and Gel Band Purification Kit (Amersham-Pharmacia, Piscataway, N.J.), and digested with HindIII and PmeI. The 783 bp LC fragment was purified on a 1.2% TAE-agarose gel together with the 4,323 bp vector backbone of a HindIII/PmeI-digested pYC6/CT vector (InVitrogen, Carlsbad, Calif.). The LC fragment and pYC6/CT vector were ligated together and the ligation mix was transformed into *E. coli* strain TG1. The resultant LC expression vector was designated "pTQ6-LC" (FIG. 12).

Example 17

Eukaryotic Host Cell Expression of an Ig Light Chain Eukaryotic Display Vector Soluble LC Expression in a Haploid Yeast Cell To demonstrate the utility of independent vectors of a multi-chain eukaryotic display vector set, a yeast display vector (of a vector set) encoding an Ig light chain fragment was inserted into a eukaryotic host cell, and the transformed host cell grown under conditions suitable for expression of a soluble light chain component of an Ig Fab.

Yeast strain W303-1B (a/alpha ura3-1/ura3-1 leu2-3,112/leu2-3,112 trp1-1/trp1-1 his3-11,15/his3-11,15 ade2-1/ade2-1 can1-100/can1-100), obtained from P. Slonimski, was transformed with pTQ6-LC (of Example 16) and separately pYC6/CT as a control, following transformation procedures previously described. The successful transformants, designated W303 pTQ6-LC and W303 pYC6/CT respectively, were cultured overnight at 30° C. in 10 mL SD-G plus 300 µg/mL Blasticidin® (SD-G+Bls).

The next day cultures were centrifuged and the pelleted yeast cells resuspended in 10 mL SD+Bls plus 2% (w/v) galactose to an $OD_{600}$ of 0.4. Cell cultures were then grown for 24 hours at 20° C. to induce expression of the soluble light chain polypeptide. Cells were centrifuged and the supernatants were concentrated ten fold using a centrifugal filter unit (CENTRICON YM-10; Millipore, Bedford, Mass.).

Cell pellets were washed and resuspended in breaking buffer (50 mM sodium phosphate, pH 7.4, 1 mM EDTA, 5% (w/v) glycerol plus protease inhibitor cocktail; Roche Molecular Biochemicals, Indianapolis, Ind.) to an $OD_{600}$ of 50, and glass beads (425-600 micron) were applied to just below the meniscus. The cell and bead suspension was vortexed 4 times for 1 minute keeping the suspension on ice between vortexing. The supernatant was transferred to a fresh tube and an aliquot was heated to 100° C. for 5 minutes in SDS-PAGE sample buffer plus DTT.

Figure 13:
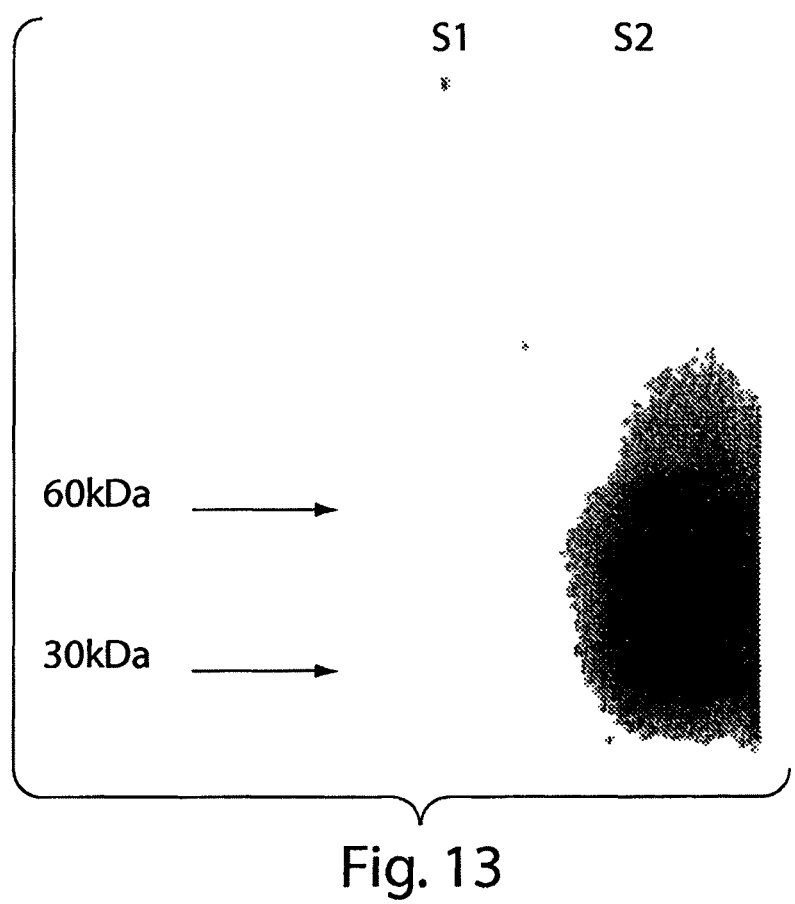
FIG. 13 is a representation of a western blot demonstrating expression of the 60 kD light chain polypeptide as detected in the culture supernatant with an anti-HA antibody in the haploid parent yeast cell W303 pTQ6-LC (lane S2) compared to the (control) empty vector yeast host cell W303 pYC6 (lane S1).

Protein samples were separated on a SDS-PAGE gel and transferred to a nitrocellulose membrane for western blotting. Detection of the LC polypeptide was performed using an anti HA monoclonal antibody (1 µg/mL) in combination with a rabbit anti-mouse conjugated to HRP (1/1000). Immunodetection was by enhanced chemiluminescence (Amersham-Pharmacia, Piscataway, N.J.). Polypeptide products of 30 kD and 60 kD were detected in the culture supernatant. No detectable LC product could be detected in the empty vector control W303 pYC6/CT (FIG. 13).

Example 18

Surface Display of a Multi-Chain Polypeptide on a Eukaryotic Host Cell: The Product of Cellular Fusion of a Haploid Host Cell Pair To demonstrate the operability of the novel process for displaying a biologically active multi-chain polypeptide on the surface of a diploid eukaryotic cell via the cellular fusion of two haploid eukaryotic cells, each possessing a different vector from a matched multi-chain eukaryotic display vector set, haploid yeast cells containing a vector expressing a soluble Ig light chain fragment were mated to haploid yeast cells containing a vector expressing and displaying an Ig heavy chain-anchor fusion polypeptide to produce a diploid yeast cell that displays a functional Fab polypeptide on the surface of the host cell.

Yeast clones W303 pTQ6-LC (from Example 17) and EBY100 pTQ5-HC (from Example 14) were grown on agar plates supplemented with either Blastocidin® (InVitrogen, Carlsbad, Calif.; 300 µg/mL; SD+G+Bls agar plates) or tryptophan drop out medium (SD-Trp+G agar plates). These plates were then replica plated onto double selective plates containing synthetic defined medium for tryptophan dropout plus 300 µg/mL Blasticidin® (SD-Trp+G+Bls). The resulting cell layer of diploid yeast cells was streaked to single colonies. Seven Trp+/Bls$^R$ colonies were selected and grown overnight with shaking at 30° C. in 100 mL SD+G-Trp+Bls in 96-wells plate.

The next day, the culture was centrifuged and the pelleted yeast cells were resuspended in either 10 mL SD-Trp+Bls plus 2% (w/v) galactose or 10 mL YP medium+Bls plus 2% (w/v) galactose for 24 hours at 20° C. Cells were washed in PBS and divided equally onto three 96 well plates. Cells of the first plate were resuspended in 100 µL streptavidin-HRP (0.87 µg/mL), cells of the second plate were resuspended in 100 µL anti-c-Myc-HRP (1 µg/mL), and cells of the third plate were resuspended in 100 µL anti-HA (1 µg/mL) and additionally labeled with a rabbit anti-mouse-HRP (1/1000).

Figure 14:
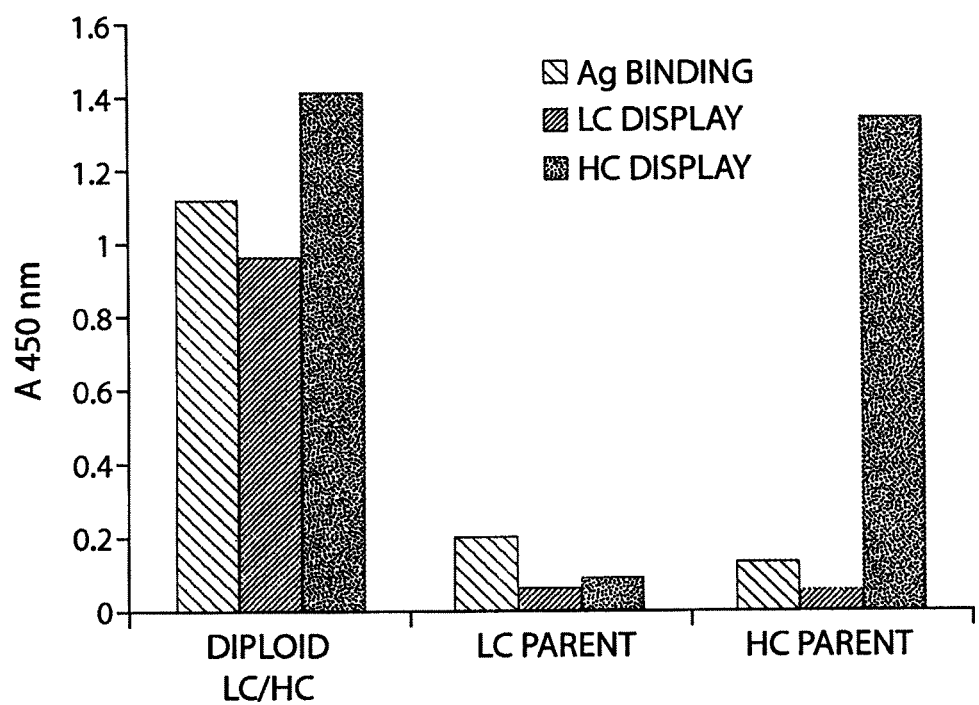
FIG. 14 is a histogram plot illustrating whole cell ELISA determination of streptavidin binding activity on the cell surface of parent haploid yeast cells (W303 pTQ6-LC and EBY100 pTQ5-HC) compared to the derived diploid yeast cell (DIPLOID LC/HC) and control empty vector yeast host cell W303 pYC6 and standard Fab display vector yeast host cell EBY100 pTQ3-F2.
Figure 15:
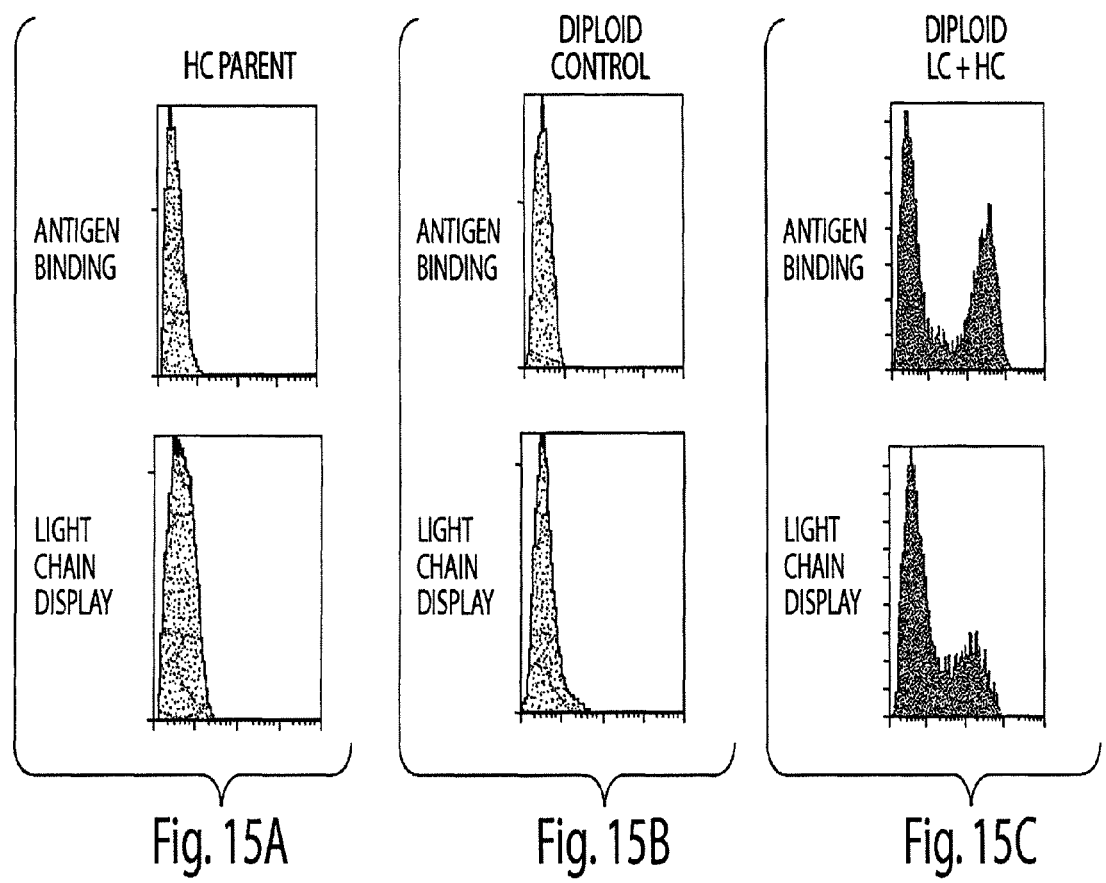
FIGS. 15A-15C are a series of FACS histograms showing antigen binding and light chain display on an anti streptavidin haploid HC parent (A) and a diploid control containing empty LC and HC expression plasmids (B) and a positive diploid expressing a streptavidin specific Fab on its surface (C).

Yeast whole cell ELISA was performed (as in Example 7) and FACS (as in Example 15) was performed to detect antigen binding and HC display. All diploids tested bound to streptavidin and displayed light chains in whole cell ELISA (FIG. 14) and FACS (FIGS. 15A-C). Specifically, streptavidin binding activity was detected on diploid yeast cells displaying combinatorially assembled Fab antibody (Diploid LC/HC) on their surface whereas haploid parents expressing either LC only (W303 pTQ6-LC) or HC only (EBY100 pTQ5-HC) showed no binding activity. Standard haploid yeast cells displaying a Fab antibody (EBY100 pTQ3-F2) showed streptavidin binding activity. Also (as expected) the haploid parent yeast cell expressing only LC (W303 pTQ6-LC) showed no HC display, while standard haploid yeast cells displaying a Fab antibody (EBY100 pTQ3-F2) showed HC display.

Five yeast clones were selected for overnight culture at 30° C. in 10 mL SD+G-Trp+Bls with shaking. The next day, cell cultures were centrifuged and the pelleted yeast cells resuspended in 10 mL SD-Trp+Bls plus 2% (w/v) galactose to an $OD_{600}$ of 0.4 for 24 hours to induce vector expression. An alternative protocol involves resuspension in 10 mL of YP media plus Blastocidin® plus 2% (w/v) galactose.

After the 24 hour induction incubation, one aliquot from each of the five diploid yeast cultures was pelleted, washed, and resuspended in breaking buffer to an $OD_{600}$ of 50. Glass beads (425-600 micron) were added to just below the meniscus, and the cell-bead suspension vortexed 4 times for 1 minute keeping the suspension on ice between vortexing. The supernatant was transferred to a fresh tube and an aliquot was heated to 100° C. for 5 minutes in SDS-PAGE sample buffer plus DTT.

Figure 16:
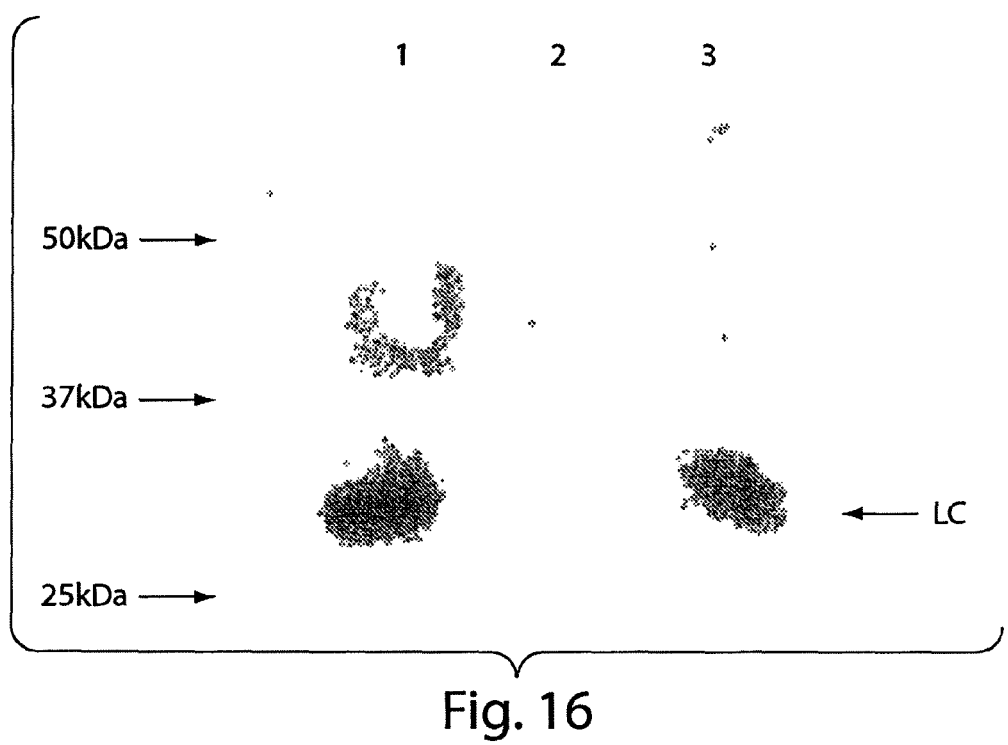
FIG. 16 is a representation of a western blot demonstrating expression of the 30 kD LC polypeptide as detected with an anti-HA antibody in the diploid yeast cell formed by mating EBY100 pTQ5-HC with W303 pTQ6-LC (lane 3) compared to the (control) diploid yeast cell formed by mating EBY100 pTQ5 with W303 pYC6 (lane 2), and the parent LC vector yeast host cell W303 pTQ6-LC (lane 1).
Figure 17:
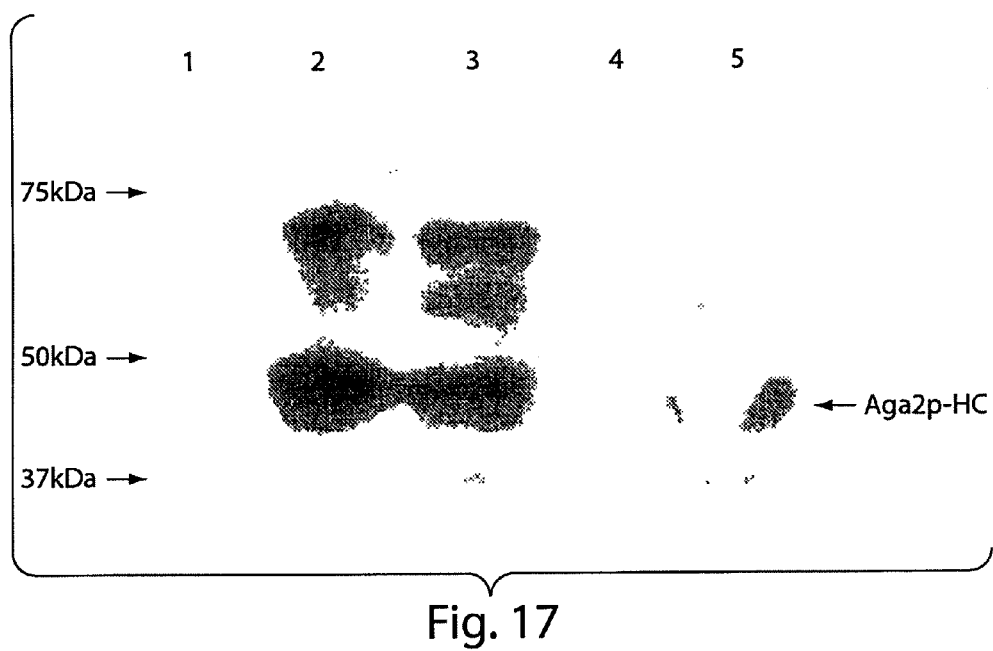
FIG. 17 is an illustration of a western blot demonstrating expression of the 45 kD Aga2p-HC fusion product as detected with an anti c-Myc antibody in the diploid yeast cell formed by mating EBY100 pTQ5-HC with W303 pTQ6-LC (lane 5) compared to the (control) diploid yeast cell formed by mating EBY100 pTQ5 with W303 pYC6 (lane 4), the parent HC vector yeast host cell EBY100 pTQ5-HC (lane 3), the standard Fab display vector yeast host cell EBY100 pTQ3F2 (lane 2), and the (control) empty vector yeast host cell EBY100 pTQ5 (lane 1).

Protein samples were separated on SDS-PAGE gels and transferred to a nitrocellulose membrane for western blotting. Detection of the light chain polypeptide was performed using an anti-HA antibody (1 µg/mL) in combination with a rabbit anti-mouse conjugated to HRP on one membrane. Detection of the heavy chain-Aga2p fusion polypeptide was performed using an anti-c-Myc antibody directly conjugated to HRP (1 µg/mL, Roche Molecular Biochemicals, Indianapolis, Ind.). Immunodetection was by enhanced chemiluminescence (Amersham-Pharmacia, Piscataway, N.J.). The LC product of approximately 30 kD and the HC-Aga2p fusion product of approximately 45 kD were both detected in the diploid yeast lysate (FIGS. 16 and 17). No detectable LC or HC-Aga2p fusion product was detected in control diploid clones harboring the two empty vectors pTQ5 and pYC6/CT.

Also after the 24 hour induction incubation, a second aliquot from each of the five diploid yeast cultures was analyzed by flow cytometry. $5 \times 10^6$ cells per detection agent were washed one cycle with PBS and the cells were resuspended in 100 μL PBS containing anti-c-Myc (25 μg/mL) for heavy chain detection, 100 μL PBS containing anti-streptavidin-FITC (1:40) for detection of antigen binding and 100 μL PBS containing anti-HA (25 μg/mL) for light chain detection. Cells were incubated for one hour in the dark and than washed again one cycle with PBS. After washing the cells were resuspended in 100 μL PBS containing rabbit anti mouse-FITC (1:40) and again incubated for one hour in the dark.

Cells with anti-streptavidin-FITC were processed during the second incubation step because of the one step labeling. After incubation, cells were washed for one more cycle and resuspended in 500 μl PBS and analyzed by flow cytometry. All five samples were shown to bind to the antigen and to display the HC as well as the LC (FIGS. 15A-C).

Figures 18A, 18B, 18C:
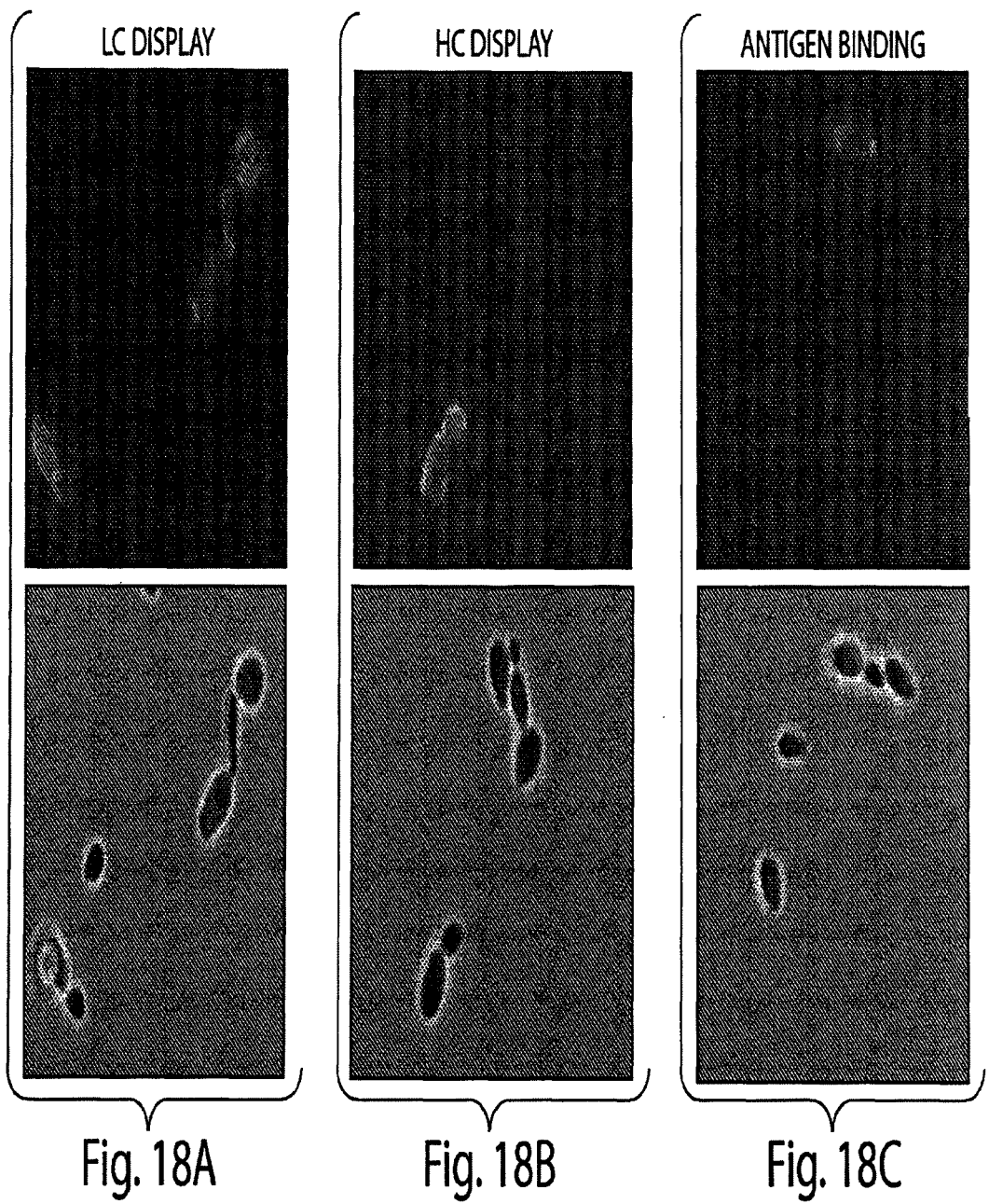
FIGS. 18A-18C are representations of immunofluorescence detection of combinatorially assembled Fab antibodies on the surface of yeast diploid cells (A) LC display (B) HC display (C) Antigen binding. The top row shows immunofluorescence and the bottom row shows phase contrast.

After the 24 hour (induction) incubation, a third aliquot from one of the five diploid yeast cultures was also labeled for immunofluorescence. $10^8$ cells were resuspended in 100 μL of either streptavidin-FITC (30 μg/mL, Dako) or of a mixture of rabbit anti-human lambda chain (1:40; Dako, Carpinteria, Calif.) and monoclonal anti-$C_H1$ (25 μg/mL, Zymed, San Francisco, USA). A first sample was further incubated with rabbit anti-FITC (1:40; Dako, Carpinteria, Calif.), and finally with swine anti-rabbit conjugated to FITC (1:20; Dako, Carpinteria, Calif.). A second sample was submitted to a double labeling with swine anti-rabbit conjugated to FITC (1:20; Dako, Carpinteria, Calif.) for the light chain and rabbit anti-mouse conjugated to Tetramethylrhodamine isothiocyanate (TRITC, 1:30, Sigma, St. Louis, Mo.) for the heavy chain (FIGS. 18A-C).

The diploid displayed the light and the heavy chain at the cell surface and was shown to bind streptavidin, as expected. The haploid parent expressing HC only was stained only by the TRITC labeling of the heavy chain. The haploid parent LC was negative in all the cases.

Example 19

Mating Efficiency of a Haploid Host Yeast Cell Pair

To demonstrate the efficiency of cell fusion of two haploid yeast cells, each possessing a different vector from a matched multi-chain eukaryotic display vector set as a viable process to generate a diploid yeast cell displaying a biologically active multi-chain polypeptide on its surface, mating efficiency was determined for a host yeast cell pair according to the present invention. Quantitative determination of the efficiency of the mating reaction was assessed as follows.

Each haploid parent EBY100 pTQ5 (from Example 14) and W303 pYC6/CT (from Example 17) was grown overnight at 30° C. in the appropriate selective medium SD+G-Trp and SD+G+Bls respectively. $3 \times 10^7$ cells from the two fresh haploid cultures were mixed and collected on a 45 mm nitrocellulose filter (microfill device of Millipore, Bedford, Mass.). The filter was incubated for 4 hours at 30° C. on a non selective rich medium plate (YPD). Cells were then resuspended in YPD medium and titrated on the two parental selective media and on the double selective medium (which only allows the growth of the diploids) SD+G-Trp+Bls. Spontaneous reversion or resistance was assessed by processing each haploid parent separately in the same way and plating them on the double selective medium without dilution.

The mating efficiency of the haploid parent EBY100 pTQ5 was calculated as follows: (the number of diploids growing on SD+G-Trp+Bls minus the number of spontaneous resistant EBY100 pTQ5 growing on SD+G-Trp+Bls) divided by (the total number of cells from the mating reaction showing growth on SD+G-Trp).

The mating efficiency of haploid parent W303 (pYC6) the efficiency was calculated as follows: (the number of diploids on SD+G-Trp+Bls minus the number haploid cells W303pYC6/CT growing on SD+G-Trp+Bls) divided by (the number of cells on SD+G+Bls).

$3 \times 10^7$ haploid cells of each mating type produced $1.5 \times 10^7$ diploid cells containing both pTQ5 and pYC6 yeast expression vectors. Mating efficiency results revealed that 51% of haploid parents containing the pTQ5 plasmid formed diploids, and that 64% of haploid parents containing the pYC6 plasmid formed diploids.

Example 20

Preferential Enrichment of Diploid Yeast Cells Displaying a Combinatorially Assembled Fab Antibody: Detection by Flow Cytometry To confirm the ability to select yeast cells displaying an antigen specific Fab antibody over an excess of non-relevant yeast cells, fluorescent activated cell sorting (FACS) was used. A positive diploid yeast cell displaying a combinatorially assembled Fab antibody specific for streptavidin was used. The diploid yeast cell carried the phenotypic markers of $Trp^+/Leu^-/Bls^R$, and was able to grow on minus tryptophan and Blastocidin® containing selective agar plates. This diploid was designated the $Bls^R$ diploid. A non-relevant yeast diploid cell carrying the phenotypic markers $Trp^+/Leu^+$ was used, and was able to grow on minus leucine and tryptophan containing selective agar plates. This diploid was designated the Lee diploid. Both positive (Ble) and non-relevant ($Leu^+$) diploid yeast cells were grown overnight in media of SD plus 2% (w/v) glucose under selective conditions of −Ttp/+Leu/+Bls media and −Trp/−Leu media respectively. Yeast cultures were induced in YP media containing galactose at 2% (w/v). After determining the $OD_{600}$ of the yeast culture and using the conversion factor of $OD_{600}$ of 1 is equivalent to $4 \times 10^6$ cells/mL, a mix of positive to non-relevant yeast cells was prepared in an approximate ratio of 1:10000. For selection by FACS the yeast cell mixture was labeled with 500 nM streptavidin PE and selected as in Example 8. For Kingfisher, the yeast cell mixture was incubated with streptavidin coated beads and selected as in Example 4. For selection by MACS, induced diploids were incubated for one hour at room temperature with 500 μL streptavidin microbeads (Miltenyi Biotec, Cologne, Germany) in 6 mL PBS+2 mM EDTA. The cell/bead mixture was loaded onto a pre-washed LS column (Miltenyi Biotec, Cologne, Germany) in the presence of a magnet and the column was again washed twice with PBS+2 mM EDTA. After the removal of the magnet, the cells retained on the column were eluted in 6 mL PBS buffer.

Yeast cells were recovered and titrated on selective agar plates for either the $Bla^R$ phenotype or the $Leu^+$ phenotype. The ratio of $Bls^R/Leu^+$ colonies before and after selection was used to calculate the enrichment factor and the percentage recovery of positive yeast cells

TABLE 8

Single pass enrichment experiments using MACS, Kingfisher and FACS.

| Device | Input | | | Output | | | Recovery | Enrich. |
|---|---|---|---|---|---|---|---|---|
| | Leu$^+$ diploid | Bla$^R$ diploid | Bla$^R$/Leu$^+$ (%) | Leu$^+$ diploid | Bla$^R$ diploid | Bla$^R$/Leu$^+$ (%) | | |
| MACS | $5 \times 10^8$ | $4 \times 10^4$ | 0.008 | $3 \times 10^5$ | $10^4$ | 3.6 | 25% | 465 |
| Kingfisher | $6 \times 10^8$ | $4 \times 10^4$ | 0.0065 | 600 | 750 | 125 | 1.8% | 19230 |
| FACS | $2 \times 10^7$ | $10^4$ | 0.05 | 204 | 6 | 3.4 | ND | 68 |

In the given example of an antibody specific for streptavidin, Kingfisher was seen to give a higher enrichment factor than MACS. However, the percentage recovery of positive yeast cells was significantly lower. Using FACS, an enrichment factor of one order of magnitude was observed from one round of selection for an anti-streptavidin Fab antibody.

Example 21

LC and HC Recombination by Cellular Fusion of a Haploid Host Cell Pair and Affinity Selection: Detection by Flow Cytometry To exemplify the utility of the fusion of two haploid eukaryotic cells, each possessing a different vector from a matched multi-chain eukaryotic display vector set, a haploid yeast cell population containing a vector expressing a plurality soluble Ig light chain fragment variants (i.e., a library of LC variants) is mated to a haploid yeast cell population of opposite mating type containing a vector expressing and displaying a plurality of Ig heavy chain-anchor fusion polypeptide variants (i.e., a library of HC variants) to produce a novel diploid yeast cell population that displays a plurality of functional Fab polypeptides on the surface of the host cells (i.e., a novel Fab library).

Fab phage display isolates, pre-selected for a target molecule from a Fab repertoire, are used to provide the source heavy chain and light chain components for a batch transfer of the phage display isolate genetic information to a multi-chain yeast display vector set (as demonstrated in Example 6), using the multi-chain yeast display vector set (as described in Examples 14 and 17) to provide novel recombination of light and heavy chain isolates via host cell fusion of two haploid eukaryotic cells, each possessing a different vector from a matched multi-chain eukaryotic display vector set (as demonstrated in Example 18).

A phage display antibody library (de Haard, H. et al., 1999) was subjected to one round of selection on streptavidin coated magnetic particles using protocols familiar to those skilled in the art. This repertoire was used as a starting repertoire for transfer into the yeast display system. The input of the library was $5 \times 10^{12}$ phage particles and the output after one round of selection was $3.75 \times 10^5$ phage particles.

The HC fragments were isolated from the round 1 selected phage display library as SfiI/NotI fragments and cloned into the Ig heavy chain yeast display vector pTQ5, which was digested with SfiI and NotI (Example 13). The ligation mix was transformed into E. coli to give a library of $10^8$. This library was then transformed into the yeast strain EBY100 to give a library of $4 \times 10^7$ and designated EBY100-pTQ5-HC$^{rep}$.

The LC fragments were isolated from the round 1 selected phage display library as ApaL1/AscI fragments and cloned into the Ig light chain yeast display vector, pTQ6 digested with ApaL1 and AscI (Example 16). The ligation mix was transformed into E. coli to give a library of $1 \times 10^8$. This library was then transformed into the yeast strain BJ5457 to give a library of $8 \times 10^7$ and was designated BJ5457-pTQ6-LC$^{rep}$.

Both the HC and LC repertoires in yeast contained sufficient diversity to cover the starting repertoire of $3.75 \times 10^5$ in phage. DNA fingerprint analysis of individual clones showed diverse restriction patterns indicating that different germline segments were represented in the separate LC and HC libraries.

In the first mating regime $7.25 \times 10^8$ cells of the LC repertoire (BJ5457-pTQ6-LC$^{rep}$) were mated $3.4 \times 10^8$ cells of EBY100-pTQ5-F2HC containing the single HC specific for streptavidin and derived from clone F2. The mating conditions were under selective pressure to maintain both the LC and HC expression plasmids (tryptophan auxotrophy and blastocidin resistance). A library of $1.9 \times 10^8$ diploids was obtained with a mating efficiency of 55%. Analysis of individual clones from this library by yeast whole cell ELISA showed 100% of clones displayed a HC and 100% of clones displayed a LC.

In a second mating regime $3.6 \times 10^8$ cells of the HC repertoire (EBY100-pTQ5-HC$^{rep}$) were mated with $3 \times 10^8$ cells of BJ5457-pTQ6-F2LC containing a single LC specific for streptavidin and derived from clone F2. The mating conditions were under selective pressure to maintain both the LC and HC expression plasmids (tryptophan auxotrophy and blastocidin resistance). A library of $8 \times 10^7$ diploids was obtained with a mating efficiency of 27%. Analysis of individual clones from this library by yeast whole cell ELISA showed 89% of clones displayed a HC and all of these clones displayed a LC.

In a third mating regime $2.0 \times 10^{10}$ cells of the HC repertoire (EBY100-pTQ5-HC$^{rep}$) were mated with $5.6 \times 10^9$ cells of the LC repertoire (BJ5457-pTQ6-LC$^{rep}$). The mating conditions were under selective pressure to maintain both the LC and HC expression plasmids (tryptophan auxotrophy and Blastocidin® resistance). A diploid library of $4 \times 10^9$ was obtained with a mating efficiency of 68%. Analysis of individual clones from this library by yeast whole cell ELISA showed 94% of clones displayed a HC and 53% of clones displayed a LC.

This series of mating experiments shows that large libraries can be made using the mating of separate repertoires of LC and HC. These repertoires comprise diverse V gene germline segments and can be expressed and displayed on the yeast cell surface. These repertoires were selected with the antigen streptavidin using Kingfisher (see Example 7). After two rounds of selection, 97% of clones retrieved showed antigen binding activity in a yeast whole cell ELISA (see Example 7).

Example 22

Construction of LC and HC Repertoires Diversified by Error Prone PCR

To demonstrate the fusion of two repertoires of haploid yeast cells, each possessing a different vector from a matched multi-chain vector set, can be used for affinity maturation, a HC repertoire diversified by error prone PCR (Example 9) in pTQ5 (Example 13) and a separate LC repertoire diversified by error prone PCR (Example 9) in pTQ6 (Example 16) were constructed in yeast haploid cells of opposite mating type.

The HC repertoire was constructed by amplifying the anti-streptavidin F2 antibody under error prone conditions (Example 9). The amplified fragment was digested with SfiI and NotI, purified and cloned into the HC-only expression vector pTQ5 (Example 13), which had also been digested with SfiI and NotI. The resulting ligation mix was transformed into *E. coli* to give a library of $7 \times 10^7$. This library was transformed into the yeast strain EBY100 to give a library of $9 \times 10^6$ and was designated EBY100 pTQ5-HC*.

The LC repertoire was constructed by amplifying the LC of the anti-streptavidin F2 antibody under error prone conditions (Example 9). The amplified fragment was digested with ApaL1 and AscI and cloned into the LC only expression vector (Example 16), which had also been digested with ApaL1 and AscI. The resulting ligation mix was transformed into *E. coli* to give a library of $4 \times 10^7$, and this was subsequently transferred into the yeast strain BJ5457 to give a library of $1.8 \times 10^7$ (designated BJ5457 pTQ6-LC*).

The resulting mutation frequency at the nucleotide level was 0.8% for the HC repertoire and 1.5% for the LC repertoire. These frequencies correspond to 1.3% and 3% mutation frequency at the amino acid level, respectively. The haploid cell repertoires EBY100 pTQ5-HC* and the BJ5457 pTQ6-LC* were inoculated with 10 μL and 30 μL of glycerol stock respectively so that at least 10 copies of each independent clone was represented and grown up overnight in selective media (Example 18). Approximately $1.6 \times 10^{10}$ haploid cells corresponding to BJ5457 pTQ6-LC* and $3 \times 10^{10}$ haploid cells corresponding to EBY100 pTQ5-HC* were mated (Example 19) to give a diploid repertoire of $5 \times 10^9$ when grown on selective media (designated EBY100 pTQ5-HC*/BJ5457 pTQ6-LC*). Ten clones were picked and tested by yeast colony PCR (Example 11) for the presence of LC and HC containing vectors, and all gave the expected LC and HC product. To determine the fraction of the diploid repertoire EBY100 pTQ5-HC*/BJ5457 pTQ6-LC* that displayed a HC product and also showed binding to the antigen streptavidin, a yeast whole cell ELISA was performed (Example 7). 68% (15/22) diploids tested displayed a HC, and 18% (4/22) of diploid clones tested showed binding to streptavidin.

In order to highlight the versatility of the procedure, similar hierarchical mating experiments were performed where either the wild-type HC or the wild-type LC was kept constant while varying only the corresponding opposite chain. Using the anti-streptavidin F2 Fab as the model antibody, a diploid repertoire was made from mating EBY100-pTQ5-F2HC and BJ5457 pTQ6-LC*. This diploid repertoire has a constant HC and variable LC. The mating resulted in 100% of diploids displaying a HC and 30% showing antigen binding by yeast whole cell ELISA. Similarly, a diploid repertoire was made by mating BJ5457 pTQ6-F2LC with EBY100 pTQ5-HC*. This diploid repertoire has a constant LC and a variable HC. This mating resulted in 70% of diploids displaying a HC and 45% showing antigen binding activity by yeast whole cell ELISA.

Example 23

Affinity Selection of a Combinatorially Assembled Fab Repertoire

To demonstrate that a repertoire of yeast cells displaying a plurality of combinatorially assembled Fab antibodies diversified by error prone PCR can be affinity selected, a combination of selection by Kingfisher and affinity driven flow cytometric sorting was used to recover the optimum affinity clones.

An overnight culture of the diploid repertoire EBY100 pTQ5-HC*/BJ5457 pTQ6-LC* (Example 22) was prepared (Example 18). The culture was induced as in Example 18 and a total of $10^{10}$ cells were subjected to one round of Kingfisher selection (Example 7). The antigen binding yeast diploid cells were retrieved and subjected to FACS affinity driven selection (see Example 20). The percentage of antigen binding clones increased during selection as determined by yeast whole cell ELISA (Example 7). The percentage of antigen binding clone also increased, and the antigen mean fluorescent intensity as determined by FACS increased during selection (Table 9).

TABLE 9

Selection of mated LC/HC error prone repertoire by combination of Kingfisher and FACS.

| Round | Ag Conc | Input cells | Output cells | % cells gated | % binding ELISA | % Ag binding FACS | Ag MFI |
|---|---|---|---|---|---|---|---|
| R0 | — | — | — | — | 18% | 2.5% | 1.46 |
| R1 | beads | $10^{10}$ | $5 \times 10^6$ | na | 85% | 35% | 2.99 |
| R2 | 6 nM | $10^7$ | $10^5$ | 1.3% | 68% | 32.2% | 7.62 |
| R3 | 2 nM | $10^6$ | 7,500 | 0.7% | ND | ND | ND |

The progress of the selection campaign was monitored using polyclonal FACS analysis where an overnight culture of the selected repertoires from each round of selection was prepared and antibody expression was induced as in Example 18. Yeast cells were labeled as in Example 20 and analyzed by FACS for both LC display (FITC label) and antigen binding (PE label).

Selected clones were sequenced and the mutations in the variable LC and variable HC are shown in Table 10. The affinity of selected Fabs was determined using FACS by either an off rate screening assay (Example 10) or by a non-linear least squares analysis (data not shown).

TABLE 10

Analysis of Fab antibodies selected from combinatorial library generated by yeast mating.

| Clone | LC Mutations | HC Mutations | FACS $k_d$ e-4s-1 | Factor increase | FACS $K_d$ (nM) | Factor increase |
|---|---|---|---|---|---|---|
| wt-F2 | — | — | 2.4 | 1 | 48 | 1 |
| R2-12 | wt | S19F | 3 | 0.8 | 29 | 1.6 |
| R2-11 | T5A; H34R | Q3R; Q77L | 1 | 2.4 | 23 | 2.1 |
| R3-6 | wt | N32K; I69V; Q101V | 2.1 | 1.1 | 14 | 3.4 |

TABLE 10-continued

Analysis of Fab antibodies selected from combinatorial library generated by yeast mating.

| Clone | LC Mutations | HC Mutations | FACS $k_d$ e-4s-1 | Factor increase | FACS $K_d$ (nM) | Factor increase |
|---|---|---|---|---|---|---|
| R3-9 | wt | H53R; Q3R; G31R | 1.1 | 2.2 | 20 | 2.4 |
| R3-1 | wt | G8S; S54R; T68S | — | — | — | — |
| R3-4 | T24S; H34R | wt | — | — | — | — |
| R3-2 | H34R; L95H; Q79H | wt | 1.6 | 1.5 | 35 | 1.4 |
| R3-7 | H34R; D32Y; P59S; T69S; A74T | A23D | 0.7 | 3.4 | 17 | 2.8 |
| R3-8 | S27G; T76A | H53R | — | — | — | — |

Example 24

Reshuffling of Selected Pools of LC and HC

To demonstrate the versatility of the procedure and the ability to do recursive cycles of selection and reshuffling, pools of selected LC and HC from the output of the third round of selection (Example 23) of the combinatorial EBY100 pTQ5-HC*/BJ5457 pTQ6-LC* repertoire were reshuffled.

Plasmid DNA was prepared using a lyticase treatment (Example 11), and the DNA extract containing both pTQ5-HC*$^{sel}$ and pTQ6-LC*$^{sel}$ expression plasmids containing selected LC and HC was transformed directly into fresh EBY100 and BJ5457 cells, respectively. The transformation mix was grown on selective plates so only BJ5457-pTQ6-LC*$^{sel}$ colonies (selective agar plates containing blastocidin) or EBY100 pTQ5-HC*$^{sel}$ (selective agar plates minus tryptophan) could grow. The BJ5457 pTQ6-LC*$^{sel}$ transformation gave 250 colonies and the EBY100 pTQ5-HC*$^{sel}$ transformation gave 25 colonies. These two mini-repertoires were harvested and grown overnight and mated as in Example 18. This mating reaction gave a diploid repertoire of EBY100 pTQ5-HC*$^{sel}$/BJ5457 pTQ6-LC*$^{sel}$ that covered the theoretical combinatorial diversity of 6250 different LC/HC combinations. Fab antibody expression was induced in the diploid culture and was selected using AutoMACS. This represented the fourth round of selection. Diploid culture from the fourth round of selection was retrieved. Antibody expression was induced, followed by labeling with streptavidin PE at 0.5 nM and selection using FACS (Example 20).

TABLE 11

Analysis of Fab antibodies.

| Clone | LC Mutations | HC Mutations | FACS $k_d$ e-4s-1 | Factor increase | FACS $K_d$ (nM) | Factor increase |
|---|---|---|---|---|---|---|
| wt-F2 | — | — | 2.4 | 1 | 48 | 1 |
| R5-1 | H34R; D32Y; P59S; T69S A74T | N32K; I69V; Q101V | 0.8 | 2.9 | 4.2 | 11.5 |
| R5-12 | H34R; D32Y; P59S; T69S A74T | S19F | 1 | 2.4 | 11.5 | 4.2 |

Example 25

Construction of a Naïve HC Repertoire Yeast Display Vector and Haploid Host Cell To produce a novel heavy chain eukaryotic display vector useful as one component of a multi-chain eukaryotic vector set, a naïve repertoire of HC is cloned into the vector pTQ5 (Example 13).

Antibody HC fragments are isolated from a V gene peripheral blood lymphocyte source and isolated by antibody PCR methods known in the art. The HC library is captured in a phage display vector following techniques known in the art and then transferred to pTQ5 as a SfiI/NotI fragment and transformed into E. coli, producing a library of approximately $1 \times 10^8$. The library is then transformed into yeast strain EBY100, producing library EBY100 pTQ5-HC*$^{rep}$ of approximately $1 \times 10^7$.

Example 26

Construction of a Naïve LC Repertoire Yeast Display Vector and Haploid Host Cell To produce a novel light chain eukaryotic display vector useful as one component of a multi-chain eukaryotic vector set, a naïve repertoire of LC is cloned into the vector pTQ6 (Example 16).

Antibody LC fragments are isolated from a V gene peripheral blood lymphocyte source and isolated by antibody PCR methods known in the art. The LC library is captured in a phage display vector following techniques known in the art and then transferred to pTQ6 as a ApaLI/AscI fragment and transformed into E. coli, producing a library of approximately $1 \times 10^8$. The library is then transformed into yeast strain W303, producing library W303 pTQ6-LC*rep of approximately $1 \times 10^7$.

Example 27

A LC/HC Recombination Library Via Cellular Fusion of a Haploid Host Cell Pair and Subsequent Affinity Selection: Detection by Flow Cytometry To produce a novel Fab (diploid) yeast display library two (haploid) host cell populations; one population containing a repertoire of light chain fragments and the second population containing a repertoire of heavy chain fragments, are co-cultured under conditions sufficient to permit cellular fusion and the resulting diploid population grown under conditions sufficient to permit expression and display of the recombined Fab (LC/HC) library.

Approximately $10^{10}$ EBY100 pTQ5-HC*$^{rep}$ yeast cells (from Example 26) are mated with approximately $10^{10}$ W303 pTQ6-LC*$^{rep}$ yeast cells (from Example 22) following the procedures outlined in Example 18. Ten percent mating efficiency results in an approximately $10^9$ diploid repertoire (thus capturing approximately $10^9$ LC/HC combinations of the possible maximum $10^{14}$ combinatorial LC/HC diversity, given the starting diversity of the individual component LC and HC repertoires in the haploid parents). The diploid repertoire is cultured and expression of LC and HC induced (Example 15). The diploid repertoire is cultured and expression of LC and HC induced (see Example 15). The diploid culture is incubated with streptavidin-FITC and affinity selected using flow cytometric sorting (see Example 8). Affinity variants are screened by off rate determination using flow cytometry (see Example 9) and additionally by surface plasmon resonance techniques known in the art, using soluble Fab antibodies.

Example 28

Production of a Multi-Chain Display Host Cell Pair Library: LC and HC Haploid Yeast Cell Repertoires Via Diploid Sporulation As one example of a novel host cell pair library, wherein one cell population expresses a plurality of variants of one chain of a biologically active multi-chain polypeptide linked to an anchor protein; and the second cell expresses a plurality of variants of a soluble second chain of the multi-chain polypeptide, diploid Fab-displaying yeast isolates resulting from the streptavidin selection screen as described in Example 23 are induced to sporulate by culturing the isolates under conditions of nitrogen starvation (as described in Guthrie and Fink, 1991). Sporulated diploids are harvested, treated with zymolase, sonicated, and plated out on rich plates.

Haploid colonies are separated into two subsamples; one subsample is grown under conditions to facilitate loss of the LC expression vector but selected for the HC display vector, the second subsample is grown under conditions to facilitate loss of the BC display vector but selected for the LC expression vector (for 2µ derived plasmids under non selective conditions, plasmid loss is between 2-6% per generation). After several generations each yeast subculture is effectively purged of non-selected chain expressing vector and contains only the selected (LC or HC) expression vector, thus producing two biased (i.e., pre-selected) single chain expression haploid yeast cells, designated "HAPLOID pTQ6-LC*$^{sel}$" and "HAPLOID pTQ5-HC*$^{sel}$". From these two haploid yeast populations, each containing either the light chain of pre-selected Fabs or the heavy chain of pre-selected Fabs, three mating regimes are established as follows:

In the first mating regime, $10^9$ yeast HAPLOID pTQ6-LC*$^{sel}$ are mated back with $10^9$ yeast EBY100 pTQ5-HC*$^{rep}$ (from Example 21), and grown under selective conditions for maintenance of both LC and HC yeast expression plasmids. Ten percent mating efficiency results in approximately $10^8$ diploids. The diploid repertoire is cultured and expression of LC and HC induced (Example 18). The resulting diploid culture represents a biased repertoire containing unique combinations of the original HC repertoire against the preselected LC repertoire, which can be further screened by, e.g., flow cytometric sorting (Examples 8 and 11) and/or surface plasmon resonance techniques known in the art, using soluble Fab antibodies.

In the second mating regime, $10^9$ yeast HAPLOID pTQ6-HC*$^{sel}$ are mated back with $10^9$ yeast W303 pTQ6-LC*$^{rep}$ (Example 22), and grown under selective conditions for maintenance of both LC and HC yeast expression plasmids. Ten percent mating efficiency results in approximately $10^8$ diploids. The diploid repertoire is cultured and expression of LC and HC induced (Example 18). The resulting diploid culture represents a biased repertoire containing unique combinations of the original LC repertoire against the preselected HC repertoire, which can be further screened by, e.g., flow cytometric sorting (Examples 8 and 11) and/or surface plasmon resonance techniques known in the art, using soluble Fab antibodies.

Finally, in the third mating regime, $10^9$ yeast HAPLOID pTQ6-LC*$^{sel}$ are mated with $10^9$ yeast HAPLOID pTQ6-HC*$^{sel}$, and grown under selective conditions for maintenance of both LC and HC yeast expression plasmids. Ten percent mating efficiency results in approximately $10^8$ diploids. The diploid repertoire is cultured and expression of LC and HC induced (sec Example 18). The resulting diploid culture represents a biased recombination repertoire containing unique combinations of the preselected LC repertoire against the preselected HC repertoire, which can be further screened by, e.g., flow cytometric sorting (Examples 8 and 11) and/or surface plasmon resonance techniques known in the art, using soluble Fab antibodies.

Example 29

Affinity Maturation by Restriction Based Diversification of a Fab Antibody

To demonstrate the utility of restriction-based diversification and shuffling of a Fab antibody for affinity maturation using yeast display and selection, a Fab antibody library is prepared from a lead target specific Fab where either the whole LC or a fragment of the HC is diversified using restriction-based cloning. In one preferred method, an antibody library constructed with restriction sites both bracketing the antibody V gene sequence and also internal to the V gene sequence is used to prepare a plurality of antibody gene fragments for cloning and thus leading to the diversification of the lead antibody.

Lead antibodies isolated from one such antibody library (e.g., the CJ library set, Dyax Corp., Cambridge, Mass.) can be affinity matured by this approach. Antibodies comprising, for example, the CJ phagemid library have a LC bracketed by a unique ApaL1 and AscI restriction site and a HC bracketed by a unique SfiI and NotI restriction site. The HC also contains an internal and unique XbaI restriction site between the CDR2 and CDR3 sequence.

To diversify the LC in either a single antigen specific lead antibody or a pool of antigen specific lead antibodies, the Fab antibody gene(s) are first cloned into the yeast display vector pTQ3 as in Example 2, resulting in pTQ3-Fab. A plurality of LC are isolated from a DNA preparation of the CJ phagemid library by restriction digestion with ApaL1 and AscI restriction enzymes. pTQ3-Fab is also digested with ApaL1 and AscI, and the endogenous LC is replaced by a plurality of LC giving rise to a repertoire pTQ3-LC$^{ej\text{-}rep}$. This repertoire is then transferred into yeast strain EBY100 to give EBY100 pTQ3-LC$^{ej\text{-}rep}$.

To diversify the $V_H$ CDR1-2 in either an antigen specific lead antibody or a pool of antigen specific lead antibodies first the Fab antibody gene(s) are cloned into the yeast display vector pTQ3 as in Example 2 to give pTQ3-Fab. A plurality of $V_H$ CDR1-2 fragments are isolated from the CJ phagemid library by restriction digestion with SfiI and XbaI. pTQ3-Fab is also digested with SfiI and XbaI, and the endogenous $V_H$ CDR1-2 fragment is replaced by a plurality of $V_H$ CDR1-2 fragments, resulting in the repertoire pTQ3-$V_H$CDR1-2$^{cj\text{-}rep}$. This repertoire is then transferred into yeast strain EBY100 to give EBY100 pTQ3-$V_H$CDR1-2$^{cj\text{-}rep}$.

It will be clear to those skilled in the art that the cloning procedure can be performed in a number of different ways, e.g., by first constructing a repertoire of $V_H$ CDR1-2 fragments and then cloning in the antigen specific $V_H$ CDR3 or pool of $V_H$ CDR3s.

A culture of EBY100 pTQ3-$V_H$CDR1-2$^{cj\text{-}rep}$ and EBY100 pTQ3-LC$^{cj\text{-}rep}$ is prepared as in Example 2. The yeast culture is then labeled for LC display and antigen binding and affinity selected by flow cytometric sorting as in Example 10. Selected clones are then analyzed for their DNA sequence and there improvement in affinity as in Example 10.

Example 30

Affinity Maturation by Combinatorial Shuffling of Gene Fragments Using Yeast Mating To demonstrate that yeast mating can be used for combinatorial gene diversification and affinity maturation of an antigen specific lead antibody or antigen specific lead antibodies, a selected LC or pool of LCs is rediversified or a $V_H$ CDR1-2 fragment of a selected HC or pool of HCs is rediversified. Antibodies comprising the CJ phagemid library are amenable to such an approach. They have a LC bracketed by a unique ApaL1 and AscI restriction site and a HC bracketed by a unique SfiI and NotI restriction site. The HC also contains an internal and unique XbaI restriction site between the CDR2 and CDR3 sequence. As the LC and HC are present in yeast cells of opposite mating type, yeast mating is used to bring together antigen specific LC with a plurality of $V_H$ CDR1-2 fragments or antigen specific HC with a plurality of LC, thus eliminating the need for restriction-based cloning to pair a LC with a HC.

In one preferred method to diversify an antigen specific lead antibody or a pool of antigen specific lead antibodies, the component HC antibody genes are cloned into the yeast display vector pTQ5 as in Example 13 to give pTQ5-HCAg. A plurality of $V_H$ CDR1-2 fragments are prepared by digestion of HC fragments from the CJ phagemid library with SfiI and XbaI restriction enzymes. This plurality of $V_H$ CDR1-2 fragments is then cloned into DNA prepared from pTQ5-HCAg, which has been digested with SfiI and XbaI to remove the endogenous $V_H$ CDR1-2 fragment and to replace with the plurality of $V_H$ CDR1-2 fragments, the antigen specific $V_H$ CDR3 being retained. This gives a library designated pTQ5-$V_H$ CDR1-2 (CDR3Ag) and this is introduced into the yeast strain EBY100 to give a repertoire EBY100 pTQ5-$V_H$ CDR1-2 (CDR3Ag). A plurality of LC are isolated from a DNA preparation of the CJ phagemid library by restriction digestion with ApaL1 and AscI. This plurality of LC is cloned into pTQ6 to give a repertoire pTQ6-LC$^{rep}$ and serves as one master repertoire for affinity maturation of other antibodies specific for other targets. This repertoire is then transferred into a yeast strain of the opposite mating type, BJ5457, to give BJ5457 pTQ6-LC$^{rep}$.

In one mating regime, which allows for the simultaneous diversification of both the LC and the $V_H$ CDR1-2 gene fragment, cultures of EBY100 pTQ5-$V_H$CDR1-2 (CDR3Ag) and BJ5457 pTQ6-LC$^{rep}$ are prepared as in Example 22. The two repertoires are mated with each other (see Example 19) to give a diploid repertoire EBY100 pTQ5-$V_H$ CDR1-2 (CDR3Ag)/BJ5457 pTQ6-LC$^{rep}$. Fab antibody expression is induced (see Example 18) and the diploid repertoire is affinity selected as in Example 20. Selected clones are analyzed for improved affinity as in Example 23.

While this invention has been particularly shown and described with references to preferred embodiments thereof, it will be understood by those skilled in the art that various changes in form and details can be made therein without departing from the scope of the invention encompassed by the appended claims.

What is claimed is:

1. A method for selecting an antibody that binds to a target antigen by yeast display, comprising the step of:

contacting yeast cells that display a library of multi-chain antibodies with a target antigen, selecting the yeast cell that binds to the target antigen; and identifying the antibody displayed by the selected yeast cell, wherein the multi-chain antibodies each comprise a heavy chain variable region ($V_H$) and a light chain variable region ($V_L$), which are on separate chains.

2. The method of claim 1, wherein the diversity of the library of antibodies is at least $1 \times 10^6$.

3. The method of claim 1, wherein the diversity of the library of antibodies is at least $1 \times 10^7$.

4. The method of claim 1, wherein the sequence of the antibody heavy or light chain variable region is fully human.

5. The method of claim 1, wherein the antibodies each comprise a $V_H$ and a $V_L$, which are encoded respectively by a heavy chain variable region of a human immunoglobulin gene and a light-chain variable region of a human immunoglobulin gene.

6. The method of claim 1, wherein the antibodies each comprise a $V_H$ encoded by a heavy chain variable region of a first human immunoglobulin gene and a $V_L$ encoded by a light chain variable region of a second immunoglobulin gene different from the first human immunoglobulin gene.

7. The method of claim 1, wherein the antibody heavy or light chain variable region is encoded by a human IgG gene.

8. The method of claim 1, wherein the yeast cell that binds to the target antigen is selected by flow cytometric cell sorting.

9. A library of yeast cells displaying a library of multi-chain antibodies on the surface of the yeast cells, comprising: yeast cells transformed with a library of yeast expression vectors encoding a library of antibodies each comprising an antibody heavy chain variable region ($V_H$) and an antibody light chain variable region ($V_L$) wherein the $V_H$ and $V_L$ are on separate chains, wherein at least one yeast expression vector comprises a polynucleotide sequence encoding the $V_H$ or a polynucleotide sequence encoding the $V_L$, which is inserted into the at least one yeast expression vector by homologous recombination, and also a sequence encoding a yeast surface anchoring protein subunit.

10. The library of claim 9, wherein the yeast cells are *Saccharomyces cerevisiae* cells.

11. The library of claim 9, wherein the yeast surface anchoring protein subunit is a-agglutinin or α-agglutinin.

12. The library of claim 9, wherein a region of the $V_H$ or $V_L$ is mutagenized.

13. The library of claim 9, wherein the diversity of the library of antibodies is at least $1 \times 10^6$.

14. The library of claim 9, wherein the diversity of the library of antibodies is at least $1 \times 10^7$.

15. The library of claim 9, wherein the sequence of the antibody heavy or light chain variable region is fully human.

16. The library of claim 9, wherein the $V_H$ and $V_L$ are encoded respectively by a heavy chain variable region of a human immunoglobulin gene and a light-chain variable region of a human immunoglobulin gene.

17. The library of claim 9, wherein the $V_H$ is encoded by a heavy-chain variable region of a first human immunoglobulin gene, and the $V_L$ is encoded by a light chain variable region of a second human immunoglobulin gene different from the first human immunoglobulin gene.

18. The library of claim 9, wherein the antibody heavy or light chain variable region is encoded by a human IgG gene.

* * * * *

SEQUENCE LISTING

```
<160> NUMBER OF SEQ ID NOS: 7

<210> SEQ ID NO 1
<211> LENGTH: 206
<212> TYPE: DNA
<213> ORGANISM: Artificial Sequence
<220> FEATURE:
<223> OTHER INFORMATION: Vector Polylinker

<400> SEQUENCE: 1
atgcagttac ttcgctgttt ttcaatattt tctgttattg ctagcgtttt agcataccca      60
tacgacgttc cagactacgc tagtgcacag gatttcgtgc aatgcggcgc gccaggatcc     120
gcctgaatgg tctgcagacc gtaccgaccg aattcgagtt acctgaggtt aattaacact     180
gttatcgttt aaacgttcag gtgcaa                                          206

<210> SEQ ID NO 2
<211> LENGTH: 66
<212> TYPE: PRT
<213> ORGANISM: Artificial Sequence
<220> FEATURE:
<223> OTHER INFORMATION: Signal Sequence and Epitope Tag

<400> SEQUENCE: 2

Met Gln Leu Leu Arg Cys Phe Ser Ile Phe Ser Val Ile Ala Ser Val
1               5                   10                  15

Leu Ala Tyr Pro Tyr Asp Val Pro Asp Tyr Ala Ser Ala Gln Asp Phe
```

```
            20                  25                  30
Val Gln Cys Gly Ala Pro Gly Ser Ala Met Val Cys Arg Pro Tyr Arg
        35                  40                  45

Pro Asn Ser Ser Tyr Leu Arg Leu Ile Asn Thr Val Ile Val Thr Phe
    50                  55                  60

Arg Cys
65

<210> SEQ ID NO 3
<211> LENGTH: 119
<212> TYPE: DNA
<213> ORGANISM: Artificial Sequence
<220> FEATURE:
<223> OTHER INFORMATION: Vector Sequence

<400> SEQUENCE: 3
ggaggcggag gttctggggg cggaggatct ggtggcggag gttctgcggc ccagccggcc        60
agtcctgatg cggccgcaga acaaaaactc atctcagaag aggatctgaa tttaattaa       119

<210> SEQ ID NO 4
<211> LENGTH: 37
<212> TYPE: PRT
<213> ORGANISM: Artificial Sequence
<220> FEATURE:
<223> OTHER INFORMATION: Epitope Tag

<400> SEQUENCE: 4

Gly Gly Gly Gly Ser Gly Gly Gly Ser Gly Gly Gly Ser Gly
 1               5                  10                  15

Gly Gln Pro Gly Ser Pro Asp Ala Ala Ala Glu Gln Lys Leu Ile Ser
                20                  25                  30

Glu Glu Asp Leu Asn
        35

<210> SEQ ID NO 5
<211> LENGTH: 1213
<212> TYPE: DNA
<213> ORGANISM: Artificial Sequence
<220> FEATURE:
<223> OTHER INFORMATION: Vector Sequence

<400> SEQUENCE: 5
caaaatcgac tttgttccca ctgtactttt agctcgtaca aaatacaata tactttcat        60 ttctccgtaa acaacatgtt ttcccatgta atatcctttt ctattttcg ttccgttacc       120 aactttacac atactttata tagctattca cttctataca ctaaaaaact aagacaattt      180
taattttgct gcctgccata tttcaatttg ttataaattc ctataattta tcctattagt      240
agctaaaaaa agatgaatgt gaatcgaatc ctaagagaat tcacggatta gaagccgccg      300
agcgggtgac agccctccga aggaagactc tcctccgtgc gtcctcgtct tcaccggtcg      360
cgttcctgaa acgcagatgt gcctcgcgcc gcactgctcc gaacaataaa gattctacaa      420
tactagcttt tatggttatg aagaggaaaa attggcagta acctggcccc acaaaccttc      480
aaatgaacga atcaaattaa caaccatagg atgataatgc gattagtttt ttagccttat      540
ttctggggta attaatcagc gaagcgatga ttttgatct attaacagat atataaatgc      600
aaaaactgca ttaaccactt taactaatac tttcaacatt tcggtttgt attacttctt      660 attcaaatgt aataaaagta tcaacaaaaa attgttaata tacctctata ctttaacgtc      720
aaggagaaaa aacccggatc ggactactag cagctgtaat acgactcact ataggaata      780
```

```
ttaagctaat tctacttcat acattttcaa ttaagatgca gttacttcgc tgttttcaa      840 tattttctgt tattgcttca gttttagcac aggaactgac aactatatgc gagcaaatcc      900
cctcaccaac tttagaatcg acgccgtact ctttgtcaac gactactatt ttggccaacg      960
ggaaggcaat gcaaggagtt tttgaatatt acaaatcagt aacgtttgtc agtaattgcg     1020
gttctcaccc ctcaacgact agcaaaggca gccccataaa cacacagtat gttttggag     1080 gcggaggttc tggggcgga ggatctggtg gcggaggttc tgcggcccag ccggccagtc     1140
ctgatgcggc cgcagaacaa aaactcatct cagaagagga tctgaattta attaacactg     1200
ttatcgttta aac                                                         1213
```

```
<210> SEQ ID NO 6
<211> LENGTH: 126
<212> TYPE: DNA
<213> ORGANISM: Artificial Sequence
<220> FEATURE:
<223> OTHER INFORMATION: Vector Sequence, Amino Acid Leader
<220> FEATURE:
<221> NAME/KEY: CDS
<222> LOCATION: (1)...(126)

<400> SEQUENCE: 6 atg cag tta ctt cgc tgt ttt tca ata ttt tct gtt att gct agc gtt     48
Met Gln Leu Leu Arg Cys Phe Ser Ile Phe Ser Val Ile Ala Ser Val
 1               5                  10                  15 tta gca tac cca tac gac gtt cca gac tac gct agt gca cag gat ttc     96
Leu Ala Tyr Pro Tyr Asp Val Pro Asp Tyr Ala Ser Ala Gln Asp Phe
             20                  25                  30 gtg caa tgc ggc gcg cca gga tcc atg taa                             126
Val Gln Cys Gly Ala Pro Gly Ser Met *
         35                  40
```

```
<210> SEQ ID NO 7
<211> LENGTH: 131
<212> TYPE: PRT
<213> ORGANISM: Artificial Sequence
<220> FEATURE:
<223> OTHER INFORMATION: Flanking Sequences

<400> SEQUENCE: 7

Met Gln Leu Leu Arg Cys Phe Ser Ile Phe Ser Val Ile Ala Ser Val
 1               5                  10                  15

Leu Ala Gln Glu Leu Thr Thr Ile Cys Glu Gln Ile Pro Ser Pro Thr
             20                  25                  30

Leu Glu Ser Thr Pro Tyr Ser Leu Ser Thr Thr Thr Ile Leu Ala Asn
         35                  40                  45

Gly Lys Ala Met Gln Gly Val Phe Glu Tyr Tyr Lys Ser Val Thr Phe
     50                  55                  60

Val Ser Asn Cys Gly Ser His Pro Ser Thr Thr Ser Lys Gly Ser Pro
65                  70                  75                  80

Ile Asn Thr Gln Tyr Val Phe Gly Gly Gly Ser Gly Gly Gly
             85                  90                  95

Ser Gly Gly Gly Gly Ser Ala Ala Gln Pro Ala Ser Pro Asp Ala Ala
                100                 105                 110

Ala Glu Gln Lys Leu Ile Ser Glu Glu Asp Leu Asn Leu Ile Asn Thr
            115                 120                 125

Val Ile Val
    130
```